US011898192B2

(12) United States Patent
Bardet et al.

(10) Patent No.: US 11,898,192 B2
(45) Date of Patent: Feb. 13, 2024

(54) METHOD FOR QUANTIFYING AT LEAST ONE MICROORGANISM GROUP VIA MASS SPECTROMETRY

(71) Applicant: BIOMÉRIEUX, Marcy l'Etoile (FR)

(72) Inventors: Chloé Bardet, Lyons (FR); Tiphaine Cecchini, Saint Genis les Ollières (FR); Yannick Charretier, Courzieu (FR); Jean-Philippe Charrier, Tassin la Demi-Lune (FR); Christelle Compagnon, Lyons (FR); Tanguy Fortin, Lyons (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 0 days.

(21) Appl. No.: 15/503,802

(22) PCT Filed: Aug. 11, 2015

(86) PCT No.: PCT/FR2015/052196
§ 371 (c)(1),
(2) Date: Feb. 14, 2017

(87) PCT Pub. No.: WO2016/024068
PCT Pub. Date: Feb. 18, 2016

(65) Prior Publication Data
US 2017/0275667 A1 Sep. 28, 2017

(30) Foreign Application Priority Data
Aug. 14, 2014 (FR) ...................................... 1457828

(51) Int. Cl.
*C12Q 1/06* (2006.01)
*G01N 33/569* (2006.01)
*G01N 33/68* (2006.01)

(52) U.S. Cl.
CPC ............. *C12Q 1/06* (2013.01); *G01N 33/569* (2013.01); *G01N 33/6848* (2013.01)

(58) Field of Classification Search
None
See application file for complete search history.

(56) References Cited

U.S. PATENT DOCUMENTS

| | | | |
|---|---|---|---|
| 6,551,795 B1 | 4/2003 | Rubenfield et al. | |
| 2004/0259226 A1 | 12/2004 | Robey et al. | |
| 2007/0178450 A1 | 8/2007 | Wheeler et al. | |

FOREIGN PATENT DOCUMENTS

| | | | | |
|---|---|---|---|---|
| EP | 2124060 A1 | 11/2009 | | |
| WO | 01/70955 A2 | 9/2001 | | |
| WO | 02/077183 A2 | 10/2002 | | |
| WO | 2006/079076 A2 | 7/2006 | | |
| WO | 2012/092302 A1 | 7/2012 | | |
| WO | WO-2013166169 A1 | * 11/2013 | ......... | G01N 33/6848 |

OTHER PUBLICATIONS

Schmidt, A. et al. 2011. Absolute quantification of microbial proteomes at different states by directed mass spectrometry. Molecular Systems Biology 7(510): 1-16. specif. pp. 1, 2, 12.*
Sauer, S. et al. 2010. Mass spectrometry tools for the classification and identification of bacteria. Nature Reviews/Microbiology 8: 74-82. specif. pp. 74, 78, 80.*
Guina, T. et al. 2003. Proteomic analysis of Pseudomonas aeruginosa grown under magnesium limitation. Journal of the American Society for Mass Spectrometry 14: 742-751. specif. pp. 742, 750.*
NCBI Blast. SEQ ID No. 6. Datasheet [online]. NCBI.NLM.NIH. gov [retrieved on Oct. 1, 2018]. Retrieved from the Internet: <URL: https://blast.ncbi.nlm.nih.gov/Blastcgi#alnHdr_734479104, pp. 1-10. specif. pp. 2, 6.*
Liebler, D.C. et al. Mar. 21, 2013. Targeted quantitation of proteins by mass spectrometry. Biochemistry 52: 3797-3806. specif. pp. 3797, 3801, 3802.*
Liang, S.-T. et al. 2000. mRNA composition and control of bacterial gene expression. Journal of Bacteriology 182(11): 3037-3077. specif. p. 3037.*
Klumpp, S. et al. 2009. Growth rate-dependent global effects on gene expression in bacteria. Cell 139: 1366-1375. specif. pp. 1367, 1368.*
Matsunaga, J. et al. 2005. Osmolarity, a key environmental signal controlling expression of leptospiral proteins LigA and LigB and the extracellular release of LigA. Infection and Immunity 73(1): 70-78. specif. p. 72.*
Fricke, B. et al. 1999. Characterization and purification of an outer membrane metalloproteinase from Pseudomonas aeruginosa with fibrinogenolytic activity. Biochimica et Biophysica Acta 1454: 236-250. specif. pp. 236, 240.*
Zubkov, M.V. et al. 1999. Determination of total protein content of bacterial cells by SYPRO staining and flow cytometry. Applied and Environmental Microbiology 65(7): 3251-3257. specif. pp. 3254, 3256.*
Fricke, B. et al. 1999. Characterization and purification of an outer membrane metalloproteinase from Pseudomonas aeruginosa with fibrinogenolytic activity. Biochimica et Biophysica Acta 1454: 236-250. specif. p. 240.*
Clark, J. How the mass spectrometer works. Last updated Aug. 15, 2020. LibreTexts. Datasheet [online]. Retrieved on Jul. 15, 2021. Downloaded from the internet: <https://chem.libretexts.org/@go/page/3275>. pp. 1-3. specif. pp. 1, 2.*

(Continued)

*Primary Examiner* — Michael Barker
*Assistant Examiner* — Sharon M. Papciak
(74) *Attorney, Agent, or Firm* — Oliff PLC

(57) ABSTRACT

A method for quantifying at least one microorganism group via at least one mass spectrometry analysis. The method includes at least one separation and fragmentation step. The method moreover includes a step that involves measuring the amount of at least one representative peptide or at least one protein representing the microorganism group. The at least one representative peptide or the at least one protein is obtained after the at least one separation and fragmentation step and serves as a quantification marker(s). The amount of the quantification marker(s) is directly correlatable to the amount of the at least one microorganism group.

4 Claims, 4 Drawing Sheets

Figure 1:
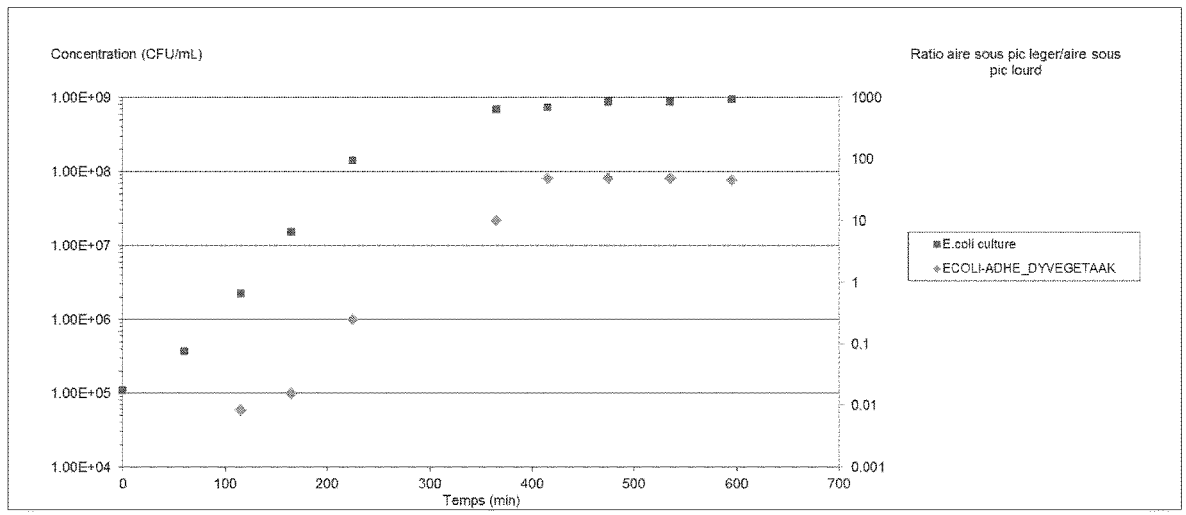

Specification includes a Sequence Listing.

(56) References Cited

OTHER PUBLICATIONS

Anderson, Leigh et al: "Quantitative Mass Spectrometric Multiple Reaction Monitoring Assays for Major Plasma Proteins." 2006, pp. 573-588, Molecular & Cellular Proteomics, 5.4.
Anhalt, John et al. "Identification of Bacteria Using Mass Spectrometry." Analytical Chemistry, vol. 47, No. 2, Feb. 1975. pp. 219-225.
Brun, Virginie et al. "Isotope-labeled Protein Standards." 2007, Molecular and Cellular Proteomics 6.12, pp. 2139-2149.
Bundy, Jonathan et al. "Lectin-Based Affinity Capture for MALDI-MS Analysis of Bacteria." Analytical Chemistry, vol. 71, No. 7, Apr. 1999. pp. 1460-1463.
Chen, Wei-Jen et al. "Functional Nonoparticle-Based Proteomic Strategies for Characterization of Pathogenic Bacteria." Analytical Chemistry, vol. 80, No. 24, Dec. 2008. pp. 9612-9621.
Claydon, Martin et al. "The Rapid Identification of Intact Microorganisms Using Mass Spectometry." Nature Biotechnology, vol. 14, Nov. 1996. pp. 1584-1586.
Desiere, Frank et al. "The PeptideAtlas project." Nucleic Acids Research, 2006, vol. 34. Issue D655-D658.
Everley, Robert et al. "Characterization of Clostridium species utilizing liquid chromatography/mass spectrometry of intact proteins." Journal of Microbiological Methods, vol. 77, pp. 152-158, 2009.
Fortin, Tanguy et al. "Clinical Qunatitation of Prostate-specific Antigen Biomarker in the Low Nanogram/Milliliter Range by Conventional bore Liquid Chromatography-Tandem Mass spectrometry (Multiple Reaction Monitoring) coupling and Correlation with ELISA Tests." 2009 Molecular and Cellular Proteomics, vol. 8, No. 5, pp. 1006-1015.
Fusaro, Vincent et al. "Prediction of high-responding peptides for targeted protein assays by mass spectrometry." Nature Biotechnology, vol. 27, No. 2, Feb. 2009.
Gaskell, Simon. "Electrospray: Principles and Practice." Journal of Mass Spectrometry, vol. 32, pp. 677-688. 1997.
Han, Bomie et al. Proteomics: from hypotesis to quantitative assay on a signle platfom. Guidelines for developing MRM assays using ion trap mass spectrometers. Briefings in Functional Genomics and Proteomics, vol. 7, No. 5. pp. 340-354, 2008.
Hernychova, Lenka. "Detection and Identification of Coxiella burnetii Based on the Mass Spectrometric Analyses of the Extracted Proteins." Analytical Chemistry, vol. 80, No. 18. Sep. 2008, pp. 7097-7104.
Keshishian, Hasmik et al. "Quantitative, Multiplexed Assays for Low Abundance Proteins in Plasma by Targeted Mass Spectrometry and Stable Isotope Dilution." 2007, Molecular & Cellular Proteomics 6.12, pp. 2212-2229.
Krishnamurthy, Thaiya et al. "Rapid Identification of Bacteria by Direct Matrix-assisted Laser Desorption/Ionization Mass Spectrometric Analysis of Whole Cells." Rapid Communications in Mass Spectrometry, 1996 vol. 10, pp. 1992-1996.
Lin, Ya-Shiuan et al. "Affinity Capture Using Vancomycin-Bound Magnetic Nanoparticles for the MALDI-MS Analysis of Bacteria." Analytical Chemistry, vol. 77, No. 6. Mar. 2005. 1753-1760.
Lopez-Ferrer, Daniel et al. "On-line Digestion System for Protein Characterization and Proteome Analysis." Analytical Chemistry, vol. 80, No. 23, Dec. 2008. pp. 8930-8936.
Lopez-Ferrer, Daniel et al. "Ultra Fast Trypsin Digestion of Proteins by High Intensity Focused Ultrasound." Journal of Proteome Research. 2005. pp. 1569-1574.
Manes, Nathan et al. "Targeted Protein Degradation by *Salmonella* under Phagosome-mimicking Culture Conditions Investigated Using Comparative Peptidomics." 2007, Molecular & Cellular Proteomics, vol. 6, No. 4, pp. 717-727.
Mead, Jennifer et al. "MRMaid, the Web-based Tool for Designing Multiple Reaction Monitoring (MRM) Transtitions." Molecular & Cellular Proteomics 8.4, 2009, pp. 696-705.

Nandakumar et al. "Proteomic analysis of endodontic infections by liquid chromatography-tandem mass spectrometry." Oral Microbiology and Immunology, vol. 24, pp. 347-352, 2009.
Pratt, Julie et al. "Multiplexed absolute quantification for proteomics using concatenated signature peptides encoded by QconCAT genes." Nature Protocols, vol. 1, No. 2. 2006, pp. 1029-1043.
Seng, Piseth et al. "Ongoing Revolution in Bacteriology: Routine Identification of Bacteria by Matrix-Assisted Laser Desorption Ionization Time-of-Flight Mass Spectrometry." Clinical Infectious Diseases, vol. 49, 543-551. 2009.
Stal-Zeng, Jianru et al. High Sensitivity Detection of Plasma Proteins by Multiple Reaction Monitoring of N-Glycosites. Molecular & Cellular Proteomics 6.10, pp. 1809-1817, Stahl-Zeng 2007.
Vaidyanathan, Seetharaman et al. Discrimination of Aerobic Endospore-forming Bacteria via Electrospray-Ionization Mass Spectrometry of Whole Cell Suspensions. Analytical Chemistry, vol. 73, No. 17, pp. 4134-4144. Sep. 2001.
Wang Kai-Yi et. al. "Multiplexed Immunoassay: Quantitation and Profiling of Serum Biomarkers Using Magnetic Nanoprobes and MALDI-TOF MS." Analytical Chemistry, vol. 80, No. 16. Aug. 2008. pp. 6159-6167.
Otto, Andreas. "Global Relative and Absolute Quantitation in microbial proteomics". Current Opinion in Microbiology, vol. 15., 364-372, 2012.
Dalgaard, Paw. "Estimation of Bacterial Growth Rates from Turbidimetric and viable count data". International Journal of Food of Microbiology, vol. 23, 391-404, 1994.
Gentry, T.J. "Microarray Applications in Microbial Ecology Research". vol. 52, 159-175, 2006.
Venable, John D. "Automated Approach for quantitative analysis of complex peptide mixtures from tandem mass spectra". Nature Methods, vol. 1 No. 1, Jan. 7, 2004.
Rost, H.L. "OpenSwath enables automated, targeted analysis of data-independent acquisition MS data". Nature Biotechnology, vol. 32, No. 3, 219-223, 2014.
Plumb, Robert. UPLC/MSE; "A new approach for generating molecular fragment information for biomarker structure elucidation." Rapid Communications in Mass Spectrometry, vol. 20, 189-1994, 2006.
Dupont, Myrielle. "An Early Response to Environmental Stress Involves Regulation of OmpX and OmpF, Two Enterobacterial Outer Membrane Pore-Forming Proteins." Antimicrobial Agents and Chemotherapy, vol. 51 No. 9, 3190-3198, 2007.
Cohen, C.Y., "Rapid Flow Cytometric Bacterial Detection and Determination of Susceptibility to Amikacin in Body Fluids and Exudates". Journal of Clinical Microbiology, vol. 27, No. 6, 1250-1256, 1989.
Nov. 1, 2016 Written Opinion and Search Report issued in French Patent Application No. PCT/FR2015/052196.
Sheng, Pan. "Mass Spectrometry Based Targeted Protein Quantification: Methods and Applications". Journal of Proteome Research, vol. 8, 787-797, 2009.
Walther, Tobias. "Mass Spectrometry-based proteomics in cell biology". The Journal of Cell Biology, vol. 190 No. 4, 491-500, 2010.
Ross, Philip. "Multiplexed Protein Quantitation in *Saccharomyces cerevisiae* Using Amine-reactive Isobaric Tagging Reagents". vol. 3.12, 1154-1169, 2004; Molecular & Cellular Proteomics.
Jul. 28, 1992 UniParc—UPI000016F527; XP—002751647.
Lange, Vinzenz. "Targeted Quantitative Analysis of *Streptococcus pyogenes* Virulence Factors by Multiple Reaction Monitoring". vol. 7.8, 1489-1500, Molecular & Cellular Proteomics, 2008.
Chien-Hsun Teng. "Gold Nanoparticles as Selective and Concentrating Probes for Samples in MALDI MS Aanalysis". Analytical Chemistry, vol. 76, No. 15, 4337-4342, 2004.
Nov. 31, 2015 International Search Report issued in French Patent Application No. PCT/FR2015/052196.

\* cited by examiner

METHOD FOR QUANTIFYING AT LEAST ONE MICROORGANISM GROUP VIA MASS SPECTROMETRY

The present invention relates to the bacteriology field. More specifically, the invention relates to the quantification of microorganisms from a sample, using mass spectrometry.

Since the discovery of microbes by Pasteur, microorganisms have been studied by microscopy and by chemical analyses and quantified by quantitative cultures. These conventional methods are often long and fastidious and analytical alternatives were sought very early. Thus, the analysis of bacteria by mass spectrometry was initiated as early as 1975 by J. Anhalt and C. Fenselau [1].

These preliminary studies were followed by the study, by gas chromatography-mass spectrometry (GC-MS), of microorganism wall fatty acids [2]. This method became more widely known as FAME for Fatty Acid Methyl Ester. It currently constitutes a reference method for taxonomic studies. However, its use remains limited to certain specialist laboratories which master the treatment of the sample by saponification, hydrolysis and derivation.

In 1996, the works of M. Claydon et al. [3] and also of T. Krishnamurthy and P. Ross [4] showed the possibility of identifying various bacterial species with a MALDI-TOF (Matrix Assisted Laser Desorption Ionization—Time-of-Flight) mass spectrometer. The analysis combines the acquisition of a mass spectrum and the interpretation of expert software. It is extremely simple and can be carried out in a few minutes. However, it has only very recently begun to spread among medical testing laboratories [5]. Its clinical use is currently limited to the identification of species of bacteria and yeasts. It is not used for quantification.

However, the quantification of microorganisms is fundamental both in the clinical field and in the industrial field. Thus, for example, the quantification of bacteria is an essential element in the diagnosis of certain infections, in order to ensure optimal treatment of patients. Likewise, the quantification of bacteria is important in the study of the amount of certain proteins expressed by the bacterium.

Many applications have been developed in the absolute or relative quantification of microbial proteins by MS/MS mass spectrometry, but no applications have been developed in the quantification of microorganisms by MS/MS mass spectrometry [6].

Document US 2004/0259226 describes methods for quantifying microorganisms involved in bioterrorism by measuring a microbial marker, which is the chaperon 60 protein (cpn60). This document describes various quantification methods and cites, among these methods, mass spectrometry and in particular MALDI-TOF mass spectrometry as being a possible technique for quantifying proteins or peptides. This document limits itself to just citing this technique, without proving its relevance and its effectiveness by means of concrete examples. It is known today, moreover, that the chaperon 60 protein has a high mass (in the region of 60 kDa) which makes it detection by MALDI-TOF very difficult in a complex sample, such as a microorganism. This is because, during a MALDI ionization, the various molecules which make up the sample compete and only the molecules which are the most abundant and have lower masses are easily ionized and detected. Thus, the identification of microorganism by MALDI-TOF conventionally uses a detection between 2 and 20 kDa, which is much smaller than the mass of the chaperon 60 protein. Furthermore, the reproducibility of the MALDI ionization is mediocre. The ionization depends a great deal on the matrix used, on the reproducibility of the deposit, that is to say the quality of the mixture of the sample and of the matrix, but also on the localization and the number of laser shots. As a result, the quantification of proteins or peptides is unsuitable for the assaying of the chaperon 60 protein.

The standard methods for the quantitative analysis of microorganisms are the method of counting on a dish and the method of analyzing turbidity by spectrophotometry.

The method of counting on a dish consists of serial dilutions of a sample in physiological saline inoculated onto Petri dishes, until a dish on which the colonies can be accurately counted is obtained.

Analysis by spectrophotometry consists in analyzing the optical density of a sample, which serves as an indicator of growth of the bacterium, but does not allow absolute quantification of all the bacterial groups present [7].

Other techniques used in the quantification of bacteria have been developed, implementing molecular biology methods (Polymerase Chain Reaction, microarray) [8]. However, the PCR technique which can be used in a clinical microbiology laboratory does not easily make it possible to multiplex the quantification of at least one bacterial group with another or with the quantification of proteins that may provide a clinical interest as regards the resistance phenotype of said bacterial group.

More recently, flow cytometry techniques have provided a method which may meet the clinical needs regarding quantification [9].

These techniques are, however, difficult to apply to routine clinical use. They use instruments that require qualified personnel. The analysis times, often longer than one hour per sample, are incompatible with the workload of a microbiological analysis laboratory.

In this context, the objective of the present invention is to provide a method for specific quantification of microorganisms, namely identification and determination of the quantification of at least one microorganism group, which makes it possible to overcome the drawbacks of the prior art methods, namely to provide a method which is inexpensive, without reagents that are specific to each species, in particular compared with molecular biology processes, allowing a selective analysis of proteins or peptides, giving a result in a short time, of less than one hour, and that can be used in a routine clinic, without requiring highly qualified personnel. Furthermore, the entire method for specific quantification of the bacterial group and also of the proteins of interest in the characterization of said bacterial group can be advantageously carried out with one and the same mass spectrometer, thereby simplifying the instrumentation of the microbiological analysis laboratory.

To this end, the subject of the invention relates to a novel method for quantifying at least one microorganism group via at least one mass spectrometry analysis comprising at least one separation and fragmentation step, said method comprising, moreover, a step consisting in measuring the amount of at least one representative peptide or of at least one representative protein of said microorganism group, said at least one representative peptide or said at least one protein being obtained after the at least one separation and fragmentation step and serving as quantification marker(s), it being possible for the amount of said quantification marker(s) to be directly correlated to the amount of the at least one microorganism group.

The microorganism groups that can be quantified by means of the method of the invention are all groups of microorganisms representing a family, a genus or a species of pathogenic or non-pathogenic microorganisms.

The sample on which the method of the invention can be implemented is any sample capable of containing a target microorganism. The sample may be of biological, animal (veterinary), plant or human (clinical) origin. It may then correspond to a specimen of biological fluid (bronchical, whole blood, serum, plasma, urine, cerebrospinal fluid, organic secretion, for example, specimen), a tissue specimen or isolated cells. This specimen can be used as it is insofar as the microorganism characterization markers are available in the sample tested, or else it can undergo, prior to the analysis, a preparation of extraction, concentration, purification or culturing type, according to methods known to those skilled in the art.

The sample may be of industrial origin in the case of a microbiological test. According to a nonexhaustive list, it may be a specimen of air, a specimen of water, a specimen taken from a surface, a part or a manufactured product or a product of food origin. Among the samples of food origin, mention may be made, nonexhaustively, of a sample of a milk product (yogurts, cheeses, etc.), of meat, of fish, of egg, of fruit, of vegetable, of water or of a beverage (milk, fruit juice, soda, etc.). These samples of food origin may also come from sauces or prepared dishes. Finally, a food sample may be derived from an animal feed, such as in particular animal meals.

The term "microorganisms" is intended to mean in particular bacteria, yeast, molds or viruses.

The term "markers of the identity and of the amount of at least one microorganism group" is intended to mean molecules, of protein origin, which are characteristic of said properties.

According to one preferred embodiment of the method according to the invention, said method comprises a step consisting in carrying out the identification of the at least one microorganism group simultaneously with the quantification of said at least one microorganism group.

The term "identification of a microorganism group" is intended to mean the differentiation of several species within one and the same genus or else of other genera of microorganisms, the differentiation of several genera within one and the same family or else various families of microorganisms, or the differentiation of several families within one and the same class or else various classes of microorganisms.

The term "quantification of at least one microorganism group in a sample" is intended to mean the quantification of a protein or peptide marker or a marker representative of the amount of the microorganism group(s) in a sample. A marker molecule for quantifying at least one microorganism group is a molecule of which the amount produced or expressed does not vary according to the growth phase in which said microorganism group is situated, or as a function of the type of culture (agar or broth) having been subjected to said microorganism group, or as a function of the strains used that are part of a single one and the same microorganism group.

Another subject of the invention relates to a method for measuring the level of expression of at least one peptide and/or of at least one protein of interest of a microorganism group, by means of at least one mass spectrometry analysis comprising at least one separation and fragmentation step, said method comprising the following steps:

a) measuring the amount of the at least one peptide of interest and/or of the at least one protein of interest, b) measuring the amount of at least one peptide representative or of at least one protein representative of said microorganism group, serving as quantification marker (s), it being possible for the amount of said quantification marker(s) to be directly correlated to the amount of the at least one microorganism group, c) deducing the level of expression of the at least one peptide and/or of the at least one protein of interest of said microorganism group, the at least one peptide of interest and/or the at least one protein of interest, and also the at least one peptide representative or the at least one protein representative of said microorganism group, being obtained after the at least one separation and fragmentation step.

More specifically, step c) of the method according to a second subject of the invention consists in comparing the measured amount of the at least one peptide of interest and/or of the at least one protein of interest with the amount of the at least one peptide representative or of the at least one protein representative of said microorganism group serving as quantification marker(s), such that it is thus possible to deduce a relative expression level with respect to the amount of said quantification marker(s).

Advantageously, the method according to the invention comprises an additional step $b_1$) consisting in determining the amount of the at least one microorganism group on the basis of the amount of said quantification marker(s) obtained in step b). This additional step is carried out in a manner similar to the method according to the first subject of the invention.

It should be noted that the quantification markers specific for a microorganism group can also be used as markers for identification of said microorganism group.

The aims and advantages of the present invention will be understood more clearly in the light of the detailed description which follows, in relation to the drawing in which:

FIG. 1 shows, for an *Escherichia coli* strain, the evolution as a function of culture time of the amount of bacteria, measured by counting on Petri dishes after successive dilutions (left-hand axis) and by MRM mass spectrometry (right-hand axis). In this example, the MRM signal representative of the amount of bacteria is the signal of the peptide of sequence SEQ ID No. 2 specific for *Escherichia coli*. It is measured by the ratio of the area under the chromatographic peak of the natural peptide divided by the area under the chromatographic peak of a synthetic calibration peptide, having the same sequence as the natural peptide, but synthesized with lysine and arginine made heavier by means of nitrogen 15 ($^{15}$N) and carbon 13 ($^{13}$C).

Figure 2:
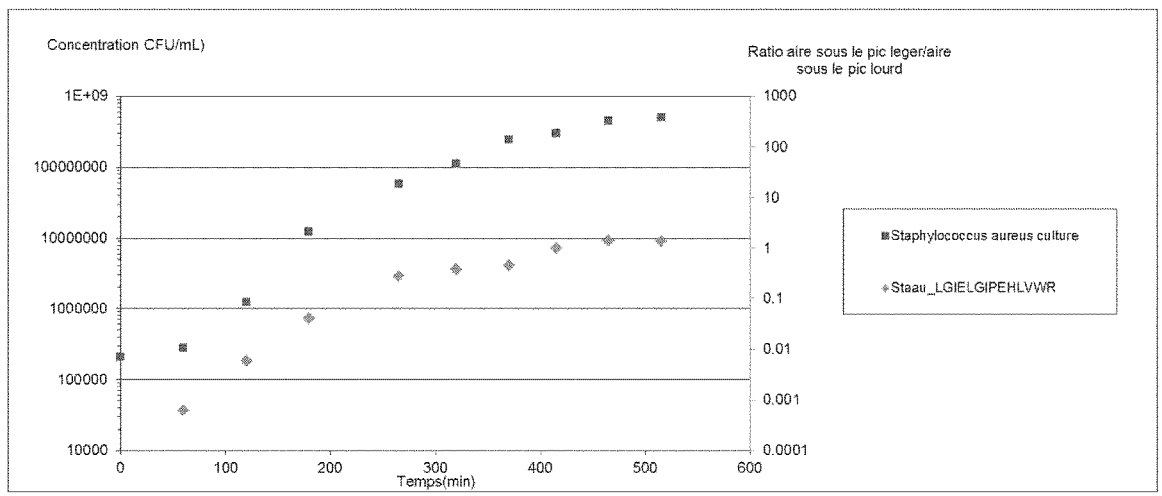

FIG. 2 shows, for a *Staphylococcus aureus* strain, the evolution as a function of culture time of the amount of bacteria, measured by counting on Petri dishes 15 after successive dilutions (left-hand axis) and by MRM mass spectrometry (right-hand axis). In this example, the MRM signal representative of the amount of bacteria is the signal of the peptide of sequence SEQ ID No. 4 specific for *Staphylococcus aureus*. It is measured by the ratio of the area under the chromatographic peak of the natural peptide divided by the area under the 20 chromatographic peak of a synthetic calibration peptide, having the same sequence as the natural peptide, but synthesized with lysine and arginine made heavier by means of nitrogen 15 ($^{15}$N) and carbon 13 ($^{13}$C).

Figure 3:
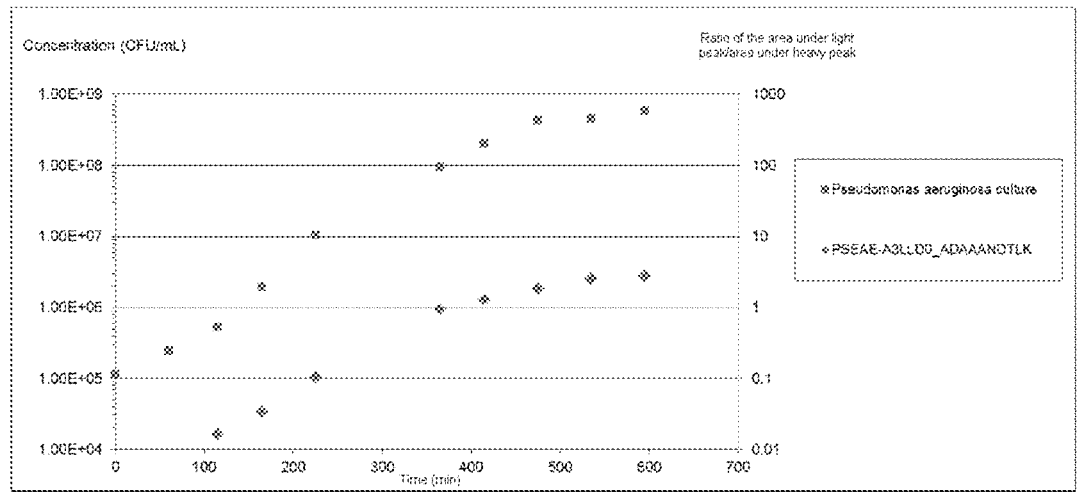

FIG. 3 shows, for a *Pseudomonas aeruginosa* strain, the evolution as a function of culture time of the amount of bacteria, measured by counting on Petri dishes after successive dilutions (left-hand axis) and by MRM mass spectrometry (right-hand axis). In this example, the MRM signal representative of the amount of bacteria is the signal of the peptide of sequence SEQ ID No. 6 specific for *Pseudomonas aeruginosa*. It is measured by the ratio of the area under the chromatographic peak of the natural peptide divided by the area under the chromatographic peak of a synthetic calibration peptide, having the same sequence as the natural peptide, but synthesized with lysine and arginine made heavier by means of nitrogen 15 ($^{15}N$) and carbon 13 ($^{13}C$).

Figure 4:
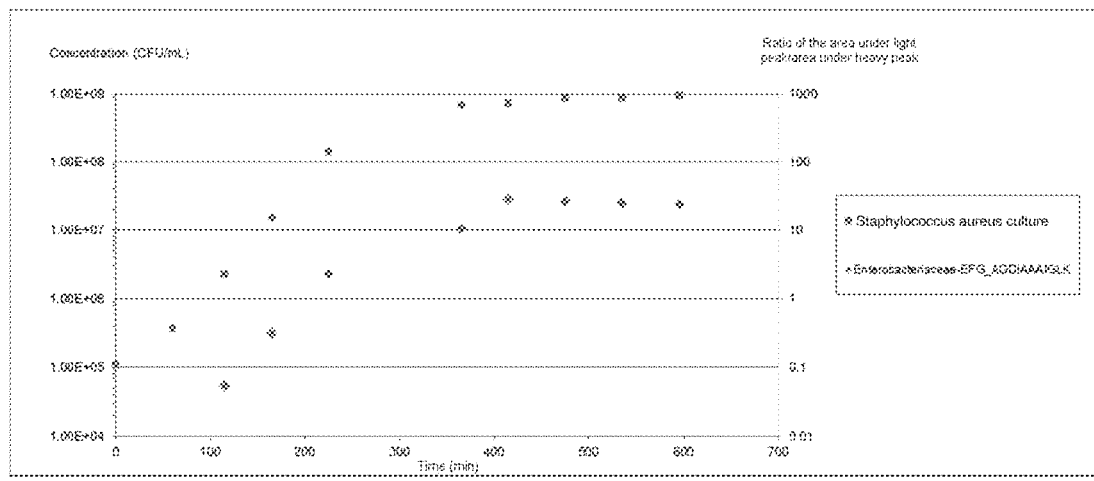

FIG. 4 shows, for an enterobacteria strain, the evolution as a function of culture time of the amount of bacteria, measured by counting on Petri dishes after successive dilutions (left-hand axis) and by MRM mass spectrometry (right-hand axis). In this example, the MRM signal representative of the amount of bacteria is the signal of the peptide of sequence SEQ ID No. 8 specific for the enterobacteria family. It is measured by the ratio of the area under the chromatographic peak of the natural peptide divided by the area under the chromatographic peak of a synthetic calibration peptide, having the same sequence as the natural peptide, but synthesized with lysine and arginine made heavier by means of nitrogen 15 ($^{15}N$) and carbon 13 ($^{13}C$).

Figure 5:
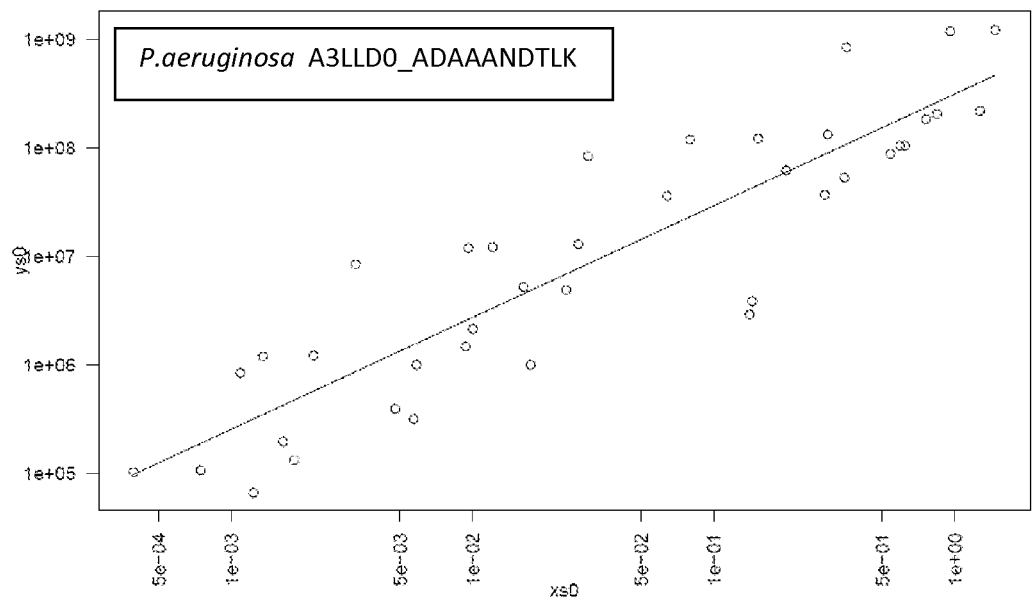

FIG. 5 shows, for *Pseudomonas aeruginosa*, the correlation between the concentration of bacteria present in the sample and the amount of peptide of sequence SEQ ID No. 6, measured by MRM mass spectrometry for several *Pseudomonas aeruginosa* strains. The correlation straight line plotted on this figure makes it possible to calculate the amount of bacteria from the MRM signal as indicated in FIG. 3.

Figure 6:
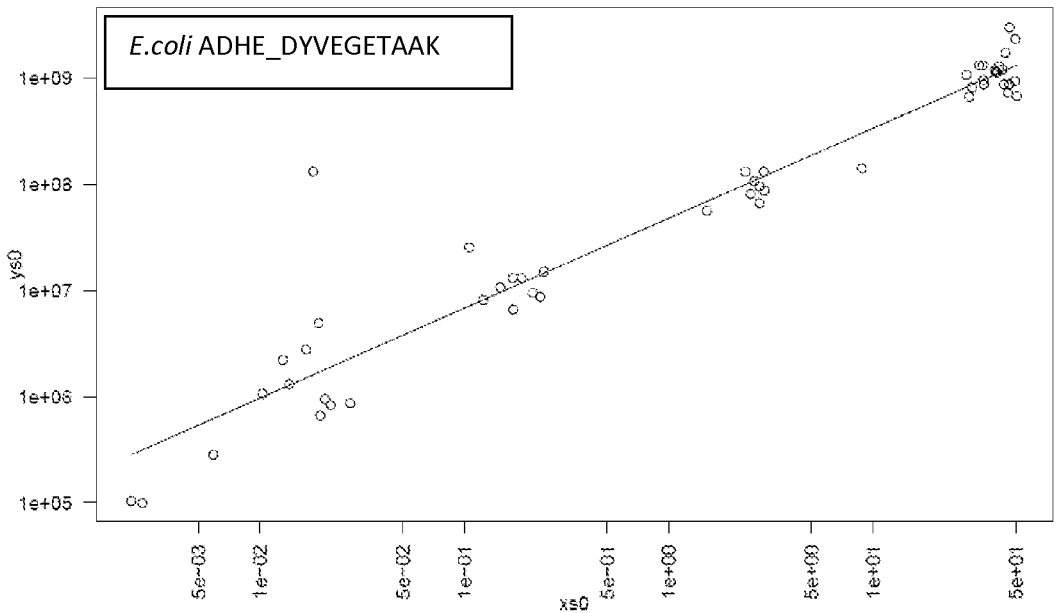

FIG. 6 shows, for *Escherichia coli*, the correlation between the concentration of bacteria present in the sample and the amount of peptide of sequence SEQ ID No. 2, measured by ESI-MS/MS mass spectrometry for several *Escherichia coli* strains. The correlation straight line plotted on this figure makes it possible to calculate the amount of bacteria from the MRM signal measured as indicated in FIG. 1.

Figure 7:
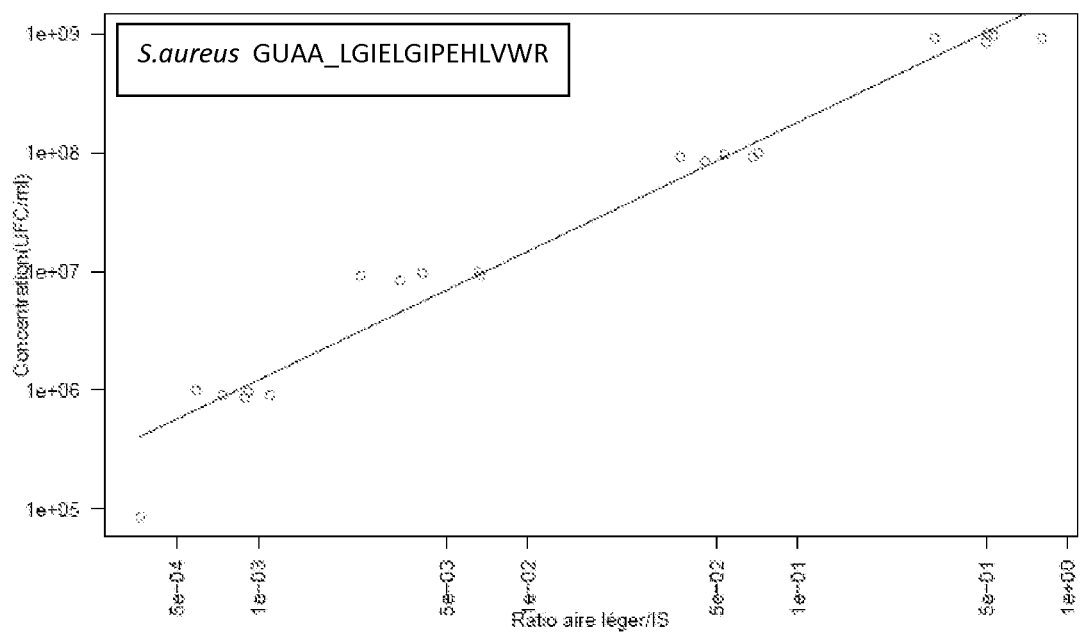

FIG. 7 shows, for *Staphylococcus aureus*, the correlation between the concentration of bacteria present in the sample and the amount of peptide of sequence SEQ ID No. 4, measured by ESI-MS/MS mass spectrometry for several *Staphylococcus aureus* strains. The correlation straight line plotted on this figure makes it possible to calculate the amount of bacteria from the MRM signal measured as indicated in FIG. 2.

The method of the invention can be implemented for quantifying bacterial species.

Thus, for example, by way of bacterial species that can be quantified according to the method of the invention, mention may be made of *Escherichia coli* using alcohol dehydrogenase ADHE as quantification marker or a peptide belonging to this protein. The sequence of the ADHE protein is the sequence SEQ ID No. 1:

```
SEQ ID No. 1:
MAVTNVAELNALVERVKKAQREYASFTQEQVDKIFRAAALAAADARI

PLAKMAVAESGMGIVEDKVIKNHFASEYIYNAYKDEKTCGVLSEDDT

EGTITIAEPIGIICGIVPTTNPTSTAIFKSLISLKTRNAIIFSPHPR

AKDATNKAADIVLQAAIAAGAPKDLIGWIDQPSVELSNALMHHPDIN

LILATGGPGMVKAAYSSGKPAIGVGAGNTPVVIDETADIKRAVASVL

MSKTFDNGVICASEQSVVVVDSVYDAVRERFATHGGYLLQGKELKAV

QDVILKNGALNAAIVGQPAYKIAELAGFSVPENTKILIGEVTVVDES

EPFAHEKLSPTLAMYRAKDFEDAVEKAEKLVAMGGIGHTSCLYTDQD
```

-continued
```
NQPARVSYFGQKMKTARILINTPASQGGIGDLYNFKLAPSLTLGCGS

WGGNSISENVGPKHLINKKTVAKRAENMLWHKLPKSIYERRGSLPIA

LDEVITDGHKRALIVTDRFLENNGYADQITSVLKAAGVETEVFFEVE

ADPTLSIVRKGAELANSFKPDVIIALGGGSPMDAAKIMWVMYEHPET

HFEELALREMDIRKRIYKEPKMGVKAKMIAVTTTSGTGSEVTPFAVV

TDDATGQKYPLADYALTPDMAIVDANLVMDMPKSLCAFGGLDAVTHA

MEAYVSVLASEFSDGQALQALKLLKEYLPASYHEGSKNPVARERVHS

AATIAGIAFANAFLGVCHSMAHKLGSQFHIPHGLANALLICNVIRYN

ANDNPTKQTAFSQYDRPQARRRYAEIADHLGLSAPGDRTAAKIEKLL

AWLETLKAELGIPKSIREAGVQEADFLANVDKLSEDAFDDQCTGANP

RYPLISELKQILLDTYYGRDYVEGETAAKKEAAPAKAEKKAKKSA.
```

A peptide derived from the ADHE protein is preferably the peptide of sequence SEQ ID No. 2, as defined below:

| Peptide SEQ ID No. | Amino acid sequence | Position of the peptide in the protein |
|---|---|---|
| SEQ ID No. 2 | DYVEGETAAK | 866-875 |

Another example of bacterial species that can be quantified according to the method of the invention consists of *Staphylococcus aureus* using the GUAA-STAAN GMP synthase (glutamine-hydrolyzing) protein as quantification marker or a peptide belonging to this protein. The sequence of the GUAA-STAN protein is the sequence SEQ ID No. 3:

```
SEQ ID No. 3:
MEMAKEQELILVLDFGSQYNQLITRRIREMGVYSELHDHEISIEEIK

KMNPKGIILSGGPNSVYEEGSFTIDPEIYNLGIPVLGICYGMQLTTK

LLGGKVERANEREYGKAIINAKSDELFAGLPAEQTVWMSHSDKVIEI

PEGFEVIADSPSTDYAAIEDKKRRIYGVQFHPEVRHTEYGNDLLNNF

VRRVCDCKGQWTMENFIEIEIEKIRQRVGDRRVLCAMSGGVDSSVVA

VLLHKAIGDQLTCIFVDHGLLRKGEGDMVMEQFGEGFNMNIIRVNAK

DRFMNKLKGVSDPEQKRKIIGNEFVYVFDDEASKLKGVDFLAQGTLY

TDVIESGTKTAQTIKSHHNVGGLPEDMEFELIEPINTLFKDEVRKLG

IELGIPEHLVWRQPFPGPGLGIRVLGEITEDKLEIVRESDAILRQVI

REEGLEREIWQYFTVLPNIQSVGVMGDYRTYDHTVGIRAVTSIDGMT

SDFARIDWEVLQKISSRIVNEVDHVNRVVYDITSKPPSTIEWE.
```

A peptide derived from the GUAA-STAN protein is preferably the peptide of sequence SEQ ID No. 4, as defined below:

| Peptide SEQ ID No. | Amino acid sequence | Position of the peptide in the protein |
|---|---|---|
| SEQ ID No. 4 | LGIELGIPEHLVWR | 375-388 |

Another example of bacterial species that can be quantified according to the method of the invention consists of *Pseudomonas aeruginosa* using the A3LLD0_PSEAI Insulin-cleaving metalloproteinase protein as quantification marker or a peptide belonging to this protein. The sequence of the A3LLD0_PSEAI protein is the sequence SEQ ID No. 5:

SEQ ID No. 5:
MTRMPLATASLLALAISLAGCGDDKKAEAPATPAASTQPAAPAAAPA

AKVDEAAAKAVIKNYADLAEATFADALSTAKDLQKAIDAFLAKPDAE

TLKAAKEAWFAARTPYSQSEAFREGNAIIDDWEGQVNAWPLDEGLID

YVAKDYQHALGNPGATANIVANTEIQVGEDKIDVKEITGEKLASLNE

LGGSEANVATGYHAIEFLLWGQDLNGTGPGAGNRPATDYAQGKDCTG

GHCDRRAAYLKAVTDLLVSDLEYMAGQWKAGVADNYRAKLEAEPVDT

GLRKMFFGMGSLSLGELAGERMKVALEANSTEDEHDCFSDDTHHTLF

FNGKSIRNIYLGEYKRIDGSVVKGPSLADLVAKADAAANDTLKADLA

DTEAKLQAIVDSAEKDGVHFDQMIAPDNKDGQQKIRDAIAALVKQTG

AIEQAAGKLGIQDLKPDNADHEF.

A peptide derived from the A3LLD0_PSEAI protein is preferably the peptide of sequence SEQ ID No. 6, as defined below:

| Peptide SEQ ID No. | Amino acid sequence | Position of the peptide in the protein |
| --- | --- | --- |
| SEQ ID No. 6 | ADAAANDTLK | 363-372 |

By way of the other bacterial groups that can be quantified according to the method of the invention, mention may be made, as an example of a family of bacteria, of the Enterobacteriaceae, using as quantification marker the EFG (Elongation Factor G) protein or a peptide belonging to this protein. The sequence of the EFG protein is the sequence SEQ ID No. 7:

SEQ ID No. 7:
MARTTPIARYRNIGISAHIDAGKTTTTERILFYTGVNHKIGEVHDGA

ATMDWMEQEQERGITITSAATTAFWSGMAKQYEPHRINIIDTPGHVD

FTIEVERSMRVLDGAVMVYCAVGGVQPQSETVWRQANKYKVPRIAFV

NKMDRMGANFLKVVNQIKTRLGANPVPLQLAIGAEEHFTGVVDLVKM

KAINWNDADQGVTFEYEDIPADMVELANEWHQNLIESAAEASEELME

KYLGGEELTEAEIKGALRQRVLNNEIILVTCGSAFKNKGVQAMLDAV

IDYLPSPVDVPAINGILDDGKDTPAERHASDDEPFSALAFKIATDPF

VGNLTFFRVYSGVVNSGDTVLNSVKAARERFGRIVQMHANKREEIKE

VRAGDIAAAIGLKDVTTGDTLCDPDAPIILERMEEPEPVISIAVEPK

TKADQEKMGLALGRLAKEDPSFRVWTDEESNQTIIAGMGELHLDIIV

DRMKREFNVEANVGKPQVAYRETIRQKVTDVEGKHAKQSGGRGQYGH

VVIDMYPLEPGSNPKGYEFINDIKGGVIPGEYIPAVDKGIQEQLKAG

PLAGYPVVDMGIRLHFGSYHDVDSSELAFKLAASIAFKEGFKKAKPV

LLEPIMKVEVETPEENTGDVIGDLSRRRGMLKGQESEVTGVKIHAEV

PLSEMFGYATQLRSLTKGRASYTMEFLKYDEAPSNVAQAVIEARGK.

A peptide derived from the EFG protein is preferably the peptide of sequence SEQ ID No. 8, as defined below:

| Peptide SEQ ID No. | Amino acid sequence | Position of the peptide in the protein |
| --- | --- | --- |
| SEQ ID No. 8 | AGDIAAAIGLK | 379-389 |

Other microorganism groups can be quantified with the method according to the invention. In particular, some proteins known to be relatively ubiquitous can be used to quantify microorganisms obtained using pure cultures.

Entirely advantageously, according to the second subject of the invention, such proteins can also make it possible to measure the level of expression of proteins or peptides of interest, such as for example bacterial enzymes involved in antibiotic resistance mechanisms. The proteins or peptides serving as quantification markers make it possible to correlate the amount of proteins of interest with the amount of bacteria which express them.

This is the case, for example, with the RL29, RL22 and RS19 proteins which are ribosomal proteins that are constitutively expressed. These proteins, or peptides derived from these proteins, can make it possible to quantify, for example, bacteria of the *Enterococcus* genus and in particular *Enterococcus faecalis*.

The RL29 ribosomal protein is part of the 50S subunit. It is involved in the translation step. The sequence of the RL29 protein is the sequence SEQ ID No. 9:

SEQ ID No. 9:
MKVKEIRELTTAEMLDKEKQLKEELFNLRFQLATGQLENTARIKEVR

QSIARIKTVLREQAN.

A peptide from the RL29 protein is preferably the peptide of sequence SEQ ID No. 10, as defined below:

| Peptide SEQ ID No. | Amino acid sequence | Position of the peptide in the protein |
| --- | --- | --- |
| SEQ ID No. 10 | FQLATGQLENTAR | 30-42 |

The RL22 ribosomal protein is also part of the 50S subunit. This protein binds specifically to the 23D ribosomal RNA. It plays an important role in the first steps of assembly of the two subunits of the ribosome. The sequence of the RL22 protein is the sequence SEQ ID No. 11:

SEQ ID No. 11:
MSEQITSAKATAKTVRTSPRKARLVIDLIRGKSVADAISILKFTPNK

SAGIIEKVLMSAVANAENNFDLDVESLVVSEAFVNEGPTMKRFRPRA

KGSASPINKRTSHITVVVTEK.

A peptide derived from the RL22 protein is preferably the peptide of sequence SEQ ID No. 12, as defined below:

| Peptide SEQ ID No. | Amino acid sequence | Position of the peptide in the protein |
|---|---|---|
| SEQ ID No. 12 | LVIDLIR | 24-30 |

The RS19 ribosomal protein is part of the 30S subunit. This protein forms a complex with the RL13 protein binding strongly to the 16S ribosomal RNA. The sequence of the RS19 protein is the sequence SEQ ID No. 13:

SEQ ID No. 13:
MGRSLKKGPFVDDHLMKKVEAQQGAEKKKVIKTWSRRSTIFPSFVGFTIA

VYDGRKHVPVYIQEDMVGHKLGEFAPTRTYRGHVADDKKTKR.

A peptide derived from the RS19 protein is preferably the peptide of sequence SEQ ID No. 14, as defined below:

| Peptide SEQ ID No. | Amino acid sequence | Position of the peptide in the protein |
|---|---|---|
| SEQ ID No. 14 | LGEFAPTR | 71-78 |

In *Klebsiella pneumoniae*, other proteins can be used as quantification markers. This is the case, for example, with the aconitate hydratase protein (Uniprot reference W9BG99), the alanine-tRNA ligase protein (Uniprot reference W9BNB5) and the phosphoenolpyruvate phosphotransferase protein of the PTS system (Uniprot reference W1H324).

The sequence of the aconitate hydratase protein is the sequence SEQ ID No. 15:

SEQ ID No. 15:
MSSTLREASKDTLQVNDKTWHYYSLPLAEKQLGEISRLPKSLKVLMENLL

RWQDGDSVTEEDIRALAGWLQQAHADREIAYRPARVLMQDFTGVPAVVDL

AAMREAVKRLGGDTAKVNPLSPVDLVIDHSVTVDRFGDDEAFEDNVRLEM

ERNHERYAFLRWGQQAFSRFSVVPPGTGICHQVNLEYLGRAVWSEEVNGQ

WMAWPDTLVGTDSHTTMINGLGVLGWGVGGIEAEAAMLGQPVSMLIPDVV

GFKLSGKLREGITATDLVLTVTQMLRQHGVVGKFVEFYGDGLDTLPLADR

ATIANMAPEYGATCGFFPIDDVTLSYMRLSGRSEEQVALVEAYAKAQGMW

RQPGDEPVFTSTLALDMSSVEASLAGPKRPQDRVALGDVPKAFAASGELE

VNHLQRQRQPVDYTLNGHHYSLPDGAVAIAAITSCTNTSNPSVLMAAGLL

AKKAVERGLQPQPWVKASLAPGSKVVSDYLAHAGLTPYLDQLGFNLVGYG

CTTCIGNSGPLPEPIEEAIKKGDLTVGAVLSGNRNFEGRIHPLVKTNWLA

SPPLVVAYALAGNMNIDLTREPLGQGKNGEPVYLKDIWPSGEEIARAVEQ

VSTEMFRKEYAEVFSGTEEWKAIKVEASDTYDWQEDSTYIRLSPFFDEMG

AEPLPVEDIRGARILAMLGDSVTTDHISPAGSIKADSPAGRYLQEHGVAR

RDENSYGSRRGNHEVMMRGTFANIRIRNEMVPGVEGGMTRHLPDPEPMAI

YDAAMLYKAEGTPLAVIAGKEYGSGSSRDWAAKGPRLLGIRVVIAESFER

IHRSNLIGMGILPLEFPQGVTRKTLRLTGEERIDISNLQSLQPGATVPVT

LTRADGSQEAIPCRCRIDTATELTYYRNDGILHYVIRNML.

A peptide derived from the aconitate hydratase protein is preferably the peptide of sequence SEQ ID No. 16, as defined below:

| Peptide SEQ ID No. | Amino acid sequence | Position of the peptide in the protein |
|---|---|---|
| SEQ ID No. 16 | AFAASGELEVNHLQR | 392-407 |

The sequence of the alanine-tRNA ligase protein is the sequence SEQ ID No. 17:

SEQ ID No. 17:
MSKSTAEIRQAFLDFFHSKGHQVVASSSLVPHNDPTLLFTNAGMNQFKDV

FLGLDKRNYSRATTAQRCVRAGGKHNDLENVGYTARHHTFFEMLGNFSFG

DYFKQDAIKYAWELLTGENWFALPKEKLWVTVYETDDEAFDIWANEVGVP

RERIIRIGDNKGAPFASDNFWQMGDTGPCGPCTEIFFDHGDHIWGGPPGS

PEEDGDRYIEIWNIVFMQFNRQADGTMEPLPKPSVDTGMGLERIAAVLQH

VNSNYDIDLFRDLIASVAKVTGATDLTNKSLRVIADHIRSCAFLVADGVI

PSNENRGYVLRRIIRRAIRHGNMLGAKDTFFWKLVAPLIDVMGSAGDELK

QQQAQVEQVLKTEEEQFARTLERGLALLDEELSKLKGDTLDGETAFRLYD

TYGFPVDLTADVCRERNIKVDEAGFEAAMEEQRRRARESSGFGADYNAMI

RVDGASEFKGYDHLELNGKVTALFIDGKAVDSVSAGQEAVVILDQTPFYA

ESGGQVGDKGELKGAGFSFAVSDTQKYGQAIGHIGKVASGTLKVGDAVQA

DVDEARRQRIRLNHSATHLMHAALRQVLGTHVAQKGSLVNDKALRFDFSH

FEAMKPEEIRAVEDLVNAQIRRNLAIETNIMDIDAARASGAMALFGEKYD

DRVRVLRMGDFSTELCGGTHAARTGDIGLFRITSESGTAAGVRRIEAVTG

EGAMAILHAQSDQLNDIAQLLKGDSHNLGEKVRAALERTRQLEKELQQLK

EQAAAQESANLSSKAEEINGVKLLVSELTGVEPKMLRTMVDDLKNQLGST

IVVLATVADGKVSLIAGVSKDVTDRVKAGELVGMVAQQVGGKGGGRPDMA

QAGGTDASALPAALASVKGWVSAKL.

A peptide derived from the alanine-tRNA ligase protein is preferably the peptide of sequence SEQ ID No. 18, as defined below:

| Peptide SEQ ID No. | Amino acid sequence | Position of the peptide in the protein |
|---|---|---|
| SEQ ID No. 18 | LLVSELTGVEPK | 773-785 |

The sequence of the phosphoenolpyruvate phosphotransferase protein of the PTS system is the sequence SEQ ID No. 19:

SEQ ID No. 19:
MNNQVLINPSNEQIEALRSLQAQVAEEKAELAKLKDLPAITLDGHQVEVC

ANIGTVRDVEGAERNGAEGVGLYRTEFLFMDRDALPTEEEQFAAYKAVAE

ACGSQAVIVRTMDIGGDKELPYMNFPKEENPFLGWRAVRIAMDRKEILRD

QVRAILRASAFGKLRIMFPMIISVEEVRALKKEIEIYKQELRDEGKAFDE

SIEIGVMVETPAAATIARHLAKEVDFFSIGTNDLTQYTLAVDRGNDMISY

LYQPMSPSVLNLIKQVIDASHAEGKWTGMCGELAGDERATLLLLGMGLDE

FSMSAISIPRIKKIIRNTNFEDAKVLAEQALAQPTTDELMTLVNKFIEEK

TIC.

A peptide derived from the phosphoenolpyruvate phosphotransferase protein is preferably the peptide of sequence SEQ ID No. 20, as defined below:

| Peptide SEQ ID No. | Amino acid sequence | Position of the peptide in the protein |
|---|---|---|
| SEQ ID No. 20 | SLQAQVAEEK | 19-29 |

When the quantification markers of the microorganism groups are of protein origin, upstream of the detection by mass spectrometry, the sample to be analyzed is preferentially treated beforehand in order to generate peptides from all of the proteins present in the sample in order to fragment these proteins into peptides, for example by digestion with a proteolytic enzyme (protease), or by the action of a chemical reagent. Indeed, protein cleavage can be carried out by a physiochemical treatment, by a biological treatment or by a combination of the two treatments. Among the usable treatments, mention may be made of the treatment with hydroxyl radicals, in particular with $H_2O_2$. Treatment with hydroxyl radicals causes a cleavage of the peptide bonds which takes place randomly on any peptide bond of the protein. The hydroxyl radical concentration conditions the number of cleavages performed and thus the length of the peptide fragments obtained. Other chemical treatments can also be used, such as, for example, treatment with cyanogen bromide (CNBr) which specifically splits the peptide bonds at the carboxylic group of the methionyl residues. It is also possible to carry out a partial acid cleavage at the aspartyl residues by heating, at 1000° C., a solution of proteins in trifluoroacetic acid.

Treatment of the proteins by enzymatic digestion is nevertheless preferred compared with physiochemical treatment since it gives better preservation of the structure of the proteins, and is easier to control. The term "enzymatic digestion" is intended to mean the single or combined action of one or more enzymes under appropriate reaction conditions. The enzymes which perform proteolysis, called proteases, cut proteins at specific sites. Each protease generally recognizes a sequence of amino acids within which it always performs the same cut.

Some proteases recognize a single amino acid or a sequence of two amino acids between which they perform a cleavage; other proteases recognize only longer sequences. These proteases may be endoproteases or exoproteases. Among known proteases, mention may be made of, as described in WO-A-2005/098017:

specific enzymes, such as trypsin which splits the peptide bond at the carboxylic group of Arg and Lys residues, endolysin which cleaves the peptide bond of the —CO group of lysines, chymotrypsin which hydrolyzes the peptide bond at the carboxylic group of aromatic residues (Phe, Tyr and Trp), pepsin which cleaves at the $NH_2$ group of aromatic residues (Phe, Tyr and Trp), the V8 protease of the V8 strain of *Staphylococcus aureus*, which cleaves the peptide bond at the carboxylic group of the Glu residue;

non-specific enzymes, such as thermolysin originating from the *Bacillus thermoproteolyticus* bacterium which hydrolyzes the peptide bond of the $NH_2$ group of hydrophobic amino acids (Xaa-Leu, Xaa-Ile, Xaa-Phe), subtilisin and pronase which are bacterial proteases which hydrolyze virtually all the bonds and can convert proteins into oligopeptides under controlled reaction conditions (enzyme concentration and reaction time).

Several proteases can be used simultaneously, if their modes of action are compatible. They can also be used successively. In the context of the invention, the digestion of the sample is preferably carried out by the action of a protease enzyme, for example trypsin.

The generation of peptides using a chemical reagent of a protease can be obtained by simple reaction in solution. It can also be carried out with a microwave oven [11], or under pressure [12], or else with an ultrasound device [13]. In the latter three cases, the protocol will be much faster.

Among the peptides thus obtained, the peptides specific for the protein are called proteotypic peptides. It is these that will be assayed by mass spectrometry.

According to one embodiment of the invention, the quantification markers are peptides corresponding to a protein of the bacterial group to be quantified. In particular, said proteins are digested into peptides, preferably with an enzyme, more preferably with trypsin.

Likewise, the sample containing quantification markers of protein origin can also be pretreated for purification purposes. When the markers are of protein origin, this purification pretreatment can be carried out before or after the step of generating peptides as previously described.

The sample purification pretreatment is widely known to those skilled in the art and may in particular implement centrifugation, filtration, electrophoresis or chromatography techniques. These separative techniques can be used alone or combined with one another in order to obtain a multidimensional separation. For example, a multidimensional chromatography can be used by combining a separation by ion exchange chromatography with reverse-phase chromatography, as described by T. Fortin et al. [14], or H. Keshishian et al. [15]. In these publications, the chromatographic medium may be in a column or in a cartridge (solid-phase extraction).

The electrophoretic or chromatographic fraction (or the retention time in one- or multidimensional chromatography) of the proteotypic peptides is characteristic of each peptide and the implementation of these techniques thus makes it possible to select the proteotypic peptide(s) to be assayed. Such a fractionation of the peptides generated makes it possible to increase the specificity of the subsequent assaying by mass spectrometry.

An alternative to electrophoresis or chromatography techniques, for fractionating the peptides, consists in specifically purifying the N-glycopeptides ([16] and patent application WO-A-2008/066629). Nevertheless, such a purification only allows the quantification of the peptides having undergone a post-translational modification of N-glycosylation type. However, not all proteins are glycosylated, thereby limiting its use.

The mass spectrometry to be implemented in the process of the invention is widely known to those skilled in the art as a powerful tool for the analysis, detection and quantification of various types of molecules. Generally, any type of molecule that can be ionized can be detected and quantified as a function of its molecular mass using a mass spectrometer. Depending on the nature of the molecule to be detected, of protein or metabolic origin, certain mass spectrometry techniques may be more suitable. Nevertheless, whatever the mass spectrometry method used for the detection, the latter comprises a step of ionizing the target molecule into "molecular" ions, in the present case a step of ionizing the quantification markers, and a step of separating the molecular ions obtained as a function of their mass.

All mass spectrometers thus comprise:
- an ionization source intended to ionize the markers present in the sample to be analyzed, that is to say to give these markers a positive or negative charge;
- a mass analyzer intended to separate the ionized markers, or molecular ions, as a function of their mass to charge (m/z) ratio;
- a detector intended to measure the signal produced either directly by the molecular ions, or by ions produced from the molecular ions. This signal can be used qualitatively or quantitatively, as detailed below.

The ionization step required for using a mass spectrometer can be carried out by any process known to those skilled in the art. The ionization source makes it possible to bring the molecules to be assayed into a gaseous and ionized state. An ionization source can be used either in positive mode for studying positive ions, or in negative mode for studying negative ions. Several types of sources exist and will be used depending on the result sought and the molecules analyzed. Mention may in particular be made of:
- electron ionization (EI), chemical ionization (CI) and desorption chemical ionization (DCI),
- fast atom bombardment (FAB), metastable atom bombardment (MAB) or ion bombardment (SIMS, LSIMS),
- inductively coupled plasma (ICP),
- atmospheric pressure chemical ionization (APCI) and atmospheric pressure photoionization (APPI),
- electrospray (ESI),
- desorption electrospray ionization (DESI) or nanospray desorption electrospray ionization (nanoDESI),
- laser ablation electrospray ionization (LAESI),
- rapid evaporation ionization (REIMS),
- ionization-desorption by interaction with metastable species (DART).

In particular, the ionization can be carried out as follows: the sample containing the target molecules is introduced into an ionization source, where the molecules are ionized in the gaseous state and thus converted into molecular ions which correspond to the initial molecules. An ionization source of electrospray (ESI for ElectroSpray Ionization) type makes it possible to ionize a molecule while at the same time making it go from a liquid state to a gaseous state. The molecular ions obtained then correspond to the molecules present in the liquid state, with, in positive mode, one, two or even three additional protons or more, and thus carry one, two or even three charges or more. For example, when the target molecule is a protein, ionization of the proteotypic peptides obtained after fractionation of the target protein, by virtue of a source of electrospray type operating in positive mode, results in polypeptide ions in the gaseous state, with one, two or even three additional protons or more and which thus carry one, two or even three charges or more, and makes it possible to go from a liquid state to a gaseous state [17]. This type of source is particularly suitable when the target molecules or proteotypic peptides obtained are separated beforehand by reverse-phase liquid chromatography. Nevertheless, the ionization yield of the molecules present in the sample can vary according to the concentration and the nature of the various species present. This phenomenon results in a matrix effect well known to those skilled in the art.

The mass analyzer in which the step of separating the ionized markers as a function of their mass/charge (m/z) ratio is carried out is any mass analyzer known to those skilled in the art. Mention may be made of low-resolution analyzers, of the quadrupole (Q), 3D ion trap (IT) or linear ion trap (LIT) type, and high-resolution analyzers, which make it possible to measure the exact mass of the analytes and which use in particular the magnetic sector coupled to an electrical sector, time-of-flight (TOF), orbitrap, and Fourier transform ion cyclotron resonance (FT-ICR).

During the separation of the molecular ions as a function of their m/z ratio, several successive MS separation steps can be carried out. When two successive MS separation steps are carried out, the analysis is called MS/MS or $MS^2$. When three successive MS separation steps are carried out, the analysis is called MS/MS/MS or $MS^3$ and, more generally, when n successive MS separation steps are carried out, the analysis is called $MS^n$.

Among the techniques implementing several successive separations, the SRM (Selected Reaction Monitoring) mode in the case of detection or assaying of a single target molecule, or else MRM (Multiple Reaction Monitoring) mode in the case of detection or assaying of several target molecules, are particular uses of $MS^2$ separation. Likewise, the $MRM^3$ mode is a particular use of separation by MS/MS/MS. The term then used is targeted mass spectrometry.

In the case of a detection in single MS mode, it is the mass/charge ratio of the molecular ions obtained which is correlated with the target molecule to be detected.

In the case of a detection in MS/MS mode, essentially two steps are added, compared with an MS assay, which steps are:
a fragmentation of the molecular ions, then called precursor ions, to give ions termed $1^{st}$-generation fragment ions, and
a separation of the ions termed $1^{st}$-generation fragment ions as a function of their mass $(m/z)_2$, the ratio $(m/z)_1$ corresponding to the ratio (m/z) of the precursor ions.

It is then the mass/charge ratio of the $1^{st}$-generation fragment ions thus obtained that is correlated with the target molecule to be detected. The term "first-generation fragment ion" is intended to mean an ion derived from the precursor ion, following a fragmentation step, and the mass to charge ratio m/z of which is different from the precursor ion.

The $(m/z)_1$ and $(m/z)_2$ pairs are called transitions and are representative of the characteristic ions to be detected.

The choice of the characteristic ions that are detected in order to be correlated with the target molecule is made by those skilled in the art according to standard methods. Their selection will advantageously result in the most sensitive, most specific and most robust assays possible, in terms of reproducibility and reliability. In the methods developed for the selection of proteotypic peptides $(m/z)_1$, and of first-generation fragment $(m/z)_2$, the choice is essentially based on the intensity of the response. For more details, reference may be made to V. Fusaro et al. [18]. Commercial software products, such as the MIDAS and MRM Pilot software products from Applied Biosystems or else MRMaid [19] may be used by those skilled in the art in order to allow them to predict all the possible transition pairs. They may also call upon a database called PeptideAtlas, constructed by F. Desiere et al. [20] in order to compile all of the peptide MRM transitions described by the scientific community. This PeptideAtlas base is freely accessible on the Internet. It is also possible to use databases for non-protein molecules, such as, for example, the database accessible through the Cliquid software from AB Sciex (Framingham, Mass., United States of America).

An alternative approach for selecting the proteotypic peptides, $(m/z)_1$ and $(m/z)_2$, consists in using the MS/MS fragmentation spectra obtained during other studies. These studies may for example be the phases of discovering and identifying the biomarkers by proteomic analysis. This approach was proposed by Thermo Scientific during a users meeting [19]. It makes it possible to generate a list of candidate transitions from the peptides identified experimentally by the SIEVE software (Thermo Scientific). Certain criteria have been explained in detail by J. Mead et al. [19] for the choice of the $(m/z)_1$ and $(m/z)_2$ ions and are explained in detail below:

Peptides with internal cleavage sites, that is to say with internal lysine or arginine, must be avoided, unless the lysine or the arginine is followed by proline.

Peptides with asparagine or glutamine must be avoided since they can become deaminated.

Peptides with N-terminal glutamine or N-terminal glutamic acid must be avoided since they can spontaneously cyclize.

Peptides with methionine must be avoided since they can be oxidized.

Peptides with cysteine must be avoided since they can be modified non-reproducibly during an optional step of denaturation, reduction and blocking of thiol functions.

Peptides with proline can be considered to be favorable because they generally produce intense fragments in MS/MS with a very predominant single peak. However, a very predominant single fragment does not make it possible to validate the identity of the transition in a complex mixture. Indeed, only the simultaneous presence of several characteristic fragments makes it possible to verify that the precursor ion sought is indeed detected.

Peptides having a proline adjacent to the C-terminal (position n-1) or in the second position relative to the C-terminal (position n-2) are to be avoided since, in this case, the size of the first-generation fragment peptide is generally considered to be too small to be sufficiently specific.

The selection of fragments having a mass greater than the precursor is to be favored in order to promote specificity. For this, it is necessary to select a doubly charged precursor ion and to select the most intense first-generation fragment ion having a mass greater than the precursor, that is to say a singly charged first-generation fragment ion.

The fragmentation of the selected precursor ions is carried out in a fragmentation cell such as the models of triple quadrupole type [21], or of ion trap type [22], or else of time-of-flight (TOF) type [23], which also allow separation of the ions. The fragmentation(s) will conventionally be carried out by collision with an inert gas such as argon or nitrogen, within an electric field, by photoexcitation or photodissociation using an intense light source, collision with radical electrons or species, by application of a potential difference, for example in a time-of-flight tube, or by any other activation mode. The characteristics of the electric field condition the intensity and the nature of the fragmentation. Thus, the electric field applied in the presence of an inert gas, for example in a quadrupole, conditions the collision energy given to the ions. This collision energy will be optimized, by those skilled in the art, in order to increase the sensitivity of the transition to be assayed. By way of example, it is possible to vary the collision energy between 5 and 180 eV in q2 in a QTRAP® 5500 mass spectrometer from AB Sciex (Framingham, Mass., United States of America). Likewise, the duration of the collision step and the excitation energy within, for example, an ion trap will be optimized, by those skilled in the art, in order to give the most sensitive assay. By way of example, it is possible to vary this duration, called excitation time, between 0.010 and 50 ms and the excitation energy between 0 and 1 (arbitrary unit) in Q3 in a QTRAP® 5500 mass spectrometer.

Finally, the detection of the characteristic ions selected is carried out conventionally, in particular by means of a detector and a treatment system. The detector collects the ions and produces an electrical signal, the intensity of which depends on the amount of ions collected. The signal obtained is then amplified so that it can be computer-processed. A data processing computer assembly makes it possible to convert the information received by the detector into a mass spectrum.

The principle of the SRM mode, or else of the MRM mode, is to specifically select a precursor ion, to fragment it, and then to specifically select one of its fragment ions. For such applications, devices of the triple quadrupole type or triple quadrupole with ion trap hybrids are generally used.

In the case of a triple quadrupole device (Q1q2Q3) used in $MS^2$ mode, with a view to assaying or detecting a target protein, the first quadrupole (Q1) makes it possible to filter the molecular ions, corresponding to the proteotypic peptides characteristic of the protein to be assayed and obtained during a prior digestion step, as a function of their mass to charge (m/z) ratio. Only the peptides having the mass/charge ratio of the proteotypic peptide sought, said ratio being called $(m/z)_1$, are transmitted to the second quadrupole (q2) and act as precursor ions for the subsequent fragmentation. The q2 analyzer makes it possible to fragment the peptides of mass/charge ratio $(m/z)_1$ into first-generation fragment ions. The fragmentation is generally obtained by collision of the precursor peptides with an inert gas, such as nitrogen or argon in q2. The first-generation fragment ions are transmitted to a third quadrupole (Q3) which filters the first-generation fragment ions as a function of a specific mass to charge ratio, said ratio being called $(m/z)_2$. Only the first-generation fragment ions having the mass/charge ratio of a fragment characteristic of the proteotypic peptide sought $(m/z)_2$ are transmitted to the detector in order to detected, or even quantified.

This operating mode has a double selectivity, in relation, on the one hand, to the selection of the precursor ion and, on the other hand, to the selection of the first-generation fragment ion. Mass spectrometry in SRM or MRM mode is thus advantageous for the quantification.

When the mass spectrometry carried out in the method of the invention is tandem mass spectrometry ($MS^2$, $MS^3$, $MS^4$ or $MS^5$), several mass analyzers can be coupled together. For example, a first analyzer separates the ions, a collision cell makes it possible to fragment the ions, and a second analyzer separates the fragment ions. Some analyzers, such as ion traps or FT-ICR, constitute several analyzers in one and make it possible to fragment the ions and to analyze the fragments directly.

According to preferred embodiments of the invention, the method of the invention comprises one or more of the following characteristics:

the mass spectrometry, carried out in order to quantify a bacterial group, is MS/MS spectrometry, which has the advantage of generating a fragment specific to the molecule to be detected or to be quantified, and thus of bringing great specificity to the assay method;

the MS/MS spectrometry is a quantitative mass spectrometry method, which can be a DIA (Data Independent Analysis) method [25] comprising, inter alia, SWATH (Sequential Windows Acquisition of All THeoretical fragments) [26], or $MS^E$ [27], a DDA (Data Dependent Acquisition) method or a PRM (Parallel Reaction Monitoring), SRM or MRM method.

MRM, which has the advantage of using an analysis cycle time in the mass spectrometer of a few tens of milliseconds, makes it possible to detect or quantify with great sensitivity, and in multiplex fashion, a large number of different molecules.

DIA has the advantage of allowing the identification of molecules and the quantification with good sensitivity, and specificity, and with an even greater multiplexing capacity.

One of the advantages of the use of mass spectrometry lies in the fact that it is particularly useful for quantifying molecules, in the present case the quantification markers of at least one bacterial group. To do this, the detected current intensity is used, which is proportional to the amount of target molecule. The current intensity thus measured may be used as a quantitative measurement making it possible to determine the amount of target molecule present, which is characterized by its expression in International System (SI) units of $mol/m^3$ or $kg/m^3$ type, or by the multiples or submultiples of these units, or by the usual derivatives of SI units, including multiples or submultiples thereof. By way of nonlimiting example, units such as ng/ml or fmol/l are units which characterize a quantitative measurement.

A calibration is nevertheless required in order to be able to correlate the area of the peak measured, corresponding to the intensity of current induced by the ions detected, with the amount of target molecule to be assayed. For this, the calibrations conventionally used in mass spectrometry may be used, in the context of the invention. MRM assays are conventionally calibrated by means of external standards or, preferably, by means of internal standards as described by T. Fortin et al. [14]. In the case where the target molecule is a proteotypic peptide, making it possible to assay a protein of interest, the correlation between the quantitative measurement and the amount of target proteotypic peptide, and subsequently of the protein of interest, is obtained by calibrating the signal measured relative to a standard signal for which the amount to be assayed is known. The calibration can be carried out by means of a calibration curve, for example obtained by successive injections of standard proteotypic peptide at various concentrations (external calibration), or preferentially by internal calibration using a heavy peptide, as internal standard, for example in accordance with the AQUA, QconCAT or PSAQ methods described in detail below. The term "heavy peptide" is intended to mean a peptide corresponding to the proteotypic peptide, but in which one or more of the carbon 12 ($^{12}C$) atoms is (are) replaced with carbon 13 ($^{13}C$), and/or one or more nitrogen 14 ($^{14}N$) atoms is (are) replaced with nitrogen 15 ($^{15}N$).

The use of heavy peptides, as (AQUA) internal standards, has also been proposed in patent application US 2004/0229283. The principle is to artificially synthesize proteotypic peptides with amino acids comprising isotopes that are heavier than the usual natural isotopes. Such amino acids are obtained, for example, by replacing some of the carbon 12 ($^{12}C$) atoms with carbon 13 ($^{13}C$), or by replacing some of the nitrogen 14 ($^{14}N$) atoms with nitrogen 15 ($^{15}N$). The artificial peptide, also called heavy peptide or AQUA peptide, thus synthesized has rigorously the same physicochemical properties as the natural peptide, also called light peptide; the only difference between these two peptides lies in their mass, which is higher for the heavy peptide and lower for the light peptide. It is generally added, at a given concentration, to the sample, upstream of the assay by mass spectrometry, for example between the treatment leading to the cleavage of the proteins of the sample of interest and the fractionation of the peptides obtained after the treatment step. As a result, the AQUA peptide is copurified with the natural peptide to be assayed, during the fractionation of the peptides. The two peptides are thus injected simultaneously into the mass spectrometer, for the assay. They then undergo the same ionization yields in the source. The comparison of the areas of the peaks of the natural peptide and AQUA peptide, the concentration of which is known, makes it possible to calculate the concentration of the natural peptide and to thus work back to the concentration of the protein to be assayed. A variant of the AQUA technique has been proposed by J.-M. Pratt et al. [35] under the name QconCat. This variant is also described in patent application WO 2006/128492. It consists in concatenating various AQUA peptides and in producing the artificial polypeptide in heavy recombinant protein form. The recombinant protein is synthesized with amino acids comprising heavy isotopes. In this way, it is possible to obtain a standard for calibrating the simultaneous assaying of several proteins at a lower cost. The QconCAT standard is added from the beginning, upstream of the treatment leading to the cleavage of the proteins and before the steps of protein fractionation, of denaturation, of reduction and then of blocking of the thiol functions of the proteins, if said functions are present. The QconCAT standard thus undergoes the same treatment cycle leading to cleavage of the proteins as the natural protein, thereby making it possible to take into account the yield of the treatment step leading to the cleavage of the proteins. Indeed, the treatment, in particular by digestion, of the natural protein may not be complete. In this case, the use of an AQUA standard would result in the amount of natural protein being underestimated. For an absolute assay, it may thus be important to take into account the yields of treatment leading to the cleavage of the proteins. However, V. Brun et al. [36] have shown that, sometimes, the QconCAT standards do not exactly reproduce the yield of treatment, in particular by digestion, of the natural protein, doubtless because of a different three-dimensional conformation of the QconCAT protein.

V. Brun et al. [36] have therefore proposed using a method called PSAQ and described in patent application WO 2008/145763. In this case, the internal standard is a recombinant protein, having the same sequence as the natural protein, but synthesized with heavy amino acids. The synthesis is carried out ex-vivo with heavy amino acids. This standard has rigorously the same physicochemical properties as the natural protein (with the exception of a higher mass). It is added from the beginning, before the protein fractionation step, when the latter is present. It is thus co-purified with the native protein, during the protein fractionation step. It has the same yield of treatment, in particular by digestion, as the native protein. The heavy peptide obtained after cleavage is also co-purified with the natural peptide, if a peptide fractionation step is carried out. The two peptides are thus injected simultaneously into the mass spectrometer, so as to be quantitatively assayed. They then undergo the same ionization yields in the source. The comparison of the areas of the peaks of the natural peptides and of the reference peptides in the PSAQ method makes it possible to calculate the concentration of the protein to be assayed while taking into account all of the steps of the assay method.

All of these techniques, namely AQUA, QconCAT or PSAQ or any other calibration technique, used in assays by mass spectrometry and in particular in MRM or MS assays, may be used to perform the calibration, in the context of the invention.

In the context of the invention, an external calibration straight line may be produced, with a range of known variable concentrations of the microorganism group to be quantified. The quantification of at least one microorganism group will be carried out by interpolation of the amount of the marker of at least one microorganism group to be quantified in a sample, on one or more external calibration straight lines of the protein or peptide marker(s) of said microorganism groups to be quantified. The external calibration range can for example be produced with pure culture samples of at least one microorganism group to be quantified.

The amount of bacteria contained in a calibration range is characterized by its expression in number of bacteria per liter in or g/l or by a multiple or a submultiple of these units, or by the usual derivatives of these units, including their multiples or their submultiples. Thus, those skilled in the art frequently express the amount of bacteria in a liquid sample in CFU/ml or by a multiple or a submultiple of this unit. CFU is the acronym for "Colony-Forming Units". This usual unit corresponds to the number of bacteria having formed a colony after culture on a Petri dish (on condition that the isolation of the colonies is sufficient for each colony to be clearly separated from the adjacent colonies).

Those skilled in the art also use the McFarland (McF) unit. This unit corresponds to the measurement of the turbidity of a bacterial suspension measured at 600 nm by nephelometry, calibrated by means of McFarland standards produced with a mixture of barium chloride and sulfuric acid produced in the following way (TABLE 1):

TABLE 1

| | Number of the McFarland standard | | | | |
|---|---|---|---|---|---|
| | 0.5 | 1 | 2 | 3 | 4 |
| Volume of barium chloride at 1.0% in water (ml) | 0.05 | 0.1 | 0.2 | 0.3 | 0.4 |
| Volume of sulfuric acid at 1.0% in water (ml) | 9.95 | 9.9 | 9.8 | 9.7 | 9.6 |
| Approximate cell density ($10^8$ CFU/ml) | 1.5 | 3.0 | 6.0 | 9.0 | 12.0 |
| Percentage transmittance at 600 nm | 74.3 | 55.6 | 35.6 | 26.4 | 21.5 |
| Absorbance at 600 nm | 0.08 to 0.1 | 0.257 | 0.451 | 0.582 | 0.669 |

The McFarland unit is thus proportional to an amount of bacteria, but it should be noted that this correspondence depends on the bacterial species, owing to a turbidity specific to each species. In order to quantitatively use a bacterial assay performed in McF, the amount observed in McF should thus be calibrated beforehand with solutions of which the amount of bacteria is characterized, for example, by an amount in CFU/ml.

In the context of the invention, the amount of bacteria can also be measured relatively and used to perform a relative quantification. In this case, it is not necessary to correlate a measurement characterizing the amount of bacteria with an amount of bacteria expressed in one of the characteristic units mentioned below. Advantageously, the method according to the invention makes it possible to measure, within the same analysis, signals corresponding to peptides, or proteins characteristic respectively of the amount of microorganisms and the amount of the peptide(s) of interest and/or of the protein(s) of interest. The ratio between the signal of the peptides or proteins of interest and of the peptides or proteins characteristic of the amount of microorganisms makes it possible to obtain a relative quantification of the level of expression of the peptides and/or proteins of interest, without having to use a calibration straight line as mentioned above.

The examples which follow are given only by way of illustration and do not in any way constituent a limitation of the invention.

EXAMPLES

Example 1: Quantification of Bacteria from Pure Cultures, by Identification of the Representative Peptides by MRM 1. Culturing of Bacteria on Agar Culture Media:
The optimal culture media and the optimal culture conditions are different depending on the microorganism species.

For the microorganisms used, the culture medium used is a Columbia agar with sheep blood (COS agar—bioMérieux reference 43041). An isolation is carried out on this culture medium and then the latter is incubated for 18 to 24 h at 37° C., in an aerobic or anaerobic atmosphere depending on the species.

2. Culturing of the Bacteria in Broth:
 a) One or more colonies isolated according to the protocol described in step 1 are selected.
 b) These colonies are suspended in a 9 ml TSB broth (bioMérieux reference 42100), then cultured at 37° C. for 15-18 hours.
 c) A fraction of the suspension obtained in step b) is taken using a sterile Pasteur pipette and placed in a tube containing 3.0 ml of aqueous sterile saline solution (containing 0.45-0.50% of NaCl, of pH 4.5 to 7.0). The concentration of bacteria in this new suspension is then adjusted to between 0.50 and 0.8 McFarland with a calibrated Densimat (sold by the applicant) (this density makes it possible to obtain an amount of between $1.5 \times 10^8$ and $2.4 \times 10^8$ CFU/ml in $E.\ coli$). This solution is denoted "H0".
 d) Starting from 1 ml of H0 solution, six 10-fold serial dilutions are then carried out in calibrated tubes containing 9 ml of Tryptone salt (sold by the applicant).
 e) 100 µl of each of the last two dilution tubes are then plated out on three COS agars in order to determine the bacterial concentration of the "H0" solution. The agars are placed in culture for 12-18 hours at 37° C.
 f) 1 ml of the $\frac{1}{100}^{th}$ dilution of the "H0" solution prepared in step d) is again diluted in 10 tubes containing 9 ml of TSB broth.
 g) Nine of the ten tubes of TSB broth are placed in an incubator-shaker at 37° C. 1 ml of the broth contained in the final tube, denoted "H1", is taken and placed in a 1.5 ml tube in order to be used to obtain digested proteins from the bacteria in suspension.
 h) At regular intervals during the day (approximately once an hour), each of the nine tubes of TSB broth is taken out of the incubator. It is denoted "Hx" (with x ranging from 2 to 10). Each of the tubes undergoes the same protocol as the "H1" tube, as described in step g).

3. Obtaining of Digested Proteins:

Conventionally, the following protocol is carried out in 15 steps:
 a) Sampling of 1 ml of "Hx" broth previously mentioned.
 b) Centrifugation for 10 minutes at 6000 G.
 c) Removal of the supernatant.
 d) Suspension of the pellet in 150 µl of 50 mM bicarbonate buffer, pH=8.
 e) Addition of 10 µl of a pool of heavy peptides (peptides corresponding to the proteotypic peptides, but in which one or more carbon 12 ($^{12}C$) atoms is (are) replaced with carbon 13 ($^{13}C$), and/or one or more nitrogen 14 ($^{14}N$) atoms is (are) replaced with nitrogen 15 ($^{15}N$)).
 f) Addition of dithiothreitol (DTT) so as to obtain a final concentration of 5 mM.
 g) Addition of 150 mg of glass beads 1 mm in diameter and 50 mg of zirconium/silica beads 0.1 mm in diameter (Biospec Products (Bartlesville, Okla., USA)).
 h) Lysis of the bacteria and reduction of the protein by placing the tubes in an ultrasound probe for 5 minutes (95° C.).
 i) Cooling of the tubes in ice for 1 minute.
 j) Addition of iodoacetamide so as to obtain a final concentration of 12.5 mM.
 k) Alkylation for 5 minutes at ambient temperature and in the dark.
 l) Addition of 200 µg of trypsin.
 m) Digestion at 50° C. for 15 minutes in a Thermomixer® at 850 rpm.
 n) Addition of 0.5% formic acid until a pH below 4 is obtained, so as to stop the reaction.
 o) Centrifugation for 20 minutes at 10 000 G.

4. Characterization of Samples of Bacteria

Each sample is treated according to the protocol of section 3, then a volume of 50 µl of digested proteins is injected and analyzed according to the following conditions:
 Nexera chromatographic system from Shimadzu (Kyoto, Japan)
 Waters BEH C18 column (Waters, Saint-Quentin en Yvelines, France) with an internal diameter of 2.1 mm, a length of 100 mm and a particle size of 3.5 µm.
 Solvent A: $H_2O$+0.1% formic acid.
 Solvent B: ACN+0.1% formic acid.
 HPLC gradient defined in TABLE 2 below:

TABLE 2

| Time | Flow (µl) | Solvent A (%) | Solvent B (%) |
|---|---|---|---|
| 0 | 300 | 98 | 2 |
| 3 | 300 | 98 | 2 |
| 25 | 300 | 67 | 33 |
| 25.1 | 300 | 0 | 100 |
| 35 | 300 | 0 | 100 |
| 35.1 | 300 | 98 | 2 |
| 45 | 300 | 98 | 2 |

The eluent leaving the chromatography column is directly injected into the ionization source of the QTRAP® 5500 mass spectrometer from AB Sciex (Framingham, Mass., United States of America).

The peptides, derived from the digestion of the proteins of the bacterium, are analyzed by mass spectrometry in MRM mode. The peptides followed and detected make it possible to identify a microorganism group by virtue of their nature specific for a microorganism group. For this, the fragment(s) indicated in TABLE 3 is (are) detected.

TABLE 3

| Species | Uniprot reference of the protein | Peptide sequence | Fragment ion | $m/z_1$ Q1 | $m/z_2$ Q3 |
|---|---|---|---|---|---|
| Psedomonas aeruginosa | A3LLD0 | ADAAANDTLK | y6 singly charged | 495.249 | 661.352 |
| | | | y7 singly charged | 495.249 | 732.389 |
| | | | Y8 singly charged | 495.249 | 803.426 |
| Escherichia coli | ADHE | DYVEGETAAK | y6 singly charged | 541.754 | 576.299 |
| | | | y7 singly charged | 541.754 | 705.341 |
| | | | Y8 singly charged | 541.754 | 804.41 |
| Staphylococcus aureus | GUAA | LGIELGIPEHLVWR | Y3 singly charged | 544.64 | 460.266 |
| | | | Y7 doubly charged | 544.64 | 468.756 |
| | | | y7 singly charged | 544.64 | 936.505 |
| Enterobacteriaceae | EFG | AGDIAAAIGLK | y6 singly charged | 500.295 | 572.377 |
| | | | y7 singly charged | 500.295 | 643.414 |
| | | | Y5 singly charged | 500.295 | 501.339 |

The ratio of the area under the peak representative of the peptide studied relative to the area under the peak of the corresponding synthetic heavy peptide is considered as the response observed, and will be correlated with the amount of bacteria measured.

The other machine parameters used are the following:
 Scan type: MRM
 Polarity: Positive
 Ionization source: Turbo VTM (AB Sciex)
 Q1 setting: filtering with unit resolution
 Q3 setting: filtering with unit resolution
 Inter-scan pause: 3.00 msec
 Scan speed: 10 Da/s
 Curtain gas: 50.00 psi
 Cone voltage: 5500.00 V
 Source temperature: 550.00° C.
 Nebulizing gas: 50.00 psi
 Heating gas: 50.00 psi
 Dynamic filling: activated
 Entry potential before Q0 (EP): 10.00 V
 Collision cell exit potential (CXP): 15 V
 Total cycle time: 1.2 sec 5. Identification of the Peptides Representative of the Amount of Bacteria:

a. Peptides of which the Expression does not Depend on the Culture Phase

Various strains of the species listed below, originating from the applicant's strain collection are treated and analyzed as previously described (sections 2, 3 and 4).

*Pseudomonas aeruginosa*: strain 1 and strains 4 to 6
*Escherichia coli*: strains 2 and 14
*Staphylococcus aureus*: strains 3 and 23.

The correlation coefficients between the measurement of the amount of bacteria and the amount of peptide measured by mass, over time, that is to say regardless of the growth phrase of the bacterium, are represented in TABLE 4 below.

TABLE 4

| Species | Protein | Peptide | $R^2$ |
|---|---|---|---|
| P. aeruginosa | A3LLD0 | ADAAANDTLK | 0.93 |
| E. coli | ADHE | DYVEGETAAK | 0.98 |
| Enterobacteriaceae | EFG | AGDIAAAIGLK | 0.98 |
| S. aureus | GUAA | LGIELGIPEHLVWR | 0.97 |

The results are presented in FIGS. 1 to 4. These figures illustrates the correlation between the amount of bacteria measured by quantitative culture (counting on a Petri dish after successive dilutions) and the amount of bacteria measured by mass spectrometry by measuring the area under the chromatography peak of a peptide specific for the bacterial species to be quantified. This correlation is illustrated in this example, as a function of the growth time of the bacterium.

For the peptides represented here, the amount measured depends only on the amount of bacteria present, and not on the growth phase of the bacterium.

b. Peptides of which the Expression does not Depend on the Strain Used

After culturing of a strain in accordance with what is described in section 1 above, a few colonies are suspended in 9 ml of TSB broth, and incubated for between 12 h and 15 h at 37° C.

The concentration of bacteria in the solution is determined by McFarland measurement with a calibrated Densimat.

The solutions are between 3 and 7 McFarland, this density making it possible to obtain an amount of between $9 \times 10^8$ and $2.1 \times 10^9$ CFU/ml in *E. coli*.

Seven successive 10-fold dilutions are carried out and 100 µl of each of the final two dilutions are plated out on three COS agars. The agars are placed in an incubator at 37° C. for 18 h for the purpose of allowing exact quantification of the number of CFU/ml present in the starting broth.

The protocol described above, used to obtain the digested proteins, is reproduced with 1 ml of the starting broth and also the first five dilution tubes.

Six range points of each of the strains used were monitored using the method of characterization specific for each bacterial group. In other words, each species is monitored by MRM by detection of the peptides specific for the species or for the family.

List of the Samples Analyzed:
*Pseudomonas aeruginosa*: strain 1 and strains 4 to 11.
*Escherichia coli*: strain 2 and strains 12 to 20.
*Staphylococcus aureus*: strain 3 and strains 21 to 24.
Unknown samples: liquid 1 to liquid 15.

Peptide correlation curves are produced for the various strains of one and the same species, so as to determine the peptides which retain the same behavior regardless of the strain used. These curves are obtained with the peptides presented in TABLE 2 above.

FIGS. 5, 6 and 7 illustrate, for each of the species, the correlation between the concentration of bacteria present in the sample and the amount of peptide measured by MRM mass spectrometry. This correlation is measured between at least five different strains per species. The correlation coefficients and the equations of the corresponding calibration straight lines appear in TABLE 5 below. In the equation, x is the amount of peptides measured by MRM by calculating the ratio of the area under the chromatographic peak of the natural peptide divided by the area under the chromatographic peak of the heavy peptide; Y is the amount of bacteria calculated in CFU/ml; ln(x) represents the Napierian logarithm of x.

TABLE 5

| Species | Protein | Peptide | $R^2$ | Equation |
|---|---|---|---|---|
| P. aeruginosa | A3LLD0 | ADAAANDTLK | 0.96 | $Y = e^{(1.04 ln(x) + 21.1)}$ |
| E. coli | ADHE | DYVEGETAAK | 0.97 | $Y = e^{(0.88 ln(x) + 17.1)}$ |
| S. aureus | GUAA | LGIELGIPEHLVWR | 0.96 | $Y = e^{(1.08 ln(x) + 21.5)}$ |

The two examples above make it possible to validate the use of these peptides for the quantification of bacteria by MRM mass spectrometry, by performing a quantification by external calibration with a pure strain range.

These examples also make it possible to validate that the peptides chosen are representative of the amount of bacteria present in a sample.

The equation calculated for the external calibration straight line thus makes it possible to calculate, in CFU/ml, the amount of bacteria present in an unknown sample. The amounts of bacteria are reproduced in TABLE 6 below.

TABLE 6

| Sample | Concentration of P. aeruginosa (CFU/ml) | Concentration of E. coli (CFU/ml) | Concentration of S. aureus (CFU/ml) |
|---|---|---|---|
| Liquid 1 | $7.18 \, 10^7$ | 0 | 0 |
| Liquid 2 | $1.64 \, 10^7$ | 0 | 0 |
| Liquid 3 | 0 | 0 | $2.7 \, 10^7$ |
| Liquid 4 | 0 | 0 | $4.0 \, 10^8$ |
| Liquid 5 | $1.00 \, 10^9$ | 0 | 0 |
| Liquid 6 | 0 | 0 | $1.0 \, 10^9$ |
| Liquid 7 | 0 | 0 | $5.0 \, 10^8$ |
| Liquid 8 | 0 | 0 | $3.5 \, 10^8$ |
| Liquid 9 | $1.39 \, 10^8$ | 0 | 0 |
| Liquid 10 | 0 | 0 | $3.0 \, 10^8$ |
| Liquid 11 | $1.23 \, 10^8$ | 0 | 0 |
| Liquid 12 | 0 | 0 | $4.2 \, 10^8$ |
| Liquid 13 | 0 | 0 | $3.0 \, 10^7$ |
| Liquid 14 | 0 | 0 | $5.0 \, 10^8$ |
| Liquid 15 | 0 | 0 | 0 |

Particularly advantageously, the method thus developed makes it possible to quantify at least three bacterial species in an unknown sample.

Example 2: Measurement of the Level of Expression of the VanA Enzyme

1. Culturing of the Sample on Culture Medium in the Absence of Antibiotic:

The optimal culture media and the optimal culture conditions are different depending on the microorganism species. By default, the sample is inoculated onto various media:

Columbia agar with sheep blood (bioMérieux reference 43041) for 18 to 24 h at 35° C., in an aerobic or anaerobic atmosphere;
TSA agar (bioMérieux reference 43011) for 18 to 24 h at 37° C.

2. Obtaining of Digested Proteins from Microorganisms

The following protocol is carried out in 17 steps:

a) Sampling of a microorganism colony, obtained according to example 2 or 3, or of a sample enriched according to example 1, and suspension in 10 to 100 μl of a solution of 6M guanidine hydrochloride, 50 mM Tris-HCl, pH=8.0.
b) Addition of dithiothreitol (DTT) so as to obtain a final concentration of 5 mM.
c) Reduction for 20 minutes at 95° C. in a water bath.
d) Cooling of the tubes to ambient temperature.
e) Addition of iodoacetamide so as to obtain a final concentration of 12.5 mM.
f) Alkylation for 40 minutes at ambient temperature and in the dark.
g) Dilution by a factor of 6 with a 50 mM $NH_4HCO_3$ solution, pH=8.0, so as to obtain a final concentration of guanidine hydrochloride of 1M.
h) Addition of 1 μg of trypsin.
i) Digestion at 37° C. for 6 hours up to overnight.
j) Addition of 0.5% formic acid to a pH of below 4 so as to stop the reaction.
k) The volume of sample is made up to 1 ml with water/0.5% (v/v) formic acid.
l) Equilibration of the Waters Oasis HLB columns with 1 ml of methanol and then 1 ml of $H_2O$/0.1% (v/v) formic acid.
m) Deposition of the sample which flows by gravity.
n) Washing with 1 ml of $H_2O$/0.1% (v/v) formic acid.
o) Elution with 1 ml of a mixture of 80% of methanol and 20% of water/0.1% (v/v) formic acid.
p) The eluate is evaporated off with a SpeedVac® SPD2010 evaporator (Thermo Electron Corporation, Waltham, Mass., United States of America), for 2 hours, in order to obtain a volume of approximately 100 μl.
q) The eluate is then taken up in a solution of water/0.5% (v/v) formic acid, the amount being sufficient (QS) for 200 μl.

3. Quantification of the Level of Expression of the VanA Enzyme

The VanA enzyme confers resistance to vancomycin in enterococci. The level of expression of this enzyme can be induced by the presence of vancomycin. Without induction, the expression level is also very variable depending on the bacterial strains. In order to measure the level of expression of VanA, it is necessary to measure the amount of VanA and the amount of bacteria present in the sample. The ratio between these two amounts will make it possible to measure the level of expression of the VanA protein. The amount of VanA present in the samples is measured using peptides described in patent application WO-A-2014/020276. The amount of bacteria present in the samples is measured using peptides derived from the 3 proteins RL29, RS19 and RL22.

The VanA enzyme is quantified in 3 samples of *Enterococcus faecalis* (Ech1 to Ech3), obtained from pure cultures, according to the following method:

The microorganism colony is obtained in accordance with section a), treated according to section b), and then a volume of 50 μl of digested proteins is injected and analyzed according to the following conditions:

Dionex Ultimate 3000 chromatographic system from Dionex Corporation (Sunnyvale, United States of America).
Waters BEH130 C18 column, with an internal diameter of 2.1 mm, a length of 100 mm and a particle size of 3.5 μm (Waters, Saint-Quentin en Yvelines, France).
Solvent A: $H_2O$+0.1% formic acid.
Solvent B: ACN+0.1% formic acid.
HPLC gradient defined in TABLE 7 below.

TABLE 7

| Time (min) | Flow (μl) | Solvent A (%) | Solvent B (%) |
|---|---|---|---|
| 0 | 300 | 98 | 2 |
| 3 | 300 | 98 | 2 |
| 28 | 300 | 63 | 37 |
| 30 | 300 | 0 | 100 |
| 38 | 300 | 0 | 100 |
| 38.1 | 300 | 98 | 2 |
| 45 | 300 | 98 | 2 |

The eluate leaving the chromatographic column is directly injected into the ionization source of the QTRAP® 5500 mass spectrometer from AB Sciex (Framingham, Mass., United States of America).

The peptides, derived from the digestion of the proteins of the microorganism, are analyzed by mass spectrometry in MRM mode. Only the peptides indicated in TABLE 8 are detected. For this, the fragment(s) indicated in TABLE 8 is (are) detected.

TABLE 8

| Transition number | Protein | Peptide | Charge state of the precursor | First-generation fragment ion |
|---|---|---|---|---|
| 1 | VanA | IHQEVEPEK | 2 | y5 singly charged |
| 2 | VanA | IHQEVEPEK | 2 | y6 singly charged |
| 3 | VanA | IHQEVEPEK | 2 | y7 singly charged |
| 4 | VanA | LIVLALK | 2 | y4 singly charged |
| 5 | VanA | LIVLALK | 2 | y5 singly charged |
| 6 | VanA | LIVLALK | 2 | y6 singly charged |
| 7 | VanA | LQYGIFR | 2 | y4 singly charged |
| 8 | VanA | LQYGIFR | 2 | y5 singly charged |
| 9 | VanA | LQYGIFR | 2 | y6 singly charged |
| 10 | VanA | MHGLLVK | 2 | b5 singly charged |
| 11 | VanA | MHGLLVK | 2 | y5 singly charged |
| 12 | VanA | MHGLLVK | 2 | y6 singly charged |
| 13 | VanA | MMAAAGIALPELIDR | 2 | y6 singly charged |
| 14 | VanA | MMAAAGIALPELIDR | 2 | y7 singly charged |
| 15 | VanA | MMAAAGIALPELIDR | 2 | y8 singly charged |
| 16 | VanA | NAGIATPAFWVINK | 2 | y10 singly charged |

TABLE 8 -continued

| Transition number | Protein | Peptide | Charge state of the precursor | First-generation fragment ion |
|---|---|---|---|---|
| 17 | VanA | NAGIATPAFWVINK | 2 | y8 singly charged |
| 18 | VanA | NAGIATPAFWVINK | 2 | y9 singly charged |
| 19 | VanA | SAIEIAANINK | 2 | y6 singly charged |
| 20 | VanA | SAIEIAANINK | 2 | y7 singly charged |
| 21 | VanA | SAIEIAANINK | 2 | y8 singly charged |
| 22 | VanA | SGSSFGVK | 2 | y5 singly charged |
| 23 | VanA | SGSSFGVK | 2 | y6 singly charged |
| 24 | VanA | SGSSFGVK | 2 | y7 singly charged |
| 25 | VanA | SLTYIVAK | 2 | y4 singly charged |
| 26 | VanA | SLTYIVAK | 2 | y5 singly charged |
| 27 | VanA | SLTYIVAK | 2 | y6 singly charged |
| 28 | VanA | VDMFLQDNGR | 2 | y6 singly charged |
| 29 | VanA | VDMFLQDNGR | 2 | y7 singly charged |
| 30 | VanA | VDMFLQDNGR | 2 | y8 singly charged |
| 31 | VanA | VNSADELDYAIESAR | 2 | y6 singly charged |
| 32 | VanA | VNSADELDYAIESAR | 2 | y7 singly charged |
| 33 | VanA | VNSADELDYAIESAR | 2 | y8 singly charged |
| 34 | VanA | YEPLYIGITK | 2 | y7 singly charged |
| 35 | VanA | YEPLYIGITK | 2 | y8 singly charged |
| 36 | VanA | YEPLYIGITK | 2 | y8 doubly charged |
| 37 | RL22 | LVIDLIR | 2 | y4 singly charged |
| 38 | RL22 | LVIDLIR | 2 | y5 singly charged |
| 39 | RL22 | LVIDLIR | 2 | y6 singly charged |
| 40 | RL29 | FQLATGQLENTAR | 2 | y10 singly charged |
| 41 | RL29 | FQLATGQLENTAR | 2 | y8 singly charged |
| 42 | RL29 | FQLATGQLENTAR | 2 | y9 singly charged |
| 43 | RS19 | LGEFAPTR | 2 | y5 singly charged |
| 44 | RS19 | LGEFAPTR | 2 | y6 singly charged |
| 45 | RS19 | LGEFAPTR | 2 | y7 singly charged |

The transitions mentioned in TABLE 8 are detected using the parameters appearing in TABLES 9 and 10, below.

TABLE 9

| Transition number | Retention time | (m/z) filtered in Q1 | (m/z) filtered in Q3 | Collision energy (eV) |
|---|---|---|---|---|
| 1 | 8.75 | 554.79 | 601.32 | 29 |
| 2 | 8.75 | 554.79 | 730.36 | 29 |
| 3 | 8.75 | 554.79 | 858.42 | 29 |
| 4 | 19.71 | 385.28 | 444.32 | 22 |
| 5 | 19.71 | 385.28 | 543.39 | 22 |
| 6 | 19.71 | 385.28 | 656.47 | 22 |
| 7 | 17.91 | 448.75 | 492.29 | 25 |
| 8 | 17.91 | 448.75 | 655.36 | 25 |
| 9 | 17.91 | 448.75 | 783.41 | 25 |
| 10 | 13.32 | 399.24 | 552.3 | 23 |
| 11 | 13.32 | 399.24 | 529.37 | 23 |
| 12 | 13.32 | 399.24 | 666.43 | 23 |
| 13 | 23.29 | 786.42 | 742.41 | 32 |
| 14 | 23.29 | 786.42 | 855.49 | 31 |
| 15 | 23.29 | 786.42 | 926.53 | 34 |
| 16 | 22.44 | 751.41 | 1146.63 | 38 |
| 17 | 22.44 | 751.41 | 974.55 | 38 |
| 18 | 22.44 | 751.41 | 1075.59 | 38 |
| 19 | 15.89 | 572.32 | 630.36 | 25 |
| 20 | 15.89 | 572.32 | 743.44 | 26 |
| 21 | 15.89 | 572.32 | 872.48 | 25 |
| 22 | 10.67 | 384.7 | 537.3 | 20.5 |
| 23 | 10.67 | 384.7 | 624.34 | 18.5 |
| 24 | 10.67 | 384.7 | 681.36 | 19.5 |
| 25 | 15.29 | 447.77 | 430.3 | 25 |
| 26 | 15.29 | 447.77 | 593.37 | 25 |
| 27 | 15.29 | 447.77 | 694.41 | 25 |
| 28 | 16.64 | 597.78 | 702.35 | 29 |
| 29 | 16.64 | 597.78 | 849.42 | 29 |
| 30 | 16.64 | 597.78 | 980.46 | 27 |
| 31 | 18.52 | 826.89 | 646.35 | 41 |
| 32 | 18.52 | 826.89 | 809.42 | 41 |
| 33 | 18.52 | 826.89 | 924.44 | 41 |
| 34 | 19.2 | 598.83 | 807.5 | 31 |
| 35 | 19.2 | 598.83 | 904.55 | 22 |
| 36 | 19.2 | 598.83 | 452.78 | 25 |
| 37 | 20.55 | 421.28 | 516.31 | 24 |
| 38 | 20.55 | 421.28 | 629.4 | 24 |
| 39 | 20.55 | 421.28 | 728.47 | 24 |
| 40 | 16.75 | 724.88 | 1060.54 | 37 |
| 41 | 16.75 | 724.88 | 888.45 | 37 |
| 42 | 16.75 | 724.88 | 989.5 | 37 |
| 43 | 13.45 | 445.74 | 591.32 | 25 |
| 44 | 13.45 | 445.74 | 720.37 | 25 |
| 45 | 13.45 | 445.74 | 777.39 | 25 |

TABLE 10

| Transition number | Orifice potential | Entry potential before Q0 | Collision cell exit potential | Positivity threshold |
|---|---|---|---|---|
| 1 | 80 | 10 | 35 | 2000 |
| 2 | 80 | 10 | 35 | 2000 |
| 3 | 80 | 10 | 35 | 2000 |
| 4 | 80 | 10 | 35 | 1400 |
| 5 | 80 | 10 | 35 | 2000 |
| 6 | 80 | 10 | 35 | 2000 |
| 7 | 80 | 10 | 35 | 2000 |
| 8 | 80 | 10 | 35 | 2000 |
| 9 | 80 | 10 | 35 | 1500 |
| 10 | 80 | 10 | 35 | 4000 |
| 11 | 80 | 10 | 35 | 4000 |
| 12 | 80 | 10 | 35 | 4000 |
| 13 | 120 | 10 | 18 | 2000 |
| 14 | 120 | 10 | 18 | 2000 |
| 15 | 120 | 10 | 18 | 2000 |
| 16 | 80 | 10 | 35 | 2000 |
| 17 | 80 | 10 | 35 | 2000 |
| 18 | 80 | 10 | 35 | 2000 |
| 19 | 90 | 10 | 15 | 2000 |
| 20 | 90 | 10 | 15 | 2000 |
| 21 | 90 | 10 | 15 | 2000 |

TABLE 10-continued

| Transition number | Orifice potential | Entry potential before Q0 | Collision cell exit potential | Positivity threshold |
|---|---|---|---|---|
| 22 | 85 | 10 | 24 | 2000 |
| 23 | 85 | 10 | 24 | 2000 |
| 24 | 85 | 10 | 24 | 2000 |
| 25 | 80 | 10 | 35 | 2000 |
| 26 | 80 | 10 | 35 | 1500 |
| 27 | 80 | 10 | 35 | 2000 |
| 28 | 100 | 10 | 17 | 2000 |
| 29 | 100 | 10 | 17 | 2000 |
| 30 | 100 | 10 | 17 | 2000 |
| 31 | 80 | 10 | 35 | 1000 |
| 32 | 80 | 10 | 35 | 2000 |
| 33 | 80 | 10 | 35 | 2000 |
| 34 | 105 | 10 | 20 | 1400 |
| 35 | 105 | 10 | 20 | 2000 |
| 36 | 105 | 10 | 20 | 2000 |
| 37 | 100 | 4 | 35 | 2000 |
| 38 | 100 | 4 | 35 | 2000 |
| 39 | 100 | 4 | 35 | 2000 |
| 40 | 100 | 4 | 35 | 2000 |
| 41 | 100 | 4 | 35 | 2000 |
| 42 | 100 | 4 | 35 | 2000 |
| 43 | 100 | 4 | 35 | 2000 |
| 44 | 100 | 4 | 35 | 2000 |
| 45 | 100 | 4 | 35 | 2000 |

The other machine parameters used are the following:
Scan type: MRM
Scheduled MRM: yes
Polarity: Positive
Ionization source: Turbo VTM (AB Sciex)
Q1 setting: filtering with unit resolution
Q3 setting: filtering with unit resolution
Inter-scan pause: 5.00 msec
Scan speed: 10 Da/s
Curtain gas: 50.00 psi
Cone voltage: 5500.00 V
Source temperature: 550.00° C.
Nebulizing gas: 50.00 psi
Heating gas: 40.00 psi
Collision-induced dissociation gas: 9.00 psi
Dynamic filling: inactivated
Total cycle time: 1.2 sec
Detection window: 90 sec The areas obtained for each of the transitions and for each of the microorganisms studied were measured. When the area of a transition is greater than or equal to the positivity threshold described in TABLE 10, the detection of the transition is considered to be positive and its signal in arbitrary units is reported in TABLE 11. When the area of a transition is less than the positivity threshold described in TABLE 10, the detection of the transition is considered to be negative and is denoted "0" in TABLE 11.

TABLE 11

| Transition number | Ech1 | Ech2 | Ech3 | Ech4 | Ech5 | Ech6 | Ech7 | Ech8 | Ech9 | Ech10 | Ech11 |
|---|---|---|---|---|---|---|---|---|---|---|---|
| 1 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 |
| 4 | 0 | 0 | 0 | 0 | 0 | 0 | 0 | 0 | 0 | 1463 | 0 |
| 5 | 0 | 0 | 0 | 0 | 0 | 0 | 0 | 0 | 0 | 13020 | 0 |
| 6 | 2915 | 0 | 5471 | 0 | 0 | 0 | 0 | 0 | 0 | 2647 | 0 |
| 7 | 0 | 0 | 0 | 0 | 0 | 0 | 0 | 0 | 0 | 2836 | 0 |
| 8 | 0 | 11040 | 0 | 0 | 0 | 0 | 0 | 0 | 0 | 10590 | 0 |
| 9 | 0 | 6243 | 0 | 0 | 0 | 0 | 0 | 0 | 0 | 1869 | 0 |
| 10 | 0 | 0 | 0 | 0 | 0 | 0 | 0 | 0 | 0 | 8169 | 0 |
| 11 | 0 | 0 | 8101 | 4026 | 0 | 4572 | 4169 | 0 | 0 | 25590 | 0 |
| 12 | 0 | 0 | 0 | 0 | 0 | 0 | 0 | 0 | 0 | 8767 | 0 |
| 13 | 0 | 2090 | 0 | 0 | 0 | 0 | 0 | 0 | 0 | 0 | 0 |
| 14 | 0 | 0 | 0 | 0 | 0 | 0 | 0 | 0 | 0 | 0 | 0 |
| 15 | 0 | 0 | 0 | 0 | 0 | 0 | 0 | 0 | 0 | 0 | 0 |
| 16 | 0 | 0 | 0 | 0 | 0 | 0 | 0 | 0 | 0 | 0 | 0 |
| 17 | 0 | 0 | 0 | 0 | 0 | 0 | 0 | 0 | 0 | 0 | 0 |
| 18 | 0 | 0 | 0 | 0 | 0 | 0 | 0 | 0 | 0 | 0 | 0 |
| 19 | 0 | 0 | 9028 | 0 | 0 | 0 | 0 | 0 | 0 | 389800 | 5610 |
| 20 | 0 | 0 | 6689 | 0 | 0 | 0 | 0 | 0 | 0 | 274700 | 4391 |
| 21 | 0 | 11610 | 7003 | 0 | 0 | 0 | 0 | 0 | 0 | 245300 | 4541 |
| 22 | 3069 | 0 | 18170 | 0 | 0 | 0 | 11340 | 0 | 0 | 53270 | 9942 |
| 23 | 0 | 0 | 7476 | 0 | 0 | 0 | 0 | 0 | 0 | 153400 | 5372 |
| 24 | 0 | 0 | 3490 | 0 | 0 | 0 | 0 | 0 | 0 | 68260 | 2667 |
| 25 | 2782 | 2536 | 4446 | 3109 | 3545 | 0 | 4009 | 2208 | 3027 | 3292 | 4181 |
| 26 | 0 | 2421 | 0 | 0 | 0 | 0 | 0 | 0 | 0 | 1625 | 0 |
| 27 | 0 | 0 | 2153 | 0 | 0 | 0 | 0 | 0 | 0 | 5453 | 0 |
| 28 | 0 | 0 | 0 | 0 | 0 | 0 | 0 | 0 | 0 | 2409 | 0 |
| 29 | 0 | 0 | 0 | 0 | 0 | 0 | 0 | 0 | 0 | 0 | 0 |
| 30 | 0 | 0 | 0 | 0 | 0 | 0 | 0 | 0 | 0 | 0 | 0 |
| 31 | 0 | 0 | 0 | 0 | 0 | 0 | 0 | 0 | 0 | 1028 | 0 |
| 32 | 0 | 2210 | 0 | 0 | 0 | 0 | 0 | 0 | 0 | 2794 | 0 |
| 33 | 0 | 0 | 0 | 0 | 0 | 0 | 0 | 0 | 0 | 2540 | 0 |
| 34 | 0 | 0 | 2089 | 0 | 0 | 2317 | 0 | 0 | 0 | 33950 | 1416 |
| 35 | 0 | 0 | 7596 | 0 | 0 | 0 | 0 | 0 | 0 | 179600 | 5836 |
| 36 | 2158 | 0 | 13690 | 0 | 0 | 0 | 0 | 0 | 0 | 290000 | 9278 |
| 37 | 1623000 | 4407000 | 3504000 | 694600 | 1063000 | 3283000 | 1951000 | 774400 | 294600 | 935300 | 949800 |
| 38 | 5766000 | 14880000 | 12010000 | 2500000 | 3820000 | 10980000 | 6640000 | 2710000 | 1067000 | 3290000 | 3417000 |
| 39 | 690300 | 1884000 | 1437000 | 306600 | 462500 | 1389000 | 813000 | 317900 | 124500 | 393800 | 398200 |
| 40 | 525500 | 624600 | 588800 | 236800 | 297600 | 430300 | 326400 | 117700 | 139800 | 210800 | 170400 |
| 41 | 1005000 | 1169000 | 1122000 | 448000 | 569300 | 810600 | 626100 | 225900 | 260300 | 417500 | 321500 |
| 42 | 749600 | 926300 | 861500 | 336700 | 436500 | 635000 | 481100 | 175700 | 206800 | 316100 | 256300 |

TABLE 11-continued

| Transition number | Ech1 | Ech2 | Ech3 | Ech4 | Ech5 | Ech6 | Ech7 | Ech8 | Ech9 | Ech10 | Ech11 |
|---|---|---|---|---|---|---|---|---|---|---|---|
| 43 | 3261000 | 3658000 | 3390000 | 1286000 | 1685000 | 3011000 | 2298000 | 954400 | 607700 | 1409000 | 1154000 |
| 44 | 1239000 | 1442000 | 1346000 | 497800 | 680500 | 1194000 | 900600 | 346300 | 232900 | 535000 | 462900 |
| 45 | 3836000 | 4295000 | 4080000 | 1542000 | 2065000 | 3715000 | 2668000 | 1079000 | 727500 | 1616000 | 1400000 |

When the three transitions of one and the same peptide are denoted greater than "0", the detection of the peptide is considered to be positive. The areas of all of the transitions of the VanA positive peptides are added together so as to measure the amount of VanA protein. Likewise, all of the areas of the peptides of the RL22, RL29 and RS19 proteins are added together so as to measure the amount of bacteria. The ratio of the sum of the areas of the VanA peptides to the sum of the areas of the peptides of the RL22, RL29 and RS19 proteins makes it possible to measure the relative expression level of the VanA protein in the bacterial strain of the sample tested. This relative expression level can also be expressed as percentage of the expression level of the sample having the highest relative expression level of VanA, in this case the Ech10 sample.

TABLE 12

| Sample | Amount of VanA (arbitrary units) | Amount of bacteria (arbitrary units) | Relative expression level of VanA | VanA expression level expressed as percentage of the expression level of the Ech10 sample |
|---|---|---|---|---|
| Ech1 | 0 | 18695400 | 0 | 0 |
| Ech2 | 0 | 33285900 | 0 | 0 |
| Ech3 | 75231 | 28339300 | 0.002654653 | 1.43 |
| Ech4 | 0 | 7848500 | 0 | 0 |
| Ech5 | 0 | 11079400 | 0 | 0 |
| Ech6 | 0 | 25447900 | 0 | 0 |
| Ech7 | 0 | 16704200 | 0 | 0 |
| Ech8 | 0 | 6701300 | 0 | 0 |
| Ech9 | 0 | 3661100 | 0 | 0 |
| Ech10 | 1688280 | 9123500 | 0.185047405 | 100 |
| Ech11 | 49053 | 8530100 | 0.005750577 | 3.11 |

Particularly advantageously, the amounts of VanA and of bacteria were measured simultaneously using the same MRM method and its was thus possible to measure, in a single analysis, the relative expression level of VanA. It is thus possible to very easily note that the Ech10 sample has a very high VanA expression level compared with the other samples, that the Ech3 and Ech11 samples have a low expression level and that all the other samples have a zero expression level.

Example 3: Measurement of the Porin Expression Level in *Klebsiella pneumoniae*

1. Culturing of the Sample

The optimal culture media and the optimal culture conditions are different depending on the microorganism species. By default, the sample is inoculated onto Colombia agar with sheep blood (bioMérieux reference 43041) for 18 to 24 h at 35° C., in an aerobic atmosphere.

2. Obtaining of Digested Proteins from Microorganisms

The following protocol is carried out in 17 steps:
a) Sampling of a microorganism colony, obtained according to example 2 or 3, or of a sample enriched according to example 1, and suspension in 10 to 100 µl of a solution 6M guanidine hydrochloride, 50 mM Tris-HCl, pH=8.0.
b) Addition of dithiothreitol (DTT) so as to obtain a final concentration of 5 mM.
c) Reduction for 20 minutes at 95° C. in a water bath.
d) Cooling of the tubes to ambient temperature.
e) Addition of iodoacetamide so as to obtain a final concentration of 12.5 mM.
f) Alkylation for 40 minutes at ambient temperature and in the dark.
g) Dilution by a factor of 6 with a 50 mM $NH_4HCO_3$ solution, pH=8.0, so as to obtain a final concentration of guanidine hydrochloride of 1M.
h) Addition of 1 µg of trypsin.
i) Digestion at 37° C. for 6 hours up to overnight.
j) Addition of 0.5% formic acid to a pH of below 4 so as to stop the reaction.
k) The sample volume is made up to 1 ml with water/0.5% (v/v) formic acid.
l) Equilibration of the Waters Oasis HLB columns with 1 ml of methanol and then 1 ml of $H_2O$/0.1% (v/v) formic acid.
m) Deposition of the sample which flows by gravity.
n) Washing with 1 ml of $H_2O$/0.1% (v/v) formic acid.
o) Elution with 1 ml of a mixture of 80% of methanol and 20% of water/0.1% (v/v) formic acid.
p) The eluate is evaporated off with a SpeedVac® SPD2010 evaporator (Thermo Electron Corporation, Waltham, Mass., United States of America), for 2 hours, in order to obtain a volume of approximately 100 µl.
q) The eluate is then taken up in a solution of water/0.5% (v/v) formic acid, this being in an amount sufficient (QS) for 200 µl.

4. Quantification of the Porin Expression Level

Porins are bacterial wall proteins which allow the diffusion of molecules through this membrane. They may or may not be involved in resistance. Thus, for those which are involved, the decrease in their amount implies a decrease in the sensitivity of the bacterium, often to several antibiotics. It is thus important to quantify the porins associated with resistance in the strains.

In this example, the porins sought are the following: LamB, OmpA, OmpF. The role of OmpF in the development of antibiotic resistance is established. The other porins are not, a priori, involved in resistance [37].

The porins are quantified in the 14 strains numbered from Ech1 to Ech14

The microorganism colony is obtained in accordance with section a), treated according to section b), and then a volume of 50 µl of digested proteins is injected and analyzed according to the following conditions:

Nexera chromatographic system from Shimadzu (Kyoto, Japan)

Waters BEH C18 column (Waters, Saint-Quentin en Yvelines, France), with an internal diameter of 2.1 mm, a length of 100 mm and a particle size of 3.5 µm.

Solvent A: $H_2O$+0.1% formic acid.
Solvent B: ACN+0.1% formic acid.
The HPLC gradient is defined in TABLE 13 below.

TABLE 13

| Time (min) | Flow (µl) | Solvent A (%) | Solvent B (%) |
|---|---|---|---|
| 0 | 300 | 95 | 5 |
| 3 | 300 | 95 | 5 |
| 26 | 300 | 65 | 35 |
| 26.1 | 300 | 5 | 95 |
| 28 | 300 | 5 | 95 |

The eluate leaving the chromatography column is directly injected into the ionization source of the QTRAP® 5500 mass spectrometer from AB Sciex (Framingham, Mass., United States of America).

The transitions used for the quantification of the bacteria are described in TABLE 14.

TABLE 14

| Transition number | (m/z) filtered in Q1 | (m/z) filtered in Q3 | Protein | Peptide sequence | Precursor charge state | Fragment ion |
|---|---|---|---|---|---|---|
| 1 | 547.95 | 766.432 | SEQ ID No. 15 | AFAASGELEVNHLQR | 3 | y6 singly charged |
| 2 | 547.95 | 667.363 | SEQ ID No. 15 | AFAASGELEVNHLQR | 3 | y5 singly charged |
| 3 | 547.95 | 712.368 | SEQ ID No. 15 | AFAASGELEVNHLQR | 3 | y13 doubly charged |
| 4 | 642.874 | 1058.573 | SEQ ID No. 17 | LLVSELTGVEPK | 2 | y10 singly charged |
| 5 | 642.874 | 959.504 | SEQ ID No. 17 | LLVSELTGVEPK | 2 | y9 singly charged |
| 6 | 642.874 | 743.43 | SEQ ID No. 17 | LLVSELTGVEPK | 2 | y7 singly charged |
| 7 | 551.791 | 902.458 | SEQ ID No. 19 | SLQAQVAEEK | 2 | y8 singly charged |
| 8 | 551.791 | 774.399 | SEQ ID No. 19 | SLQAQVEAEK | 2 | y7 singly charged |
| 9 | 551.791 | 703.362 | SEQ ID No. 19 | SLQAQVAEEK | 2 | y6 singly charged |

The transitions used to quantify the porin expression are described in TABLE 15. The sequences of LamB, OmpA and OmpF (OmpK35) correspond respectively to SEQ ID No. 21, SEQ ID No. 27 and SEQ ID No. 32.

TABLE 15

| Transition number | (m/z) filtered in Q1 | (m/z) filtered in Q3 | Protein | Peptide sequence | Precursor charge state | First-generation fragment |
|---|---|---|---|---|---|---|
| 10 | 579.755 | 450.231 | LamB | DSSGSGAFTSSR | 2 | y4 |
| 11 | 579.755 | 725.358 | LamB | DSSGSGAFTSSR | 2 | Y7 |
| 12 | 579.755 | 812.39 | LamB | DSSGSGAFTSSR | 2 | Y8 |
| 13 | 579.755 | 869.411 | LamB | DSSGSGAFTSSR | 2 | Y9 |
| 14 | 407.229 | 218.15 | LamB | IFATYAK | 2 | y2 |
| 15 | 407.229 | 381.213 | LamB | IFATYAK | 2 | Y3 |
| 16 | 407.229 | 482.261 | LamB | IFATYAK | 2 | y4 |
| 17 | 407.229 | 553.298 | LamB | IFATYAK | 2 | y5 |
| 18 | 677.357 | 395.204 | LamB | LAGLETNPGGVLELGVDYGR | 3 | y3 |
| 19 | 677.357 | 666.321 | LamB | LAGLETNPGGVLELGVDYGR | 3 | y6 |
| 20 | 677.357 | 779.405 | LamB | LAGLETNPGGVLELGVDYGR | 3 | y7 |
| 21 | 677.357 | 908.447 | LamB | LAGLETNPGGVLELGVDYGR | 3 | y8 |
| 22 | 437.245 | 333.192 | LamB | LGQELWK | 2 | y2 |
| 23 | 437.245 | 575.319 | LamB | LGQELWK | 2 | y4 |
| 24 | 437.245 | 703.377 | LamB | LGQELWK | 2 | Y5 |

TABLE 15 -continued

| Transition number | (m/z) filtered in Q1 | (m/z) filtered in Q3 | Protein | Peptide sequence | Precursor charge state | First-generation fragment |
|---|---|---|---|---|---|---|
| 25 | 437.245 | 760.399 | LamB | LGQELWK | 2 | y6 |
| 26 | 841.345 | 565.246 | LamB | NSESGGSYTFSSDDTK | 2 | y5 |
| 27 | 841.345 | 652.278 | LamB | NSESGGSYTFSSDDTK | 2 | y6 |
| 28 | 841.345 | 1063.458 | LamB | NSESGGSYTFSSDDTK | 2 | y9 |
| 29 | 596.832 | 708.393 | OmpA | AQSVVDYLVAK | 2 | y6 |
| 30 | 596.832 | 807.461 | OmpA | AQSVVDYLVAK | 2 | y7 |
| 31 | 596.832 | 906.529 | OmpA | AQSVVDYLVAK | 2 | y8 |
| 32 | 596.832 | 993.562 | OmpA | AQSVVDYLVAK | 2 | y9 |
| 33 | 626.812 | 611.278 | OmpA | DGSAVVLGYTDR | 2 | y5 |
| 34 | 626.812 | 724.362 | OmpA | DGSAVVLGYTDR | 2 | y6 |
| 35 | 626.812 | 823.431 | OmpA | DGSAVVLGYTDR | 2 | y7 |
| 36 | 626.812 | 922.499 | OmpA | DGSAVVLGYTDR | 2 | y8 |
| 37 | 409.721 | 361.198 | OmpA | LGGMVWR | 2 | y2 |
| 38 | 409.721 | 460.267 | OmpA | LGGMVWR | 2 | y3 |
| 39 | 409.721 | 648.329 | OmpA | LGGMVWR | 2 | y5 |
| 40 | 542.277 | 522.267 | OmpA | SDVLFNFNK | 2 | y4 |
| 41 | 542.277 | 669.336 | OmpA | SDVLFNFNK | 2 | y5 |
| 42 | 542.277 | 782.42 | OmpA | SDVLFNFNK | 2 | y6 |
| 43 | 542.277 | 881.488 | OmpA | SDVLFNFNK | 2 | y7 |
| 44 | 611.262 | 395.204 | OmpF | AGEYGSFDYGR | 2 | y3 |
| 45 | 611.262 | 744.331 | OmpF | AGEYGSFDYGR | 2 | y6 |
| 46 | 611.262 | 801.353 | OmpF | AGEYGSFDYGR | 2 | y7 |
| 47 | 611.262 | 964.416 | OmpF | AGEYGSFDYGR | 2 | y8 |
| 48 | 568.783 | 717.378 | OmpF | AGFSGGDADLVK | 2 | y7 |
| 49 | 568.783 | 774.399 | OmpF | AGFSGGDADLVK | 2 | y8 |
| 50 | 568.783 | 861.431 | OmpF | AGFSGGDADLVK | 2 | y9 |
| 51 | 686.804 | 755.321 | OmpF | FNQLDDNDYTK | 2 | y6 |
| 52 | 686.804 | 870.348 | OmpF | FNQLDDNDYTK | 2 | y7 |
| 53 | 686.804 | 983.432 | OmpF | FNQLDDNDYTK | 2 | y8 |
| 54 | 441.227 | 510.267 | OmpF | TNGVATYR | 2 | y4 |
| 55 | 441.227 | 609.336 | OmpF | TNGVATYR | 2 | y5 |
| 56 | 441.227 | 666.357 | OmpF | TNGVATYR | 2 | y6 |

The ionization source parameters are described in TABLE 16.

TABLE 16

| Transition number | Orifice potential (V) | Entry potential before Q0 (V) | Collision energy (eV) | Collision cell exit potential (V) |
|---|---|---|---|---|
| 1 | 71.1 | 10 | 27.4 | 9 |
| 2 | 71.1 | 10 | 27.4 | 9 |
| 3 | 71.1 | 10 | 27.4 | 9 |
| 4 | 78 | 10 | 32 | 9 |
| 5 | 78 | 10 | 32 | 9 |
| 6 | 78 | 10 | 32 | 9 |
| 7 | 71.3 | 10 | 28.7 | 9 |
| 8 | 71.3 | 10 | 28.7 | 9 |
| 9 | 71.3 | 10 | 28.7 | 9 |
| 10 | 73.4 | 10 | 29.7 | 9 |
| 11 | 73.4 | 10 | 29.7 | 9 |
| 12 | 73.4 | 10 | 29.7 | 9 |
| 13 | 73.4 | 10 | 29.7 | 9 |
| 14 | 60.8 | 10 | 23.5 | 9 |
| 15 | 60.8 | 10 | 23.5 | 9 |
| 16 | 60.8 | 10 | 23.5 | 9 |
| 17 | 60.8 | 10 | 23.5 | 9 |
| 18 | 80.5 | 10 | 34.4 | 9 |
| 19 | 80.5 | 10 | 34.4 | 9 |
| 20 | 80.5 | 10 | 34.4 | 9 |
| 21 | 80.5 | 10 | 34.4 | 9 |
| 22 | 63 | 10 | 24.6 | 9 |
| 23 | 63 | 10 | 24.6 | 9 |
| 24 | 63 | 10 | 24.6 | 9 |
| 25 | 63 | 10 | 24.6 | 9 |
| 26 | 92.5 | 10 | 39.1 | 9 |
| 27 | 92.5 | 10 | 39.1 | 9 |
| 28 | 92.5 | 10 | 39.1 | 9 |
| 29 | 74.6 | 10 | 30.3 | 9 |
| 30 | 74.6 | 10 | 30.3 | 9 |
| 31 | 74.6 | 10 | 30.3 | 9 |
| 32 | 74.6 | 10 | 30.3 | 9 |
| 33 | 76.8 | 10 | 31.4 | 9 |
| 34 | 76.8 | 10 | 31.4 | 9 |
| 35 | 76.8 | 10 | 31.4 | 9 |
| 36 | 76.8 | 10 | 31.4 | 9 |
| 37 | 61 | 10 | 23.6 | 9 |
| 38 | 61 | 10 | 23.6 | 9 |
| 39 | 61 | 10 | 23.6 | 9 |
| 40 | 70.6 | 10 | 28.4 | 9 |
| 41 | 70.6 | 10 | 28.4 | 9 |
| 42 | 70.6 | 10 | 28.4 | 9 |
| 43 | 70.6 | 10 | 28.4 | 9 |
| 44 | 75.7 | 10 | 30.9 | 9 |
| 45 | 75.7 | 10 | 30.9 | 9 |
| 46 | 75.7 | 10 | 30.9 | 9 |
| 47 | 75.7 | 10 | 30.9 | 9 |
| 48 | 72.6 | 10 | 29.3 | 9 |
| 49 | 72.6 | 10 | 29.3 | 9 |
| 50 | 72.6 | 10 | 29.3 | 9 |
| 51 | 81.2 | 10 | 33.6 | 9 |
| 52 | 81.2 | 10 | 33.6 | 9 |
| 53 | 81.2 | 10 | 33.6 | 9 |
| 54 | 63.3 | 10 | 24.7 | 9 |
| 55 | 63.3 | 10 | 24.7 | 9 |
| 56 | 63.3 | 10 | 24.7 | 9 |

The other parameters of the spectrometer that are used are the following:
Scan type: MRM
Scheduled MRM: yes
Polarity: Positive
Ionization source: Turbo VTM (AB Sciex)
Q1 setting: filtering with unit resolution
Q3 setting: filtering with unit resolution
Inter-scan pause: 5.00 msec
Scan speed: 10 Dais
Curtain gas: 50.00 psi
Cone voltage: 5500.00 V
Source temperature: 550.00° C.
Nebulizing gas: 50.00 psi
Heating gas: 40.00 psi
Collision-induced dissociation gas: 9.00 psi
Dynamic filling: inactivated
Total cycle time: 1.2 sec
Detection window: 90 sec The areas obtained for each of the transitions, at the specified retention time and for each of the microorganisms studied, were measured. When the area of a transition is greater than or equal to 3000 arbitrary units (a.u.), the detection of the transition is considered to be positive and its signal in arbitrary units is reported in TABLE 17. When the area of a transition is less than 3000 a.u., the detection of the transition is considered to be negative and is denoted "0" in TABLE 17.

TABLE 17

| Transition Number | Retention time (min) | Ech1 | Ech2 | Ech3 | Ech4 | Ech5 | Ech6 | Ech7 |
|---|---|---|---|---|---|---|---|---|
| 1 | 8.21 | 2602900 | 1135811 | 2043295 | 1749663 | 1674462 | 1585609 | 1355802 |
| 2 | 8.21 | 691147 | 285006 | 482299 | 424555 | 384233 | 364592 | 332529 |
| 3 | 8.21 | 603956 | 245497 | 417639 | 355878 | 324827 | 277666 | 280839 |
| 4 | 13.56 | 1589232 | 772328 | 1662133 | 1165768 | 1191490 | 1024854 | 1058062 |
| 5 | 13.56 | 813838 | 344901 | 638390 | 474985 | 481163 | 434691 | 423256 |
| 6 | 13.56 | 660863 | 318965 | 536804 | 430856 | 440272 | 345997 | 364280 |
| 7 | 12.07 | 597804 | 505306 | 236376 | 511016 | 378417 | 406026 | 372138 |
| 8 | 12.07 | 1291611 | 1094810 | 520779 | 1214566 | 822456 | 843819 | 788668 |
| 9 | 12.07 | 706081 | 759929 | 309939 | 687667 | 491624 | 520457 | 485558 |
| 10 | 17.29 | 385153 | 368340 | 226685 | 407656 | 310474 | 247360 | 323751 |
| 11 | 17.29 | 304112 | 310535 | 188282 | 349590 | 226314 | 224923 | 270712 |
| 12 | 17.29 | 699754 | 646563 | 420211 | 674373 | 511392 | 437452 | 558446 |
| 13 | 10.59 | 341891 | 347557 | 253847 | 418461 | 318267 | 296716 | 261781 |
| 14 | 10.59 | 261274 | 278913 | 201016 | 310809 | 250488 | 253221 | 216294 |
| 15 | 10.59 | 885464 | 939121 | 671103 | 1035831 | 875375 | 863389 | 813391 |
| 16 | 9.5 | 250472 | 231109 | 140189 | 281682 | 179053 | 146700 | 177904 |
| 17 | 9.5 | 764445 | 747671 | 490987 | 860209 | 590017 | 497323 | 520212 |
| 18 | 9.5 | 403711 | 352493 | 227892 | 453175 | 251970 | 263181 | 241959 |
| 19 | 7.55 | 22794 | 42877 | 201618 | 148180 | 25803 | 34431 | 66532 |
| 20 | 7.55 | 32057 | 51478 | 310930 | 208289 | 37545 | 48019 | 110222 |
| 21 | 7.55 | 21980 | 21335 | 144042 | 115419 | 17011 | 29434 | 57224 |

TABLE 17-continued

| | | | | | | | | |
|---|---|---|---|---|---|---|---|---|
| 22 | 7.55 | 21771 | 30432 | 171063 | 117314 | 23990 | 34970 | 61882 |
| 23 | 10.96 | 21459 | 41163 | 178441 | 128361 | 26789 | 31210 | 65820 |
| 24 | 10.96 | 26721 | 24791 | 148910 | 116984 | 19801 | 34184 | 64027 |
| 25 | 10.97 | 19129 | 42867 | 144327 | 135081 | 19983 | 34148 | 63955 |
| 26 | 10.97 | 84431 | 149295 | 728764 | 517076 | 86239 | 143900 | 272793 |
| 27 | 20.25 | 26516 | 28445 | 95314 | 139753 | 24336 | 20245 | 53755 |
| 28 | 20.25 | 33288 | 46900 | 193689 | 242948 | 42220 | 50043 | 106295 |
| 29 | 20.24 | 24975 | 37686 | 73554 | 112003 | 20636 | 36909 | 46319 |
| 30 | 20.23 | 12603 | 11781 | 39098 | 45394 | 15619 | 9993 | 22964 |
| 31 | 13.79 | 0 | 0 | 428755 | 324591 | 0 | 105409 | 141916 |
| 32 | 13.74 | 0 | 0 | 216751 | 165610 | 0 | 35262 | 134179 |
| 33 | 13.79 | 0 | 0 | 173261 | 113589 | 0 | 35440 | 59957 |
| 34 | 13.74 | 0 | 0 | 324871 | 318296 | 0 | 48402 | 179210 |
| 35 | 18.69 | 12484 | 17815 | 15635 | 24176 | 28003 | 21023 | 24919 |
| 36 | 18.68 | 10221 | 25568 | 8955 | 13393 | 19866 | 16092 | 17310 |
| 37 | 18.7 | 7938 | 7861 | 6593 | 14178 | 7251 | 12094 | 12662 |
| 38 | 16.6 | 6823783 | 7095173 | 4322553 | 7122446 | 7038371 | 6091649 | 5770195 |
| 39 | 16.6 | 13234716 | 14316980 | 8537852 | 14616872 | 14393343 | 12323927 | 11828717 |
| 40 | 16.6 | 4414593 | 4984167 | 3228275 | 4882250 | 4955076 | 4220413 | 3932741 |
| 41 | 16.6 | 17018861 | 17733765 | 10486877 | 17514993 | 18264156 | 15910007 | 14800049 |
| 42 | 13.33 | 20843351 | 24233983 | 14633316 | 21089701 | 22792467 | 18798003 | 18374834 |
| 43 | 13.34 | 17061688 | 20355792 | 12056353 | 16174324 | 18654047 | 15893940 | 14535503 |
| 44 | 13.33 | 19342185 | 23139911 | 13370591 | 19069750 | 19745073 | 17051971 | 15827141 |
| 45 | 13.34 | 5512710 | 7247720 | 4272088 | 5741809 | 6162840 | 5422699 | 5272579 |
| 46 | 14.54 | 265701 | 1168515 | 557899 | 1030702 | 349311 | 1299024 | 1945338 |
| 47 | 14.54 | 395416 | 1828630 | 960356 | 1722208 | 628930 | 2111329 | 3186586 |
| 48 | 14.54 | 682678 | 3104158 | 1564435 | 2873010 | 976208 | 3572083 | 5244566 |
| 49 | 17.03 | 8248555 | 7668553 | 4633613 | 6198627 | 6534736 | 6923653 | 7118401 |
| 50 | 17.03 | 20102696 | 18353666 | 11640756 | 15785641 | 17637157 | 18247283 | 17777482 |
| 51 | 17.03 | 16354432 | 14751562 | 10307458 | 13081573 | 13513838 | 14215725 | 14112799 |
| 52 | 17.03 | 4363285 | 3969736 | 2764420 | 3468815 | 3893693 | 3860568 | 3672677 |
| 53 | 12.15 | 0 | 0 | 0 | 0 | 0 | 85278 | 0 |
| 54 | 12.15 | 0 | 0 | 0 | 0 | 0 | 89676 | 0 |
| 55 | 12.15 | 0 | 0 | 0 | 0 | 0 | 230756 | 0 |
| 56 | 12.15 | 0 | 0 | 0 | 0 | 0 | 101523 | 0 |
| 57 | 12.63 | 0 | 0 | 0 | 0 | 0 | 112537 | 0 |
| 58 | 12.63 | 0 | 0 | 0 | 0 | 0 | 369953 | 0 |
| 59 | 12.63 | 0 | 0 | 0 | 0 | 0 | 392272 | 0 |
| 60 | 11.07 | 0 | 0 | 0 | 0 | 0 | 31824 | 0 |
| 61 | 11.07 | 0 | 0 | 0 | 0 | 0 | 102500 | 0 |
| 62 | 11.08 | 0 | 0 | 0 | 0 | 0 | 50013 | 0 |
| 63 | 7.3 | 0 | 0 | 0 | 0 | 0 | 268796 | 0 |
| 64 | 7.3 | 0 | 0 | 0 | 0 | 0 | 29511 | 0 |
| 65 | 7.3 | 0 | 0 | 0 | 0 | 0 | 60222 | 0 |

| Transition Number | Ech8 | Ech9 | Ech10 | Ech11 | Ech12 | Ech13 | Ech14 |
|---|---|---|---|---|---|---|---|
| 1 | 1735617 | 2191187 | 1707559 | 2176556 | 1631738 | 1635171 | 2495830 |
| 2 | 425099 | 539733 | 424604 | 518152 | 385313 | 412692 | 605460 |
| 3 | 352738 | 461850 | 348183 | 441057 | 318161 | 337446 | 493036 |
| 4 | 1254722 | 1747153 | 1294251 | 1415671 | 1352108 | 1181663 | 1888797 |
| 5 | 522667 | 729575 | 516737 | 688022 | 533924 | 527308 | 829485 |
| 6 | 475079 | 646123 | 462717 | 543303 | 502572 | 447866 | 763599 |
| 7 | 436373 | 515898 | 452980 | 420478 | 268442 | 558061 | 530580 |
| 8 | 1022282 | 1050848 | 975063 | 1013669 | 565911 | 1283957 | 1249293 |
| 9 | 574447 | 548716 | 605390 | 598449 | 338470 | 723065 | 732996 |
| 10 | 387635 | 347379 | 241777 | 379235 | 243647 | 403702 | 394797 |
| 11 | 327707 | 321914 | 187875 | 328347 | 198322 | 314347 | 315192 |
| 12 | 677733 | 602736 | 419494 | 651221 | 423337 | 717561 | 679091 |
| 13 | 281010 | 400839 | 300378 | 352239 | 241120 | 347371 | 537144 |
| 14 | 223729 | 316939 | 248301 | 268465 | 198992 | 277367 | 435580 |
| 15 | 778143 | 1036035 | 866950 | 857007 | 742315 | 977637 | 1446088 |
| 16 | 176637 | 275555 | 195036 | 271337 | 154441 | 217785 | 338233 |
| 17 | 574426 | 859168 | 567918 | 797482 | 448122 | 668638 | 1081072 |
| 18 | 280867 | 386354 | 275512 | 362660 | 241679 | 308258 | 527817 |
| 19 | 78831 | 23453 | 46530 | 26633 | 353334 | 58051 | 0 |
| 20 | 114327 | 40798 | 57896 | 33071 | 548761 | 85915 | 0 |
| 21 | 64057 | 23170 | 30713 | 23984 | 290918 | 40643 | 0 |
| 22 | 74055 | 26827 | 31168 | 25857 | 308266 | 45519 | 0 |
| 23 | 67684 | 40275 | 35592 | 28371 | 284750 | 49176 | 0 |
| 24 | 62573 | 31666 | 31985 | 29338 | 252856 | 47911 | 0 |
| 25 | 68235 | 25278 | 36277 | 19011 | 262190 | 53908 | 0 |
| 26 | 264296 | 119628 | 149990 | 107474 | 1161885 | 215385 | 0 |
| 27 | 83282 | 28086 | 25551 | 23361 | 258041 | 43989 | 11771 |
| 28 | 145502 | 37687 | 49198 | 35696 | 486885 | 84135 | 15498 |
| 29 | 65511 | 28916 | 29342 | 25842 | 179672 | 58527 | 14598 |
| 30 | 30920 | 12439 | 14732 | 11832 | 113822 | 21066 | 5949 |
| 31 | 160279 | 0 | 0 | 0 | 734655 | 119262 | 0 |
| 32 | 130839 | 0 | 0 | 0 | 403782 | 157519 | 0 |

TABLE 17-continued

| | | | | | | | |
|---|---|---|---|---|---|---|---|
| 33 | 67094 | 0 | 0 | 0 | 310682 | 38655 | 0 |
| 34 | 221336 | 0 | 0 | 0 | 759405 | 210945 | 0 |
| 35 | 29824 | 36592 | 21599 | 26365 | 21727 | 32439 | 35384 |
| 36 | 18552 | 24709 | 15786 | 15973 | 15705 | 19318 | 26474 |
| 37 | 13714 | 16068 | 7151 | 8450 | 7316 | 8752 | 11311 |
| 38 | 7807046 | 8826333 | 5766064 | 7208765 | 6107467 | 8646534 | 10398391 |
| 39 | 15699466 | 17997385 | 12827639 | 13818249 | 12222572 | 18239536 | 21730452 |
| 40 | 5319975 | 5634485 | 4613587 | 4772785 | 4409251 | 6149543 | 7449846 |
| 41 | 20457351 | 22084283 | 16026918 | 16994574 | 15710318 | 21976894 | 26544238 |
| 42 | 24668998 | 24928939 | 22225707 | 22372146 | 20207629 | 27691598 | 30802356 |
| 43 | 19211997 | 20639972 | 17707325 | 17741236 | 16925920 | 22659981 | 26311219 |
| 44 | 23748709 | 24494735 | 18832443 | 20549113 | 19225755 | 25390140 | 29319615 |
| 45 | 6795997 | 7813185 | 6210492 | 6348748 | 6098816 | 8044607 | 9157173 |
| 46 | 2097061 | 2514082 | 1479450 | 54274 | 2084443 | 2317251 | 1079249 |
| 47 | 3495187 | 4254235 | 2438774 | 89752 | 3472589 | 3802123 | 1892483 |
| 48 | 5377745 | 6843309 | 3848091 | 142623 | 5509593 | 6469904 | 2903631 |
| 49 | 7492835 | 10152365 | 7872583 | 6378013 | 5087023 | 11177637 | 9840259 |
| 50 | 18796824 | 25097722 | 20216262 | 16538603 | 13374262 | 27372458 | 24593515 |
| 51 | 14980515 | 20549684 | 16502607 | 13113796 | 11105624 | 21740608 | 19852094 |
| 52 | 4028991 | 5582634 | 4446618 | 3412893 | 2818500 | 5965451 | 5701247 |
| 53 | 0 | 0 | 0 | 0 | 0 | 93929 | 0 |
| 54 | 0 | 0 | 0 | 0 | 0 | 81137 | 0 |
| 55 | 0 | 0 | 0 | 0 | 0 | 241151 | 0 |
| 56 | 0 | 0 | 0 | 0 | 0 | 100430 | 0 |
| 57 | 0 | 0 | 0 | 0 | 0 | 109590 | 0 |
| 58 | 0 | 0 | 0 | 0 | 0 | 316425 | 0 |
| 59 | 0 | 0 | 0 | 0 | 0 | 361642 | 0 |
| 60 | 0 | 0 | 0 | 0 | 0 | 32578 | 0 |
| 61 | 0 | 0 | 0 | 0 | 0 | 74673 | 0 |
| 62 | 0 | 0 | 0 | 0 | 0 | 49581 | 0 |
| 63 | 0 | 0 | 0 | 0 | 0 | 317449 | 0 |
| 64 | 0 | 0 | 0 | 0 | 0 | 32859 | 0 |
| 65 | 0 | 0 | 0 | 0 | 0 | 68361 | 0 |

The areas of the transitions are added together per porin and per sample in order to estimate the amount thereof. Likewise, all of the areas of the transitions of the quantification proteins are added together in order to estimate the amount of bacteria. The ratio of the sum of the areas of the porins to the sum of the areas of the quantification peptides makes it possible to measure the relative expression level of the porin in the strain tested. This relative expression level per porin can also be expressed as percentage of the mean signal per porin over all of the strains. These results are described in TABLE 18.

TABLE 18

| Sample number | Amount of bacteria (a.u.) | Amount of LamB (a.u.) | Amount of OmpA (a.u.) | Amount of OmpF (a.u.) | LamB relative expression level (a.u.) |
|---|---|---|---|---|---|
| Ech1 | 13853707 | 378367 | 154664648 | 0 | 0.027 |
| Ech2 | 9684856 | 580293 | 169952312 | 0 | 0.060 |
| Ech3 | 9667867 | 3604570 | 103336842 | 0 | 0.373 |
| Ech4 | 11806742 | 3000635 | 150372720 | 0 | 0.254 |
| Ech5 | 9702294 | 415091 | 155539247 | 0 | 0.043 |
| Ech6 | 9033872 | 781207 | 145942273 | 1924861 | 0.086 |
| Ech7 | 8845582 | 1561942 | 144399606 | 0 | 0.177 |
| Ech8 | 10506912 | 1760911 | 179978696 | 0 | 0.168 |
| Ech9 | 12978103 | 515591 | 207413348 | 0 | 0.040 |
| Ech10 | 10090726 | 583509 | 161114560 | 0 | 0.058 |
| Ech11 | 12083349 | 441261 | 149535571 | 0 | 0.037 |
| Ech12 | 8788417 | 6754653 | 144359761 | 0 | 0.769 |
| Ech13 | 11339892 | 1391115 | 217644265 | 1879907 | 0.123 |
| Ech14 | 15344090 | 120985 | 227575767 | 0 | 0.008 |

| Sample number | OmpA relative expression level (a.u.) | OmpF relative expression level (a.u.) | Expression level relative of to the mean LamB expression level | Expression level relative of to the mean OmpA expression level | Expression level relative of to the mean OmpF expression level |
|---|---|---|---|---|---|
| Ech1 | 11.164 | 0 | 0.172 | 0.735 | 0 |
| Ech2 | 17.548 | 0 | 0.378 | 1.156 | 0 |
| Ech3 | 10.689 | 0 | 2.350 | 0.704 | 0 |
| Ech4 | 12.736 | 0 | 1.602 | 0.839 | 0 |
| Ech5 | 16.031 | 0 | 0.270 | 1.056 | 0 |
| Ech6 | 16.155 | 0.213 | 0.545 | 1.064 | 1.125 |
| Ech7 | 16.324 | 0 | 1.113 | 1.075 | 0 |
| Ech8 | 17.130 | 0 | 1.056 | 1.128 | 0 |
| Ech9 | 15.982 | 0 | 0.250 | 1.053 | 0 |
| Ech10 | 15.967 | 0 | 0.365 | 1.052 | 0 |

TABLE 18-continued

| | | | | | |
|---|---|---|---|---|---|
| Ech11 | 12.375 | 0 | 0.230 | 0.815 | 0 |
| Ech12 | 16.426 | 0 | 4.845 | 1.082 | 0 |
| Ech13 | 19.193 | 0.166 | 0.773 | 1.264 | 0.875 |
| Ech14 | 14.831 | 0 | 0.050 | 0.977 | 0 |

Particularly advantageously, the amounts of OmpA, OmpF, LamB and of bacteria were measured simultaneously using the same MRM method and it was thus possible to measure, in a single analysis, the relative expression level of these porins. For example, it is possible to very easily note that the Ech12 sample has a very high LamB expression level relative to the other samples, and that the Ech6 and Ech13 samples have a high OmpF expression level relative to the other samples.

LITERATURE REFERENCES

[1] J. Anhalt & C. Fenselau, 1975, Anal. Chem., 47(2): 219-225.
[2] A. Fox et al., eds., 1990, Analytical microbiology methods: chromatography and mass spectrometry, Plenum Press, New York, N.Y.
[3] M. Claydon et al, 1996, Nature Biotech. 14: 1584-1586.
[4] T. Krishnamurthy & P. Ross, 1996, Rapid Com. Mass Spec., 10: 1992-1996.
[5] P. Seng et al. 2009, Clin. Infect. Dis., 49: 543-551.
[6] A. Otto et al. 2012, Curr Opin Microbiol. 15(3): 364-72.
[7] P. Dalgaard et al. 1994, Int J Food Microbiol, 23(3-4): 391-404.
[8] T. J. Gentry et al. 2006, Microb Ecol., 52(2): 159-75.
[9] C. Y. Cohen et al. 1989, J Clin Microbiol, 27(6): 1250-1256.
[10] R. Everley et al., 2009, J. Microbiol. Methods, 77: 152-158.
[11] W.-J. Chen et al., 2008, Anal. Chem., 80: 9612-9621.
[12] D. Lopez-Ferrer et al., 2008, Anal. Chem., 80:8930-8936.
[13] D. Lopez-Ferrer et al., 2005, J. Proteome res., 4(5): 1569-1574.
[14] T. Fortin et al., 2009, Mol. Cell Proteomics, 8(5): 1006-1015.
[15] H. Keshishian et al., 2007, Mol. Cell Proteomics, 2212-2229.
[16] J. Stal-Zeng et al., 2007, Mol. Cell Proteomics, 1809-1817.
[17] Gaskell, Electrospray: principles and practice, 1997, J. Mass Spectrom., 32, 677-688.
[18] V. Fusaro et al., 2009, Nature Biotech. 27, 190-198.
[19] J. Mead et al., 15 Nov. 2008, Mol. Cell Proteomics, E-pub.
[20] F. Desiere et al., 2006, Nucleic Acids Res., 34(database issue): D655-8.
[21] L. Anderson & C. Hunter, 2006, Mol. Cell Proteomics, 573-588.
[22] B. Han & R. Higgs, 2008, Brief Funct Genomic Proteomic., 7(5): 340-54.
[23] K.-Y. Wang et al., 2008, Anal Chem, 80(16) 6159-6167.
[24] J. Bundy & C. Fenselau, 1999, Anal. Chem. 71: 1460-1463.
[25] J. D. Venable et al., 2004, Nat Methods. 1(1): 39-45.
[26] H. L. Rost et al., 2014 Nat Biotechnol. 32(3): 219-23.
[27] R. S. Plumb et al., 2006, Rapid Commun Mass Spectrom. 20(13): 1989-94.
[28] K.-C. Ho et al., 2004, Anal. Chem. 76: 7162-7268.
[29] Y. S. Lin et al., 2005, Anal. Chem., 77: 1753-1760.
[30] S. Vaidyanathan et al., 2001, Anal. Chem., 73: 4134-4144.
[31] P. Seng et al., 2009, Clin. Infect. Dis., 49: 543-551.
[32] Manes N. et al., 2007, Mol. & Cell. Proteomics, 6(4): 717-727.
[33] R. Nandakumar et al., 2009, Oral Microbiology Immunology, 24: 347-352.
[34] L. Hernychova et al., 2008, Anal. Chem., 80: 7097-7104.
[35] J.-M. Pratt et al., 2006, Nat. Protoc., 1: 1029-1043.
[36] V. Brun et al., 2007, Mol. Cell Proteomics, 2139-2149.
[37] M. Dupont et al., 2007, Antimicrobial agents and chemotherapy, 51: 3190-3198.

The invention claimed is:

1. A method for quantifying a microorganism from *Escherichia coli* species in a biological sample by mass spectrometry, the method comprising:

treating proteins of the microorganism by alkylation and digestion in order to fragment the proteins, thereby obtaining peptides including a proteotypic peptide having the amino acid sequence of SEQ ID NO:2, wherein the proteotypic peptide is representative of the *Escherichia coli* species and does not vary in amount due to the growth phase of the microorganism;

measuring an amount of the proteotypic peptide, as a quantification marker, using a mass spectrometer comprising a detector; and quantifying the microorganism based on an electrical signal produced by the detector.

2. The method of claim 1, wherein the electrical signal is processed using a computer to quantify the microorganism.

3. The method of claim 1, wherein the mass spectrometry is PRM, SRM, MRM, $MS^2$, $MRM^3$, DDA (data dependent acquisition) or DIA (data independent acquisition) mass spectrometry.

4. The method of claim 1, performed in less than one hour.

* * * * *

SEQUENCE LISTING

```
<160> NUMBER OF SEQ ID NOS: 36

<210> SEQ ID NO 1
<211> LENGTH: 891
<212> TYPE: PRT
<213> ORGANISM: Escherichia coli

<400> SEQUENCE: 1

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
```

-continued

```
                65                  70                  75                  80
Lys Asp Glu Lys Thr Cys Gly Val Leu Ser Glu Asp Thr Phe Gly
                    85                  90                  95

Thr Ile Thr Ile Ala Glu Pro Ile Gly Ile Ile Cys Gly Ile Val Pro
                    100                 105                 110

Thr Thr Asn Pro Thr Ser Thr Ala Ile Phe Lys Ser Leu Ile Ser Leu
                    115                 120                 125

Lys Thr Arg Asn Ala Ile Ile Phe Ser Pro His Pro Arg Ala Lys Asp
                    130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                    165                 170                 175

Leu Ser Asn Ala Leu Met His His Pro Asp Ile Asn Leu Ile Leu Ala
                    180                 185                 190

Thr Gly Gly Pro Gly Met Val Lys Ala Ala Tyr Ser Ser Gly Lys Pro
                    195                 200                 205

Ala Ile Gly Val Gly Ala Gly Asn Thr Pro Val Val Ile Asp Glu Thr
210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                    245                 250                 255

Ser Val Tyr Asp Ala Val Arg Glu Arg Phe Ala Thr His Gly Gly Tyr
                    260                 265                 270

Leu Leu Gln Gly Lys Glu Leu Lys Ala Val Gln Asp Val Ile Leu Lys
                    275                 280                 285

Asn Gly Ala Leu Asn Ala Ala Ile Val Gly Gln Pro Ala Tyr Lys Ile
                    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                    325                 330                 335

Leu Ser Pro Thr Leu Ala Met Tyr Arg Ala Lys Asp Phe Glu Asp Ala
                    340                 345                 350

Val Glu Lys Ala Glu Lys Leu Val Ala Met Gly Gly Ile Gly His Thr
                    355                 360                 365

Ser Cys Leu Tyr Thr Asp Gln Asp Asn Gln Pro Ala Arg Val Ser Tyr
                    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                    405                 410                 415

Leu Thr Leu Gly Cys Gly Ser Trp Gly Gly Asn Ser Ile Ser Glu Asn
                    420                 425                 430

Val Gly Pro Lys His Leu Ile Asn Lys Lys Thr Val Ala Lys Arg Ala
                    435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                    485                 490                 495
```

-continued

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
            820                 825                 830

Ser Glu Asp Ala Phe Asp Asp Gln Cys Thr Gly Ala Asn Pro Arg Tyr
835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
            885                 890

<210> SEQ ID NO 2
<211> LENGTH: 10

<212> TYPE: PRT
<213> ORGANISM: Escherichia coli

<400> SEQUENCE: 2

Asp Tyr Val Glu Gly Glu Thr Ala Ala Lys
1               5                   10

<210> SEQ ID NO 3
<211> LENGTH: 513
<212> TYPE: PRT
<213> ORGANISM: Staphylococcus aureus

<400> SEQUENCE: 3

Met Glu Met Ala Lys Glu Gln Glu Leu Ile Leu Val Leu Asp Phe Gly
1               5                   10                  15

Ser Gln Tyr Asn Gln Leu Ile Thr Arg Arg Ile Arg Glu Met Gly Val
                20                  25                  30

Tyr Ser Glu Leu His Asp His Glu Ile Ser Ile Glu Glu Ile Lys Lys
            35                  40                  45

Met Asn Pro Lys Gly Ile Ile Leu Ser Gly Gly Pro Asn Ser Val Tyr
        50                  55                  60

Glu Glu Gly Ser Phe Thr Ile Asp Pro Glu Ile Tyr Asn Leu Gly Ile
65                  70                  75                  80

Pro Val Leu Gly Ile Cys Tyr Gly Met Gln Leu Thr Thr Lys Leu Leu
                85                  90                  95

Gly Gly Lys Val Glu Arg Ala Asn Glu Arg Glu Tyr Gly Lys Ala Ile
            100                 105                 110

Ile Asn Ala Lys Ser Asp Glu Leu Phe Ala Gly Leu Pro Ala Glu Gln
        115                 120                 125

Thr Val Trp Met Ser His Ser Asp Lys Val Ile Glu Ile Pro Glu Gly
130                 135                 140

Phe Glu Val Ile Ala Asp Ser Pro Ser Thr Asp Tyr Ala Ala Ile Glu
145                 150                 155                 160

Asp Lys Lys Arg Arg Ile Tyr Gly Val Gln Phe His Pro Glu Val Arg
                165                 170                 175

His Thr Glu Tyr Gly Asn Asp Leu Leu Asn Asn Phe Val Arg Arg Val
            180                 185                 190

Cys Asp Cys Lys Gly Gln Trp Thr Met Glu Asn Phe Ile Glu Ile Glu
        195                 200                 205

Ile Glu Lys Ile Arg Gln Arg Val Gly Asp Arg Val Leu Cys Ala
210                 215                 220

Met Ser Gly Gly Val Asp Ser Ser Val Val Ala Val Leu Leu His Lys
225                 230                 235                 240

Ala Ile Gly Asp Gln Leu Thr Cys Ile Phe Val Asp His Gly Leu Leu
                245                 250                 255

Arg Lys Gly Glu Gly Asp Met Val Met Glu Gln Phe Gly Gly Phe
            260                 265                 270

Asn Met Asn Ile Ile Arg Val Asn Ala Lys Asp Arg Phe Met Asn Lys
        275                 280                 285

Leu Lys Gly Val Ser Asp Pro Glu Gln Lys Arg Lys Ile Ile Gly Asn
290                 295                 300

Glu Phe Val Tyr Val Phe Asp Asp Glu Ala Ser Lys Leu Lys Gly Val
305                 310                 315                 320

Asp Phe Leu Ala Gln Gly Thr Leu Tyr Thr Asp Val Ile Glu Ser Gly
                325                 330                 335

```
Thr Lys Thr Ala Gln Thr Ile Lys Ser His His Asn Val Gly Gly Leu
                340                 345                 350

Pro Glu Asp Met Glu Phe Glu Leu Ile Glu Pro Ile Asn Thr Leu Phe
            355                 360                 365

Lys Asp Glu Val Arg Lys Leu Gly Ile Glu Leu Gly Ile Pro Glu His
        370                 375                 380

Leu Val Trp Arg Gln Pro Phe Pro Gly Pro Gly Leu Gly Ile Arg Val
385                 390                 395                 400

Leu Gly Glu Ile Thr Glu Asp Lys Leu Glu Ile Val Arg Glu Ser Asp
                405                 410                 415

Ala Ile Leu Arg Gln Val Ile Arg Glu Glu Gly Leu Glu Arg Glu Ile
            420                 425                 430

Trp Gln Tyr Phe Thr Val Leu Pro Asn Ile Gln Ser Val Gly Val Met
        435                 440                 445

Gly Asp Tyr Arg Thr Tyr Asp His Thr Val Gly Ile Arg Ala Val Thr
450                 455                 460

Ser Ile Asp Gly Met Thr Ser Asp Phe Ala Arg Ile Asp Trp Glu Val
465                 470                 475                 480

Leu Gln Lys Ile Ser Ser Arg Ile Val Asn Glu Val Asp His Val Asn
                485                 490                 495

Arg Val Val Tyr Asp Ile Thr Ser Lys Pro Pro Ser Thr Ile Glu Trp
            500                 505                 510

Glu

<210> SEQ ID NO 4
<211> LENGTH: 14
<212> TYPE: PRT
<213> ORGANISM: Staphylococcus aureus

<400> SEQUENCE: 4

Leu Gly Ile Glu Leu Gly Ile Pro Glu His Leu Val Trp Arg
1               5                   10

<210> SEQ ID NO 5
<211> LENGTH: 446
<212> TYPE: PRT
<213> ORGANISM: Pseudomonas aeruginosa

<400> SEQUENCE: 5

Met Thr Arg Met Pro Leu Ala Thr Ala Ser Leu Leu Ala Leu Ala Ile
1               5                   10                  15

Ser Leu Ala Gly Cys Gly Asp Asp Lys Lys Ala Glu Ala Pro Ala Thr
            20                  25                  30

Pro Ala Ala Ser Thr Gln Pro Ala Ala Pro Ala Ala Pro Ala Ala
        35                  40                  45

Lys Val Asp Glu Ala Ala Ala Lys Ala Val Ile Lys Asn Tyr Ala Asp
    50                  55                  60

Leu Ala Glu Ala Thr Phe Ala Asp Ala Leu Ser Thr Ala Lys Asp Leu
65                  70                  75                  80

Gln Lys Ala Ile Asp Ala Phe Leu Ala Lys Pro Asp Ala Glu Thr Leu
                85                  90                  95

Lys Ala Ala Lys Glu Ala Trp Phe Ala Ala Arg Thr Pro Tyr Ser Gln
            100                 105                 110

Ser Glu Ala Phe Arg Phe Gly Asn Ala Ile Ile Asp Asp Trp Glu Gly
        115                 120                 125

Gln Val Asn Ala Trp Pro Leu Asp Glu Gly Leu Ile Asp Tyr Val Ala
```

```
                130               135               140
Lys Asp Tyr Gln His Ala Leu Gly Asn Pro Gly Ala Thr Ala Asn Ile
145                 150                 155                 160

Val Ala Asn Thr Glu Ile Gln Val Gly Glu Asp Lys Ile Asp Val Lys
                165                 170                 175

Glu Ile Thr Gly Glu Lys Leu Ala Ser Leu Asn Glu Leu Gly Gly Ser
                180                 185                 190

Glu Ala Asn Val Ala Thr Gly Tyr His Ala Ile Glu Phe Leu Leu Trp
                195                 200                 205

Gly Gln Asp Leu Asn Gly Thr Gly Pro Gly Ala Gly Asn Arg Pro Ala
    210                 215                 220

Thr Asp Tyr Ala Gln Gly Lys Asp Cys Thr Gly Gly His Cys Asp Arg
225                 230                 235                 240

Arg Ala Ala Tyr Leu Lys Ala Val Thr Asp Leu Leu Val Ser Asp Leu
                245                 250                 255

Glu Tyr Met Ala Gly Gln Trp Lys Ala Gly Val Ala Asp Asn Tyr Arg
                260                 265                 270

Ala Lys Leu Glu Ala Glu Pro Val Asp Thr Gly Leu Arg Lys Met Phe
    275                 280                 285

Phe Gly Met Gly Ser Leu Ser Leu Gly Glu Leu Ala Gly Glu Arg Met
    290                 295                 300

Lys Val Ala Leu Glu Ala Asn Ser Thr Glu Asp Glu His Asp Cys Phe
305                 310                 315                 320

Ser Asp Asp Thr His His Thr Leu Phe Phe Asn Gly Lys Ser Ile Arg
                325                 330                 335

Asn Ile Tyr Leu Gly Glu Tyr Lys Arg Ile Asp Gly Ser Val Val Lys
                340                 345                 350

Gly Pro Ser Leu Ala Asp Leu Val Ala Lys Ala Asp Ala Ala Ala Asn
    355                 360                 365

Asp Thr Leu Lys Ala Asp Leu Ala Asp Thr Glu Ala Lys Leu Gln Ala
    370                 375                 380

Ile Val Asp Ser Ala Glu Lys Asp Gly Val His Phe Asp Gln Met Ile
385                 390                 395                 400

Ala Pro Asp Asn Lys Asp Gly Gln Gln Lys Ile Arg Asp Ala Ile Ala
                405                 410                 415

Ala Leu Val Lys Gln Thr Gly Ala Ile Glu Gln Ala Ala Gly Lys Leu
                420                 425                 430

Gly Ile Gln Asp Leu Lys Pro Asp Asn Ala Asp His Glu Phe
    435                 440                 445

<210> SEQ ID NO 6
<211> LENGTH: 10
<212> TYPE: PRT
<213> ORGANISM: Pseudomonas aeruginosa

<400> SEQUENCE: 6

Ala Asp Ala Ala Ala Asn Asp Thr Leu Lys
1               5                   10

<210> SEQ ID NO 7
<211> LENGTH: 704
<212> TYPE: PRT
<213> ORGANISM: Artificial Sequence
<220> FEATURE:
<223> OTHER INFORMATION: Ubiquitary peptide for Enterobacteriae

<400> SEQUENCE: 7
```

```
Met Ala Arg Thr Thr Pro Ile Ala Arg Tyr Arg Asn Ile Gly Ile Ser
1               5                   10                  15

Ala His Ile Asp Ala Gly Lys Thr Thr Thr Glu Arg Ile Leu Phe
            20                  25                  30

Tyr Thr Gly Val Asn His Lys Ile Gly Glu Val His Asp Gly Ala Ala
            35                  40                  45

Thr Met Asp Trp Met Glu Gln Glu Gln Glu Arg Gly Ile Thr Ile Thr
    50                  55                  60

Ser Ala Ala Thr Thr Ala Phe Trp Ser Gly Met Ala Lys Gln Tyr Glu
65                  70                  75                  80

Pro His Arg Ile Asn Ile Ile Asp Thr Pro Gly His Val Asp Phe Thr
                85                  90                  95

Ile Glu Val Glu Arg Ser Met Arg Val Leu Asp Gly Ala Val Met Val
                100                 105                 110

Tyr Cys Ala Val Gly Gly Val Gln Pro Gln Ser Glu Thr Val Trp Arg
        115                 120                 125

Gln Ala Asn Lys Tyr Lys Val Pro Arg Ile Ala Phe Val Asn Lys Met
    130                 135                 140

Asp Arg Met Gly Ala Asn Phe Leu Lys Val Val Asn Gln Ile Lys Thr
145                 150                 155                 160

Arg Leu Gly Ala Asn Pro Val Pro Leu Gln Leu Ala Ile Gly Ala Glu
                165                 170                 175

Glu His Phe Thr Gly Val Val Asp Leu Val Lys Met Lys Ala Ile Asn
            180                 185                 190

Trp Asn Asp Ala Asp Gln Gly Val Thr Phe Glu Tyr Glu Asp Ile Pro
        195                 200                 205

Ala Asp Met Val Glu Leu Ala Asn Glu Trp His Gln Asn Leu Ile Glu
210                 215                 220

Ser Ala Ala Glu Ala Ser Glu Glu Leu Met Glu Lys Tyr Leu Gly Gly
225                 230                 235                 240

Glu Glu Leu Thr Glu Ala Glu Ile Lys Gly Ala Leu Arg Gln Arg Val
                245                 250                 255

Leu Asn Asn Glu Ile Ile Leu Val Thr Cys Gly Ser Ala Phe Lys Asn
            260                 265                 270

Lys Gly Val Gln Ala Met Leu Asp Ala Val Ile Asp Tyr Leu Pro Ser
        275                 280                 285

Pro Val Asp Val Pro Ala Ile Asn Gly Ile Leu Asp Asp Gly Lys Asp
    290                 295                 300

Thr Pro Ala Glu Arg His Ala Ser Asp Asp Glu Pro Phe Ser Ala Leu
305                 310                 315                 320

Ala Phe Lys Ile Ala Thr Asp Pro Phe Val Gly Asn Leu Thr Phe Phe
                325                 330                 335

Arg Val Tyr Ser Gly Val Val Asn Ser Gly Asp Thr Val Leu Asn Ser
            340                 345                 350

Val Lys Ala Ala Arg Glu Arg Phe Gly Arg Ile Val Gln Met His Ala
        355                 360                 365

Asn Lys Arg Glu Glu Ile Lys Glu Val Arg Ala Gly Asp Ile Ala Ala
    370                 375                 380

Ala Ile Gly Leu Lys Asp Val Thr Thr Gly Asp Thr Leu Cys Asp Pro
385                 390                 395                 400

Asp Ala Pro Ile Ile Leu Glu Arg Met Glu Phe Pro Glu Pro Val Ile
                405                 410                 415
```

```
Ser Ile Ala Val Glu Pro Lys Thr Lys Ala Asp Gln Glu Lys Met Gly
                420                 425                 430

Leu Ala Leu Gly Arg Leu Ala Lys Glu Asp Pro Ser Phe Arg Val Trp
            435                 440                 445

Thr Asp Glu Glu Ser Asn Gln Thr Ile Ile Ala Gly Met Gly Glu Leu
        450                 455                 460

His Leu Asp Ile Ile Val Asp Arg Met Lys Arg Glu Phe Asn Val Glu
465                 470                 475                 480

Ala Asn Val Gly Lys Pro Gln Val Ala Tyr Arg Glu Thr Ile Arg Gln
                485                 490                 495

Lys Val Thr Asp Val Glu Gly Lys His Ala Lys Gln Ser Gly Gly Arg
            500                 505                 510

Gly Gln Tyr Gly His Val Val Ile Asp Met Tyr Pro Leu Glu Pro Gly
        515                 520                 525

Ser Asn Pro Lys Gly Tyr Glu Phe Ile Asn Asp Ile Lys Gly Gly Val
        530                 535                 540

Ile Pro Gly Glu Tyr Ile Pro Ala Val Asp Lys Gly Ile Gln Glu Gln
545                 550                 555                 560

Leu Lys Ala Gly Pro Leu Ala Gly Tyr Pro Val Val Asp Met Gly Ile
                565                 570                 575

Arg Leu His Phe Gly Ser Tyr His Asp Val Asp Ser Ser Glu Leu Ala
            580                 585                 590

Phe Lys Leu Ala Ala Ser Ile Ala Phe Lys Glu Gly Phe Lys Lys Ala
        595                 600                 605

Lys Pro Val Leu Leu Glu Pro Ile Met Lys Val Glu Val Glu Thr Pro
610                 615                 620

Glu Glu Asn Thr Gly Asp Val Ile Gly Asp Leu Ser Arg Arg Arg Gly
625                 630                 635                 640

Met Leu Lys Gly Gln Glu Ser Glu Val Thr Gly Val Lys Ile His Ala
                645                 650                 655

Glu Val Pro Leu Ser Glu Met Phe Gly Tyr Ala Thr Gln Leu Arg Ser
            660                 665                 670

Leu Thr Lys Gly Arg Ala Ser Tyr Thr Met Glu Phe Leu Lys Tyr Asp
        675                 680                 685

Glu Ala Pro Ser Asn Val Ala Gln Ala Val Ile Glu Ala Arg Gly Lys
        690                 695                 700

<210> SEQ ID NO 8
<211> LENGTH: 11
<212> TYPE: PRT
<213> ORGANISM: Artificial Sequence
<220> FEATURE:
<223> OTHER INFORMATION: Ubiquitary peptide for Enterobacteriae

<400> SEQUENCE: 8

Ala Gly Asp Ile Ala Ala Ala Ile Gly Leu Lys
1               5                   10

<210> SEQ ID NO 9
<211> LENGTH: 62
<212> TYPE: PRT
<213> ORGANISM: Artificial Sequence
<220> FEATURE:
<223> OTHER INFORMATION: Ubiquitary protein

<400> SEQUENCE: 9

Met Lys Val Lys Glu Ile Arg Glu Leu Thr Thr Ala Glu Met Leu Asp
1               5                   10                  15
```

Lys Glu Lys Gln Leu Lys Glu Glu Leu Phe Asn Leu Arg Phe Gln Leu
            20                  25                  30

Ala Thr Gly Gln Leu Glu Asn Thr Ala Arg Ile Lys Glu Val Arg Gln
        35                  40                  45

Ser Ile Ala Arg Ile Lys Thr Val Leu Arg Glu Gln Ala Asn
    50                  55                  60

<210> SEQ ID NO 10
<211> LENGTH: 13
<212> TYPE: PRT
<213> ORGANISM: Artificial Sequence
<220> FEATURE:
<223> OTHER INFORMATION: Ubiquitary peptide

<400> SEQUENCE: 10

Phe Gln Leu Ala Thr Gly Gln Leu Glu Asn Thr Ala Arg
1               5                   10

<210> SEQ ID NO 11
<211> LENGTH: 115
<212> TYPE: PRT
<213> ORGANISM: Artificial Sequence
<220> FEATURE:
<223> OTHER INFORMATION: Ubiquitary protein

<400> SEQUENCE: 11

Met Ser Glu Gln Ile Thr Ser Ala Lys Ala Thr Ala Lys Thr Val Arg
1               5                   10                  15

Thr Ser Pro Arg Lys Ala Arg Leu Val Ile Asp Leu Ile Arg Gly Lys
            20                  25                  30

Ser Val Ala Asp Ala Ile Ser Ile Leu Lys Phe Thr Pro Asn Lys Ser
        35                  40                  45

Ala Gly Ile Ile Glu Lys Val Leu Met Ser Ala Val Ala Asn Ala Glu
    50                  55                  60

Asn Asn Phe Asp Leu Asp Val Glu Ser Leu Val Val Ser Glu Ala Phe
65                  70                  75                  80

Val Asn Glu Gly Pro Thr Met Lys Arg Phe Arg Pro Arg Ala Lys Gly
                85                  90                  95

Ser Ala Ser Pro Ile Asn Lys Arg Thr Ser His Ile Thr Val Val Val
            100                 105                 110

Thr Glu Lys
        115

<210> SEQ ID NO 12
<211> LENGTH: 7
<212> TYPE: PRT
<213> ORGANISM: Artificial Sequence
<220> FEATURE:
<223> OTHER INFORMATION: Ubiquitary peptide

<400> SEQUENCE: 12

Leu Val Ile Asp Leu Ile Arg
1               5

<210> SEQ ID NO 13
<211> LENGTH: 92
<212> TYPE: PRT
<213> ORGANISM: Artificial Sequence
<220> FEATURE:
<223> OTHER INFORMATION: Ubiquitary protein

<400> SEQUENCE: 13

```
Met Gly Arg Ser Leu Lys Lys Gly Pro Phe Val Asp Asp His Leu Met
1               5                   10                  15

Lys Lys Val Glu Ala Gln Gln Gly Ala Glu Lys Lys Val Ile Lys
            20                  25                  30

Thr Trp Ser Arg Arg Ser Thr Ile Phe Pro Ser Phe Val Gly Phe Thr
        35                  40                  45

Ile Ala Val Tyr Asp Gly Arg Lys His Val Pro Val Tyr Ile Gln Glu
    50                  55                  60

Asp Met Val Gly His Lys Leu Gly Glu Phe Ala Pro Thr Arg Thr Tyr
65                  70                  75                  80

Arg Gly His Val Ala Asp Asp Lys Lys Thr Lys Arg
                85                  90
```

```
<210> SEQ ID NO 14
<211> LENGTH: 8
<212> TYPE: PRT
<213> ORGANISM: Artificial Sequence
<220> FEATURE:
<223> OTHER INFORMATION: Ubiquitary peptide

<400> SEQUENCE: 14

Leu Gly Glu Phe Ala Pro Thr Arg
1               5
```

```
<210> SEQ ID NO 15
<211> LENGTH: 890
<212> TYPE: PRT
<213> ORGANISM: Klebsiella pneumoniae

<400> SEQUENCE: 15

Met Ser Ser Thr Leu Arg Glu Ala Ser Lys Asp Thr Leu Gln Val Asn
1               5                   10                  15

Asp Lys Thr Trp His Tyr Tyr Ser Leu Pro Leu Ala Glu Lys Gln Leu
            20                  25                  30

Gly Glu Ile Ser Arg Leu Pro Lys Ser Leu Lys Val Leu Met Glu Asn
        35                  40                  45

Leu Leu Arg Trp Gln Asp Gly Asp Ser Val Thr Glu Glu Asp Ile Arg
    50                  55                  60

Ala Leu Ala Gly Trp Leu Gln Gln Ala His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
            100                 105                 110

Asp Thr Ala Lys Val Asn Pro Leu Ser Pro Val Asp Leu Val Ile Asp
        115                 120                 125

His Ser Val Thr Val Asp Arg Phe Gly Asp Asp Glu Ala Phe Glu Asp
130                 135                 140

Asn Val Arg Leu Glu Met Glu Arg Asn His Glu Arg Tyr Ala Phe Leu
145                 150                 155                 160

Arg Trp Gly Gln Gln Ala Phe Ser Arg Phe Ser Val Val Pro Pro Gly
                165                 170                 175

Thr Gly Ile Cys His Gln Val Asn Leu Glu Tyr Leu Gly Arg Ala Val
            180                 185                 190

Trp Ser Glu Glu Val Asn Gly Gln Trp Met Ala Trp Pro Asp Thr Leu
        195                 200                 205
```

```
Val Gly Thr Asp Ser His Thr Thr Met Ile Asn Gly Leu Gly Val Leu
210                 215                 220
Gly Trp Gly Val Gly Gly Ile Glu Ala Glu Ala Ala Met Leu Gly Gln
225                 230                 235                 240
Pro Val Ser Met Leu Ile Pro Asp Val Gly Phe Lys Leu Ser Gly
            245                 250                 255
Lys Leu Arg Glu Gly Ile Thr Ala Thr Asp Leu Val Leu Thr Val Thr
            260                 265                 270
Gln Met Leu Arg Gln His Gly Val Gly Lys Phe Val Glu Phe Tyr
        275                 280                 285
Gly Asp Gly Leu Asp Thr Leu Pro Leu Ala Asp Arg Ala Thr Ile Ala
290                 295                 300
Asn Met Ala Pro Glu Tyr Gly Ala Thr Cys Gly Phe Pro Ile Asp
305             310                 315                 320
Asp Val Thr Leu Ser Tyr Met Arg Leu Ser Gly Arg Ser Glu Glu Gln
                325                 330                 335
Val Ala Leu Val Glu Ala Tyr Ala Lys Ala Gln Gly Met Trp Arg Gln
            340                 345                 350
Pro Gly Asp Glu Pro Val Phe Thr Ser Thr Leu Ala Leu Asp Met Ser
        355                 360                 365
Ser Val Glu Ala Ser Leu Ala Gly Pro Lys Arg Pro Gln Asp Arg Val
370                 375                 380
Ala Leu Gly Asp Val Pro Lys Ala Phe Ala Ala Ser Gly Glu Leu Glu
385                 390                 395                 400
Val Asn His Leu Gln Arg Gln Arg Gln Pro Val Asp Tyr Thr Leu Asn
            405                 410                 415
Gly His His Tyr Ser Leu Pro Asp Gly Ala Val Ala Ile Ala Ala Ile
        420                 425                 430
Thr Ser Cys Thr Asn Thr Ser Asn Pro Ser Val Leu Met Ala Ala Gly
        435                 440                 445
Leu Leu Ala Lys Lys Ala Val Glu Arg Gly Leu Gln Pro Gln Pro Trp
450                 455                 460
Val Lys Ala Ser Leu Ala Pro Gly Ser Lys Val Val Ser Asp Tyr Leu
465                 470                 475                 480
Ala His Ala Gly Leu Thr Pro Tyr Leu Asp Gln Leu Gly Phe Asn Leu
            485                 490                 495
Val Gly Tyr Gly Cys Thr Thr Cys Ile Gly Asn Ser Gly Pro Leu Pro
        500                 505                 510
Glu Pro Ile Glu Glu Ala Ile Lys Lys Gly Asp Leu Thr Val Gly Ala
        515                 520                 525
Val Leu Ser Gly Asn Arg Asn Phe Glu Gly Arg Ile His Pro Leu Val
530                 535                 540
Lys Thr Asn Trp Leu Ala Ser Pro Pro Leu Val Val Ala Tyr Ala Leu
545                 550                 555                 560
Ala Gly Asn Met Asn Ile Asp Leu Thr Arg Glu Pro Leu Gly Gln Gly
            565                 570                 575
Lys Asn Gly Glu Pro Val Tyr Leu Lys Asp Ile Trp Pro Ser Gly Glu
        580                 585                 590
Glu Ile Ala Arg Ala Val Glu Gln Val Ser Thr Glu Met Phe Arg Lys
        595                 600                 605
Glu Tyr Ala Glu Val Phe Ser Gly Thr Glu Trp Lys Ala Ile Lys
610                 615                 620
Val Glu Ala Ser Asp Thr Tyr Asp Trp Gln Glu Asp Ser Thr Tyr Ile
```

```
                625                 630                 635                 640
Arg Leu Ser Pro Phe Phe Asp Glu Met Gly Ala Glu Pro Leu Pro Val
                    645                 650                 655
Glu Asp Ile Arg Gly Ala Arg Ile Leu Ala Met Leu Gly Asp Ser Val
                660                 665                 670
Thr Thr Asp His Ile Ser Pro Ala Gly Ser Ile Lys Ala Asp Ser Pro
            675                 680                 685
Ala Gly Arg Tyr Leu Gln Glu His Gly Val Ala Arg Arg Asp Phe Asn
        690                 695                 700
Ser Tyr Gly Ser Arg Arg Gly Asn His Glu Val Met Met Arg Gly Thr
705                 710                 715                 720
Phe Ala Asn Ile Arg Ile Arg Asn Glu Met Val Pro Gly Val Glu Gly
                725                 730                 735
Gly Met Thr Arg His Leu Pro Asp Pro Glu Pro Met Ala Ile Tyr Asp
            740                 745                 750
Ala Ala Met Leu Tyr Lys Ala Glu Gly Thr Pro Leu Ala Val Ile Ala
        755                 760                 765
Gly Lys Glu Tyr Gly Ser Gly Ser Ser Arg Asp Trp Ala Ala Lys Gly
    770                 775                 780
Pro Arg Leu Leu Gly Ile Arg Val Val Ile Ala Glu Ser Phe Glu Arg
785                 790                 795                 800
Ile His Arg Ser Asn Leu Ile Gly Met Gly Ile Leu Pro Leu Glu Phe
                805                 810                 815
Pro Gln Gly Val Thr Arg Lys Thr Leu Arg Leu Thr Gly Glu Glu Arg
            820                 825                 830
Ile Asp Ile Ser Asn Leu Gln Ser Leu Gln Pro Gly Ala Thr Val Pro
        835                 840                 845
Val Thr Leu Thr Arg Ala Asp Gly Ser Gln Glu Ala Ile Pro Cys Arg
    850                 855                 860
Cys Arg Ile Asp Thr Ala Thr Glu Leu Thr Tyr Tyr Arg Asn Asp Gly
865                 870                 875                 880
Ile Leu His Tyr Val Ile Arg Asn Met Leu
                885                 890

<210> SEQ ID NO 16
<211> LENGTH: 15
<212> TYPE: PRT
<213> ORGANISM: Klebsiella pneumoniae

<400> SEQUENCE: 16

Ala Phe Ala Ala Ser Gly Glu Leu Glu Val Asn His Leu Gln Arg
1               5                   10                  15

<210> SEQ ID NO 17
<211> LENGTH: 875
<212> TYPE: PRT
<213> ORGANISM: Klebsiella pneumoniae

<400> SEQUENCE: 17

Met Ser Lys Ser Thr Ala Glu Ile Arg Gln Ala Phe Leu Asp Phe
1               5                   10                  15

His Ser Lys Gly His Gln Val Val Ala Ser Ser Leu Val Pro His
            20                  25                  30

Asn Asp Pro Thr Leu Leu Phe Thr Asn Ala Gly Met Asn Gln Phe Lys
        35                  40                  45

Asp Val Phe Leu Gly Leu Asp Lys Arg Asn Tyr Ser Arg Ala Thr Thr
```

```
                50                  55                  60
Ala Gln Arg Cys Val Arg Ala Gly Gly Lys His Asn Asp Leu Glu Asn
 65                  70                  75                  80

Val Gly Tyr Thr Ala Arg His His Thr Phe Glu Met Leu Gly Asn
                     85                  90                  95

Phe Ser Phe Gly Asp Tyr Phe Lys Gln Asp Ala Ile Lys Tyr Ala Trp
                100                 105                 110

Glu Leu Leu Thr Gly Glu Asn Trp Phe Ala Leu Pro Lys Glu Lys Leu
                115                 120                 125

Trp Val Thr Val Tyr Glu Thr Asp Asp Glu Ala Phe Asp Ile Trp Ala
                130                 135                 140

Asn Glu Val Gly Val Pro Arg Glu Arg Ile Ile Arg Ile Gly Asp Asn
145                 150                 155                 160

Lys Gly Ala Pro Phe Ala Ser Asp Asn Phe Trp Gln Met Gly Asp Thr
                165                 170                 175

Gly Pro Cys Gly Pro Cys Thr Glu Ile Phe Phe Asp His Gly Asp His
                180                 185                 190

Ile Trp Gly Gly Pro Pro Gly Ser Pro Glu Glu Asp Gly Asp Arg Tyr
                195                 200                 205

Ile Glu Ile Trp Asn Ile Val Phe Met Gln Phe Asn Arg Gln Ala Asp
210                 215                 220

Gly Thr Met Glu Pro Leu Pro Lys Pro Ser Val Asp Thr Gly Met Gly
225                 230                 235                 240

Leu Glu Arg Ile Ala Ala Val Leu Gln His Val Asn Ser Asn Tyr Asp
                245                 250                 255

Ile Asp Leu Phe Arg Asp Leu Ile Ala Ser Val Ala Lys Val Thr Gly
                260                 265                 270

Ala Thr Asp Leu Thr Asn Lys Ser Leu Arg Val Ile Ala Asp His Ile
                275                 280                 285

Arg Ser Cys Ala Phe Leu Val Ala Asp Gly Val Ile Pro Ser Asn Glu
290                 295                 300

Asn Arg Gly Tyr Val Leu Arg Arg Ile Ile Arg Arg Ala Ile Arg His
305                 310                 315                 320

Gly Asn Met Leu Gly Ala Lys Asp Thr Phe Phe Trp Lys Leu Val Ala
                325                 330                 335

Pro Leu Ile Asp Val Met Gly Ser Ala Gly Asp Glu Leu Lys Gln Gln
                340                 345                 350

Gln Ala Gln Val Glu Gln Val Leu Lys Thr Glu Glu Glu Gln Phe Ala
                355                 360                 365

Arg Thr Leu Glu Arg Gly Leu Ala Leu Leu Asp Glu Glu Leu Ser Lys
                370                 375                 380

Leu Lys Gly Asp Thr Leu Asp Gly Glu Thr Ala Phe Arg Leu Tyr Asp
385                 390                 395                 400

Thr Tyr Gly Phe Pro Val Asp Leu Thr Ala Asp Val Cys Arg Glu Arg
                405                 410                 415

Asn Ile Lys Val Asp Glu Ala Gly Phe Glu Ala Ala Met Glu Glu Gln
                420                 425                 430

Arg Arg Arg Ala Arg Glu Ser Ser Gly Phe Gly Ala Asp Tyr Asn Ala
                435                 440                 445

Met Ile Arg Val Asp Gly Ala Ser Glu Phe Lys Gly Tyr Asp His Leu
                450                 455                 460

Glu Leu Asn Gly Lys Val Thr Ala Leu Phe Ile Asp Gly Lys Ala Val
465                 470                 475                 480
```

Asp Ser Val Ser Ala Gly Gln Glu Ala Val Val Ile Leu Asp Gln Thr
            485                 490                 495

Pro Phe Tyr Ala Glu Ser Gly Gly Gln Val Gly Asp Lys Gly Glu Leu
            500                 505                 510

Lys Gly Ala Gly Phe Ser Phe Ala Val Ser Asp Thr Gln Lys Tyr Gly
            515                 520                 525

Gln Ala Ile Gly His Ile Gly Lys Val Ala Ser Gly Thr Leu Lys Val
            530                 535                 540

Gly Asp Ala Val Gln Ala Asp Val Asp Glu Ala Arg Arg Gln Arg Ile
545                 550                 555                 560

Arg Leu Asn His Ser Ala Thr His Leu Met His Ala Ala Leu Arg Gln
                565                 570                 575

Val Leu Gly Thr His Val Ala Gln Lys Gly Ser Leu Val Asn Asp Lys
                580                 585                 590

Ala Leu Arg Phe Asp Phe Ser His Phe Glu Ala Met Lys Pro Glu Glu
                595                 600                 605

Ile Arg Ala Val Glu Asp Leu Val Asn Ala Gln Ile Arg Arg Asn Leu
            610                 615                 620

Ala Ile Glu Thr Asn Ile Met Asp Ile Asp Ala Ala Arg Ala Ser Gly
625                 630                 635                 640

Ala Met Ala Leu Phe Gly Glu Lys Tyr Asp Asp Arg Val Arg Val Leu
                645                 650                 655

Arg Met Gly Asp Phe Ser Thr Glu Leu Cys Gly Gly Thr His Ala Ala
                660                 665                 670

Arg Thr Gly Asp Ile Gly Leu Phe Arg Ile Thr Ser Glu Ser Gly Thr
                675                 680                 685

Ala Ala Gly Val Arg Arg Ile Glu Ala Val Thr Gly Glu Gly Ala Met
            690                 695                 700

Ala Ile Leu His Ala Gln Ser Asp Gln Leu Asn Asp Ile Ala Gln Leu
705                 710                 715                 720

Leu Lys Gly Asp Ser His Asn Leu Gly Glu Lys Val Arg Ala Ala Leu
                725                 730                 735

Glu Arg Thr Arg Gln Leu Glu Lys Glu Leu Gln Gln Leu Lys Glu Gln
                740                 745                 750

Ala Ala Ala Gln Glu Ser Ala Asn Leu Ser Ser Lys Ala Glu Glu Ile
                755                 760                 765

Asn Gly Val Lys Leu Leu Val Ser Glu Leu Thr Gly Val Glu Pro Lys
770                 775                 780

Met Leu Arg Thr Met Val Asp Asp Leu Lys Asn Gln Leu Gly Ser Thr
785                 790                 795                 800

Ile Val Val Leu Ala Thr Val Ala Asp Gly Lys Val Ser Leu Ile Ala
                805                 810                 815

Gly Val Ser Lys Asp Val Thr Asp Arg Val Lys Ala Gly Glu Leu Val
                820                 825                 830

Gly Met Val Ala Gln Gln Val Gly Gly Lys Gly Gly Arg Pro Asp
                835                 840                 845

Met Ala Gln Ala Gly Gly Thr Asp Ala Ser Ala Leu Pro Ala Ala Leu
            850                 855                 860

Ala Ser Val Lys Gly Trp Val Ser Ala Lys Leu
865                 870                 875

<210> SEQ ID NO 18
<211> LENGTH: 12

<212> TYPE: PRT
<213> ORGANISM: Klebsiella pneumoniae

<400> SEQUENCE: 18

Leu Leu Val Ser Glu Leu Thr Gly Val Glu Pro Lys
1               5                   10

<210> SEQ ID NO 19
<211> LENGTH: 353
<212> TYPE: PRT
<213> ORGANISM: Klebsiella pneumoniae

<400> SEQUENCE: 19

Met Asn Asn Gln Val Leu Ile Asn Pro Ser Asn Glu Gln Ile Glu Ala
1               5                   10                  15

Leu Arg Ser Leu Gln Ala Gln Val Ala Glu Glu Lys Ala Glu Leu Ala
                20                  25                  30

Lys Leu Lys Asp Leu Pro Ala Ile Thr Leu Asp Gly His Gln Val Glu
            35                  40                  45

Val Cys Ala Asn Ile Gly Thr Val Arg Asp Val Glu Gly Ala Glu Arg
        50                  55                  60

Asn Gly Ala Glu Gly Val Gly Leu Tyr Arg Thr Glu Phe Leu Phe Met
65                  70                  75                  80

Asp Arg Asp Ala Leu Pro Thr Glu Glu Gln Phe Ala Ala Tyr Lys
                85                  90                  95

Ala Val Ala Glu Ala Cys Gly Ser Gln Ala Val Ile Val Arg Thr Met
            100                 105                 110

Asp Ile Gly Gly Asp Lys Glu Leu Pro Tyr Met Asn Phe Pro Lys Glu
        115                 120                 125

Glu Asn Pro Phe Leu Gly Trp Arg Ala Val Arg Ile Ala Met Asp Arg
130                 135                 140

Lys Glu Ile Leu Arg Asp Gln Val Arg Ala Ile Leu Arg Ala Ser Ala
145                 150                 155                 160

Phe Gly Lys Leu Arg Ile Met Phe Pro Met Ile Ile Ser Val Glu Glu
                165                 170                 175

Val Arg Ala Leu Lys Lys Glu Ile Glu Ile Tyr Lys Gln Glu Leu Arg
            180                 185                 190

Asp Glu Gly Lys Ala Phe Asp Glu Ser Ile Glu Ile Gly Val Met Val
        195                 200                 205

Glu Thr Pro Ala Ala Thr Ile Ala Arg His Leu Ala Lys Glu Val
    210                 215                 220

Asp Phe Phe Ser Ile Gly Thr Asn Asp Leu Thr Gln Tyr Thr Leu Ala
225                 230                 235                 240

Val Asp Arg Gly Asn Asp Met Ile Ser Tyr Leu Tyr Gln Pro Met Ser
                245                 250                 255

Pro Ser Val Leu Asn Leu Ile Lys Gln Val Ile Asp Ala Ser His Ala
            260                 265                 270

Glu Gly Lys Trp Thr Gly Met Cys Gly Glu Leu Ala Gly Asp Glu Arg
        275                 280                 285

Ala Thr Leu Leu Leu Leu Gly Met Gly Leu Asp Glu Phe Ser Met Ser
    290                 295                 300

Ala Ile Ser Ile Pro Arg Ile Lys Lys Ile Ile Arg Asn Thr Asn Phe
305                 310                 315                 320

Glu Asp Ala Lys Val Leu Ala Glu Gln Ala Leu Ala Gln Pro Thr Thr
                325                 330                 335

-continued

Asp Glu Leu Met Thr Leu Val Asn Lys Phe Ile Glu Lys Thr Ile
            340                 345                 350

Cys

<210> SEQ ID NO 20
<211> LENGTH: 10
<212> TYPE: PRT
<213> ORGANISM: Klebsiella pneumoniae

<400> SEQUENCE: 20

Ser Leu Gln Ala Gln Val Ala Glu Glu Lys
1               5                   10

<210> SEQ ID NO 21
<211> LENGTH: 429
<212> TYPE: PRT
<213> ORGANISM: Klebsiella pneumoniae

<400> SEQUENCE: 21

Met Met Ile Thr Leu Arg Lys Leu Pro Leu Ala Val Ala Val Ala Ala
1               5                   10                  15

Gly Val Met Ser Ala Gln Ala Leu Ala Val Asp Phe His Gly Tyr Ala
                20                  25                  30

Arg Ser Gly Ile Gly Trp Thr Gly Ser Gly Gly Glu Gln Gln Cys Phe
            35                  40                  45

Lys Ala Thr Gly Ala Gln Ser Lys Tyr Arg Leu Gly Asn Glu Cys Glu
        50                  55                  60

Thr Tyr Ala Glu Leu Lys Leu Gly Gln Glu Leu Trp Lys Glu Gly Asp
65                  70                  75                  80

Lys Ser Phe Tyr Phe Asp Thr Asn Val Ala Tyr Ser Val Asn Gln Glu
                85                  90                  95

Asp Asp Trp Glu Ser Thr Ser Pro Ala Phe Arg Glu Ala Asn Ile Gln
            100                 105                 110

Gly Lys Asn Leu Ile Asp Trp Leu Pro Gly Ser Thr Leu Trp Ala Gly
        115                 120                 125

Lys Arg Phe Tyr Gln Arg His Asp Val His Met Ile Asp Phe Tyr Tyr
    130                 135                 140

Trp Asp Ile Ser Gly Pro Gly Ala Gly Leu Glu Asn Val Asp Leu Gly
145                 150                 155                 160

Phe Gly Lys Leu Ser Leu Ala Ala Thr Arg Asn Ser Glu Ser Gly Gly
                165                 170                 175

Ser Tyr Thr Phe Ser Ser Asp Ala Thr Lys Lys Tyr Ala Ala Lys Thr
            180                 185                 190

Ala Asn Asp Val Phe Asp Ile Arg Leu Ala Gly Leu Glu Thr Asn Pro
        195                 200                 205

Gly Gly Val Leu Glu Leu Gly Val Asp Tyr Gly Arg Ala Asn Pro Gln
    210                 215                 220

Asp Asp Tyr Arg Leu Glu Asp Gly Ala Ser Lys Asp Gly Trp Met Trp
225                 230                 235                 240

Thr Gly Glu His Thr Gln Ser Ile Trp Gly Gly Phe Asn Lys Phe Val
                245                 250                 255

Val Gln Tyr Ala Thr Asp Ala Met Thr Ser Trp Asn Ser Gly His Ser
            260                 265                 270

Gln Gly Thr Ser Ile Asp Asn Asn Gly Ser Met Ile Arg Val Leu Asp
        275                 280                 285

His Gly Ala Met Asp Phe Asn Asp Asp Trp Gly Leu Met Tyr Val Ala

```
                290                 295                 300
Met Tyr Gln Glu Leu Asp Leu Asp Ser Lys Asn Gly Ser Thr Trp Tyr
305                 310                 315                 320

Thr Val Gly Val Arg Pro Met Tyr Lys Trp Thr Pro Ile Met Ser Thr
            325                 330                 335

Gln Leu Glu Ile Gly Tyr Asp Asn Val Lys Ser Gln Arg Thr Ser Glu
            340                 345                 350

Asn Asn Asn Gln Tyr Lys Ile Thr Leu Ala Gln Gln Trp Gln Ala Gly
        355                 360                 365

Asn Ser Val Trp Ser Arg Pro Ala Ile Arg Ile Phe Ala Thr Tyr Ala
        370                 375                 380

Lys Trp Asp Glu Asn Trp Gly Tyr Ser Asn Thr Ser Gly Leu Gln Thr
385                 390                 395                 400

Lys Asp Ser Ser Gly Ser Gly Ala Phe Thr Ser Ser Arg Gly Asp Asp
            405                 410                 415

Ser Glu Val Thr Phe Gly Ala Gln Met Glu Val Trp Trp
            420                 425
```

<210> SEQ ID NO 22
<211> LENGTH: 12
<212> TYPE: PRT
<213> ORGANISM: Klebsiella pneumoniae

<400> SEQUENCE: 22

```
Asp Ser Ser Gly Ser Gly Ala Phe Thr Ser Ser Arg
1               5                   10
```

<210> SEQ ID NO 23
<211> LENGTH: 7
<212> TYPE: PRT
<213> ORGANISM: Klebsiella pneumoniae

<400> SEQUENCE: 23

```
Ile Phe Ala Thr Tyr Ala Lys
1               5
```

<210> SEQ ID NO 24
<211> LENGTH: 20
<212> TYPE: PRT
<213> ORGANISM: Klebsiella pneumoniae

<400> SEQUENCE: 24

```
Leu Ala Gly Leu Glu Thr Asn Pro Gly Gly Val Leu Glu Leu Gly Val
1               5                   10                  15

Asp Tyr Gly Arg
            20
```

<210> SEQ ID NO 25
<211> LENGTH: 7
<212> TYPE: PRT
<213> ORGANISM: Klebsiella pneumoniae

<400> SEQUENCE: 25

```
Leu Gly Gln Glu Leu Trp Lys
1               5
```

<210> SEQ ID NO 26
<211> LENGTH: 16
<212> TYPE: PRT
<213> ORGANISM: Klebsiella pneumoniae -continued

<400> SEQUENCE: 26

Asn Ser Glu Ser Gly Gly Ser Tyr Thr Phe Ser Ser Asp Asp Thr Lys
1               5                   10                  15

<210> SEQ ID NO 27
<211> LENGTH: 344
<212> TYPE: PRT
<213> ORGANISM: Klebsiella pneumoniae

<400> SEQUENCE: 27

Met Lys Ala Ile Phe Val Leu Asn Ala Ala Pro Lys Asp Asn Thr Trp
1               5                   10                  15

Tyr Ala Gly Gly Lys Leu Gly Trp Ser Gln Tyr His Asp Thr Gly Phe
                20                  25                  30

Tyr Gly Asn Gly Phe Gln Asn Asn Asn Gly Pro Thr Arg Asn Asp Gln
            35                  40                  45

Leu Gly Ala Gly Ala Phe Gly Gly Tyr Gln Val Asn Pro Tyr Leu Gly
        50                  55                  60

Phe Glu Met Gly Tyr Asp Trp Leu Gly Arg Met Ala Tyr Lys Gly Ser
65                  70                  75                  80

Val Asp Asn Gly Ala Phe Lys Ala Gln Gly Val Gln Leu Thr Ala Lys
                85                  90                  95

Leu Gly Tyr Pro Ile Thr Asp Asp Leu Asp Ile Tyr Thr Arg Leu Gly
            100                 105                 110

Gly Met Val Trp Arg Ala Asp Ser Lys Gly Asn Tyr Ala Ser Thr Gly
        115                 120                 125

Val Ser Arg Ser Glu His Asp Thr Gly Val Ser Pro Val Phe Ala Gly
130                 135                 140

Gly Val Glu Trp Ala Val Thr Arg Asp Ile Ala Thr Arg Leu Glu Tyr
145                 150                 155                 160

Gln Trp Val Asn Asn Ile Gly Asp Ala Gly Thr Val Gly Thr Arg Pro
                165                 170                 175

Asp Asn Gly Met Leu Ser Leu Gly Val Ser Tyr Arg Phe Gly Gln Glu
            180                 185                 190

Asp Ala Ala Pro Val Val Ala Pro Ala Pro Ala Pro Glu Val
        195                 200                 205

Ala Thr Lys His Phe Thr Leu Lys Ser Asp Val Leu Phe Asn Phe Asn
210                 215                 220

Lys Ala Thr Leu Lys Pro Glu Gly Gln Gln Ala Leu Asp Gln Leu Tyr
225                 230                 235                 240

Thr Gln Leu Ser Asn Met Asp Pro Lys Asp Gly Ser Ala Val Val Leu
                245                 250                 255

Gly Tyr Thr Asp Arg Ile Gly Ser Glu Ala Tyr Asn Gln Gln Leu Ser
            260                 265                 270

Glu Lys Arg Ala Gln Ser Val Val Asp Tyr Leu Val Ala Lys Gly Ile
        275                 280                 285

Pro Ala Gly Lys Ile Ser Ala Arg Gly Met Gly Glu Ser Asn Pro Val
290                 295                 300

Thr Gly Asn Thr Cys Asp Asn Val Lys Ala Arg Ala Ala Leu Ile Asp
305                 310                 315                 320

Cys Leu Ala Pro Asp Arg Arg Val Glu Ile Glu Val Lys Gly Tyr Lys
                325                 330                 335

Glu Val Val Thr Gln Pro Gln Ala
            340

<210> SEQ ID NO 28
<211> LENGTH: 11
<212> TYPE: PRT
<213> ORGANISM: Klebsiella pneumoniae

<400> SEQUENCE: 28

Ala Gln Ser Val Val Asp Tyr Leu Val Ala Lys
1               5                   10

<210> SEQ ID NO 29
<211> LENGTH: 12
<212> TYPE: PRT
<213> ORGANISM: Klebsiella pneumoniae

<400> SEQUENCE: 29

Asp Gly Ser Ala Val Val Leu Gly Tyr Thr Asp Arg
1               5                   10

<210> SEQ ID NO 30
<211> LENGTH: 7
<212> TYPE: PRT
<213> ORGANISM: Klebsiella pneumoniae

<400> SEQUENCE: 30

Leu Gly Gly Met Val Trp Arg
1               5

<210> SEQ ID NO 31
<211> LENGTH: 9
<212> TYPE: PRT
<213> ORGANISM: Klebsiella pneumoniae

<400> SEQUENCE: 31

Ser Asp Val Leu Phe Asn Phe Asn Lys
1               5

<210> SEQ ID NO 32
<211> LENGTH: 359
<212> TYPE: PRT
<213> ORGANISM: Klebsiella pneumoniae

<400> SEQUENCE: 32

Met Met Lys Arg Asn Ile Leu Ala Val Val Ile Pro Ala Leu Leu Val
1               5                   10                  15

Ala Gly Ala Ala Asn Ala Ala Glu Ile Tyr Asn Lys Asn Gly Asn Lys
            20                  25                  30

Leu Asp Phe Tyr Gly Lys Met Val Gly Glu His Val Trp Thr Thr Asn
        35                  40                  45

Gly Asp Thr Ser Ser Asp Thr Thr Tyr Ala Arg Ile Gly Leu Lys
    50                  55                  60

Gly Glu Thr Gln Ile Asn Asp Gln Leu Ile Gly Tyr Gly Gln Trp Glu
65                  70                  75                  80

Tyr Asn Met Asp Ala Ser Asn Val Glu Gly Ser Gln Thr Thr Lys Thr
                85                  90                  95

Arg Leu Ala Phe Ala Gly Leu Lys Ala Gly Glu Tyr Gly Ser Phe Asp
            100                 105                 110

Tyr Gly Arg Asn Tyr Gly Ala Ile Tyr Asp Val Glu Ala Ala Thr Asp
        115                 120                 125

Met Leu Val Glu Trp Gly Gly Asp Gly Trp Asn Tyr Thr Asp Asn Tyr
    130                 135                 140

```
Met Thr Gly Arg Thr Asn Gly Val Ala Thr Tyr Arg Asn Ser Asp Phe
145                 150                 155                 160

Phe Gly Leu Val Asp Gly Leu Ser Phe Ala Leu Gln Tyr Gln Gly Lys
            165                 170                 175

Asn Asp His Asp Arg Ala Ile Arg Lys Gln Asn Gly Asp Gly Phe Ser
        180                 185                 190

Thr Ala Thr Tyr Ala Phe Asp Asn Gly Ile Ala Leu Ser Ala Gly
        195                 200                 205

Tyr Ser Ser Asn Arg Ser Val Asp Gln Lys Ala Asp Gly Asn Gly
    210                 215                 220

Asp Lys Ala Glu Ala Trp Ala Thr Ser Ala Lys Tyr Asp Ala Asn Asn
225                 230                 235                 240

Ile Tyr Ala Ala Val Met Tyr Ser Gln Thr Tyr Asn Met Thr Pro Glu
                245                 250                 255

Glu Asp Asn His Phe Ala Gly Lys Thr Gln Asn Phe Glu Ala Val Val
        260                 265                 270

Gln Tyr Gln Phe Asp Phe Gly Leu Arg Pro Ser Ile Gly Tyr Val Gln
    275                 280                 285

Thr Lys Gly Lys Asp Leu Gln Ser Arg Ala Gly Phe Ser Gly Gly Asp
290                 295                 300

Ala Asp Leu Val Lys Tyr Ile Glu Val Gly Thr Trp Tyr Tyr Phe Asn
305                 310                 315                 320

Lys Asn Met Asn Val Tyr Ala Ala Tyr Lys Phe Asn Gln Leu Asp Asp
                325                 330                 335

Asn Asp Tyr Thr Lys Ala Ala Gly Val Ala Thr Asp Asp Gln Ala Ala
        340                 345                 350

Val Gly Ile Val Tyr Gln Phe
        355

<210> SEQ ID NO 33
<211> LENGTH: 11
<212> TYPE: PRT
<213> ORGANISM: Klebsiella pneumoniae

<400> SEQUENCE: 33

Ala Gly Glu Tyr Gly Ser Phe Asp Tyr Gly Arg
1               5                   10

<210> SEQ ID NO 34
<211> LENGTH: 12
<212> TYPE: PRT
<213> ORGANISM: Klebsiella pneumoniae

<400> SEQUENCE: 34

Ala Gly Phe Ser Gly Gly Asp Ala Asp Leu Val Lys
1               5                   10

<210> SEQ ID NO 35
<211> LENGTH: 11
<212> TYPE: PRT
<213> ORGANISM: Klebsiella pneumoniae

<400> SEQUENCE: 35

Phe Asn Gln Leu Asp Asp Asn Asp Tyr Thr Lys
1               5                   10

<210> SEQ ID NO 36
<211> LENGTH: 8
<212> TYPE: PRT
```

<213> ORGANISM: Klebsiella pneumoniae

<400> SEQUENCE: 36

Thr Asn Gly Val Ala Thr Tyr Arg
1               5